US009458125B2

(12) United States Patent
Sago et al.

(10) Patent No.: US 9,458,125 B2
(45) Date of Patent: Oct. 4, 2016

(54) OCTAHYDRO BINAPHTHYL-BASED CHIRAL COMPOUND-CONTAINING LIQUID-CRYSTAL COMPOSITION AND OPTICAL ELEMENT

(71) Applicants: JNC CORPORATION, Tokyo (JP); JNC PETROCHEMICAL CORPORATION, Tokyo (JP)

(72) Inventors: Koki Sago, Chiba (JP); Shin-Ichi Yamamoto, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/649,917

(22) PCT Filed: Dec. 12, 2013

(86) PCT No.: PCT/JP2013/083285
§ 371 (c)(1),
(2) Date: Jun. 5, 2015

(87) PCT Pub. No.: WO2014/097952
PCT Pub. Date: Jun. 26, 2014

(65) Prior Publication Data
US 2015/0291548 A1 Oct. 15, 2015

(30) Foreign Application Priority Data

Dec. 17, 2012 (JP) .................................. 2012-274679

(51) Int. Cl.
| | | |
|---|---|---|
| G02F 1/1333 | (2006.01) |
| C07D 317/10 | (2006.01) |
| C07D 319/06 | (2006.01) |
| C07D 321/00 | (2006.01) |
| G02F 1/137 | (2006.01) |
| C09K 19/58 | (2006.01) |
| C07D 239/26 | (2006.01) |
| C09K 19/54 | (2006.01) |
| C07D 309/04 | (2006.01) |
| C07D 317/12 | (2006.01) |
| C07D 405/12 | (2006.01) |
| C07D 407/12 | (2006.01) |
| C07D 493/18 | (2006.01) |
| C09K 19/20 | (2006.01) |
| C09K 19/32 | (2006.01) |
| C09K 19/34 | (2006.01) |
| C09K 19/04 | (2006.01) |

(52) U.S. Cl.
CPC .......... *C07D 317/10* (2013.01); *C07D 239/26* (2013.01); *C07D 309/04* (2013.01); *C07D317/12* (2013.01); *C07D 319/06* (2013.01); *C07D 321/00* (2013.01); *C07D 405/12* (2013.01); *C07D 407/12* (2013.01); *C07D 493/18* (2013.01); *C09K 19/20* (2013.01); *C09K 19/34* (2013.01); *C09K 19/542* (2013.01); *C09K 19/586* (2013.01); *C09K 19/588* (2013.01); *G02F 1/137* (2013.01); *C09K 2019/0411* (2013.01); *C09K 2019/0466* (2013.01); *C09K 2019/323* (2013.01); *C09K 2019/325* (2013.01); *C09K 2019/3422* (2013.01); *C09K 2019/3427* (2013.01); *C09K 2019/3433* (2013.01); *G02F 2001/13793* (2013.01)

(58) Field of Classification Search
CPC    C07D 317/10; C07D 319/06; C07D 321/00; C07D 239/26; C07D 309/12; C07D 405/12; C07D 407/12; C07D 493/18; C09K 19/588; C09K 19/542; C09K 19/34; C09K 19/586; C09K 19/20; C09K 2019/323; C09K 2019/325; C09K 2019/3433; C09K 2019/3422; C09K 2019/3427; C09K 2019/0411; C09K 2019/0466; G02F 1/137; G02F 1/1333; G02F 2001/13793
USPC .............. 252/299.01, 299.6, 299.62; 428/1.1
See application file for complete search history.

(56) References Cited

U.S. PATENT DOCUMENTS

| | | | |
|---|---|---|---|
| 7,223,450 B2 | 5/2007 | Taugerbeck et al. | |
| 8,585,925 B2* | 11/2013 | Czanta ................... | C09K 19/42 252/299.01 |
| 8,609,208 B2* | 12/2013 | Yamamoto ......... | C09K 19/0275 252/299.5 |
| 8,911,644 B2* | 12/2014 | Yamamoto ......... | C09K 19/3402 252/299.61 |
| 2004/0164273 A1 | 8/2004 | Motoyama et al. | |
| 2006/0006363 A1 | 1/2006 | Heckmeier et al. | |
| 2006/0050354 A1 | 3/2006 | Heckmeier et al. | |
| 2006/0227283 A1 | 10/2006 | Ooi et al. | |
| 2006/0286308 A1 | 12/2006 | Kirsch et al. | |
| 2008/0090026 A1 | 4/2008 | Bernatz et al. | |
| 2008/0259254 A1 | 10/2008 | Kikuchi et al. | |

| | | | |
|---|---|---|---|
| 2012/0032112 | A1 | 2/2012 | Czanta et al. |
| 2014/0132868 | A1* | 5/2014 | Sago ............... C09K 19/3402 349/42 |
| 2015/0240159 | A1* | 8/2015 | Yamamoto ......... C09K 19/3402 349/86 |

FOREIGN PATENT DOCUMENTS

| | | |
|---|---|---|
| CN | 100338054 | 9/2007 |
| CN | 101560395 | 10/2009 |
| JP | 2003-327966 | 11/2003 |
| JP | 2004-250397 | 9/2004 |
| JP | 2005-157109 | 6/2005 |
| JP | 2005-336477 | 12/2005 |
| JP | 2005-537520 | 12/2005 |
| JP | 2006-506477 | 2/2006 |
| JP | 2006-089622 | 4/2006 |
| JP | 2006-127707 | 5/2006 |
| JP | 2006-273978 | 10/2006 |
| JP | 2006-299084 | 11/2006 |
| JP | 2007-503487 | 2/2007 |
| JP | 2008-116931 | 5/2008 |
| JP | 2012-068645 | 4/2012 |
| JP | 2012-516920 | 7/2012 |
| WO | 2004/029697 | 4/2004 |
| WO | 2005/080529 | 9/2005 |
| WO | 2005-090520 | 9/2005 |

OTHER PUBLICATIONS

"International Search Report (Form PCT/ISA/210)", mailed on Mar. 25, 2014, with English translation thereof, pp. 1-4, in which four of the listed references (JP2008-116931A, JP2012-516920A, JP2012-068645A, and JP2006-273978A) were cited.

Kikuchi et al., "Polymer-Stabilized Liquid Crystal Blue Phases", Nature Materials, vol. 1, Sep. 2002, pp. 64-68.

Hisakado et al., "Large Electro—optic Kerr Effect in Polymer-Stabilized Liquid-CrystallineBlue Phases", Advanced Materials, 17, No. 1, Jan. 6, 2005, pp. 96-98.

Yasuhiro Haseba & Hirotsugu Kikuchi, "Electro-optic effects of the optically isotropic state induced by the incorporation effects of a polymer network and the chirality of liquid crystal", Journal of the SID vol. 14 (6), Jun. 2006, pp. 551-556.

"First Office Action of China Counterpart Application", issued on Dec. 28, 2015, pp. 1-16, with English translation thereof.

* cited by examiner

*Primary Examiner* — Geraldina Visconti

(74) *Attorney, Agent, or Firm* — Jianq Chyun IP Office

(57) ABSTRACT

A liquid-crystal composition is composed of at least one chiral compound represented by general formula (K1) or (K2) and at least one achiral liquid-crystal component:

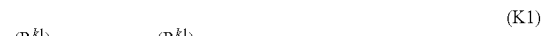

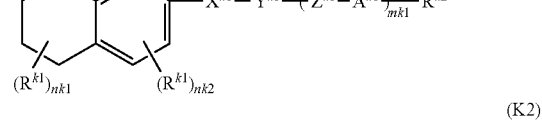

(wherein, in formulas (K1) and (K2), $R^{k1}$ is, for example, alkyl having 1 to 5 carbons, $R^{k2}$ is, for example, alkyl having 1 to 20 carbons, ring $A^{k1}$ is, for example, 1,4-phenylene, $X^{k1}$ is, for example, a single bond, $Y^{k1}$ is, for example, $-(CH_2)_n-$, n is an integer from 0 to 20, $Z^{k1}$ is, for example, a single bond, mk1 is, for example, an integer from 2 to 4, and nk1 and nk2 are, for example, an integer from 0 to 2).

20 Claims, 1 Drawing Sheet

OCTAHYDRO BINAPHTHYL-BASED CHIRAL COMPOUND-CONTAINING LIQUID-CRYSTAL COMPOSITION AND OPTICAL ELEMENT

CROSS-REFERENCE TO RELATED APPLICATION

This application is a 371 application of an international PCT application serial no. PCT/JP2013/083285, filed on Dec. 12, 2013, which claims the priority benefit of Japan application no. 2012-274679, filed on Dec. 17, 2012. The entirety of each of the abovementioned patent applications is hereby incorporated by reference herein and made a part of this specification.

TECHNICAL FIELD

The present invention relates to a liquid-crystal composition composed of a chiral compound and an achiral liquid-crystal component, and a liquid-crystal device using the liquid-crystal composition.

BACKGROUND ART

In a manner similar to an isotropic phase in a nematic liquid-crystal material (hereinafter, referred to as "non-liquid-crystal isotropic phase" in several cases), and also in a blue phase being one kind of an optically isotropic liquid-crystal phase, a Kerr effect ($\Delta n_E = K\lambda E^2$ (K: Kerr coefficient (Kerr constant), $\lambda$: wavelength)) is observed, being a phenomenon in which an electric birefringence value (birefringence value induced upon application of an electric field to an isotropic medium) $\Delta n_E$ is proportional to a square of electric field E.

Research has been recently conducted actively on a mode in the electric field is applied in the optically isotropic liquid-crystal phase, such as the blue phase and a polymer-stabilized blue phase to exhibit electric birefringence (Patent literature Nos. 1 to 11, Non-patent literature Nos. 1 to 3). Further, a proposal has been made on not only application of the mode to a display device but also application to a wavelength variable filter utilizing electric birefringence, a wavefront control element, a liquid-crystal lens, an aberration correction element, an aperture control element, an optical head device or the like (Patent literature Nos. 6, 10 and 11).

CITATION LIST

Patent Literature

Patent literature No. 1: JP 2003-327966 A.
Patent literature No. 2: WO 2005/90520 A.
Patent literature No. 3: JP 2005-336477 A.
Patent literature No. 4: JP 2006-89622 A.
Patent literature No. 5: JP 2006-299084 A.
Patent literature No. 6: WO 2005/080529 A.
Patent literature No. 7: JP 2005-537520 A.
Patent literature No. 8: JP 2006-506477 A.
Patent literature No. 9: JP 2007-503487 A.
Patent literature No. 10: JP 2005-157109 A.
Patent literature No. 11: JP 2006-127707 A.
Patent literature No. 12: U.S. Pat. No. 7,223,450 B.
Patent literature No. 13: JP 2004-250397 A.
Non-patent literature No. 1: Nature Materials, 1, 64, (2002).
Non-patent literature No. 2: Adv. Mater., 17, 96, (2005).
Non-patent literature No. 3: Journal of the SID, 14, 551, (2006).

SUMMARY OF INVENTION

Technical Problem

The invention is to provide a chiral compound having large helical twisting power (HTP), a low melting point and good compatibility with other liquid-crystal compounds; and a liquid-crystal composition having an optically isotropic liquid-crystal phase composed of the chiral compound and an achiral liquid-crystal component, and according to the invention, having a low drive voltage and good storage stability.

Solution to Problem

An optically isotropic liquid-crystal composition contains a chiral compound and an achiral liquid-crystal component. In general, as HTP of the chiral compound is larger, a helical pitch of a liquid-crystal can be shortened by adding a smaller amount of the chiral compound to a liquid-crystal composition. Therefore, an optically isotropic liquid-crystal phase is exhibited by adding a small amount of the chiral compound, and when the composition is used in the form of an optical element, an effect such as a decrease in drive voltage and suppression of precipitation of the chiral compound can be expected. The reason is that, in the optically isotropic liquid-crystal composition, the achiral liquid-crystal component contributes to the decrease in drive voltage, and a content of the achiral liquid-crystal component can be increased by using the chiral compound having large HTP.

Moreover, the chiral compound having a low melting point and good compatibility results in allowing an improvement in compatibility of the optically isotropic liquid-crystal composition, and when the composition is used in the form of the optical element, the optical element can be driven in a wide temperature range including the low temperature. Moreover, also upon preparation of the optically isotropic liquid-crystal composition, time required for dissolution can be significantly shortened, and therefore the optical device can be efficiently manufactured, and thus manufacturing cost can be reduced.

The present inventors have diligently continued to conduct research, and as a result, have found that the problem can be solved by using a 5,5',6,6',7,7',8,8'-octahydro-1,1'-bi-2-naphthyl derivative as the chiral compound. The chiral compound of the invention has features of large HTP, a low melting point and good compatibility with the liquid-crystal composition. Specifically, the invention is as described below.

[1] A liquid-crystal composition composed of at least one chiral compound represented by general formula (K1) or (K2) and at least one achiral liquid-crystal component:

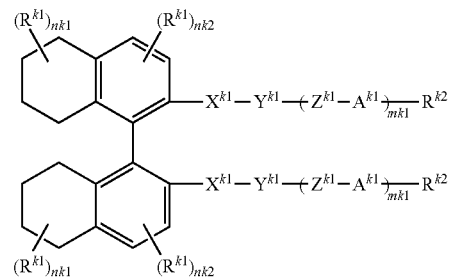

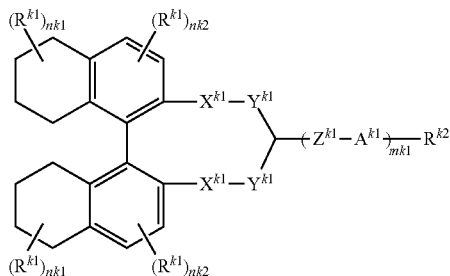

(K2)

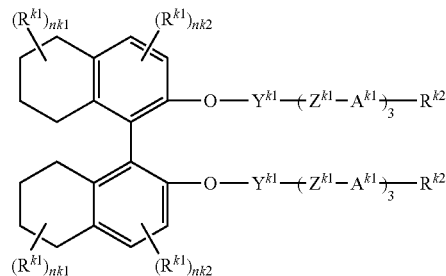

(K1-2)

(wherein, in formulas (K1) and (K2), $R^{k1}$ is halogen, cyano, —SF$_5$ or alkyl having 1 to 5 carbons, at least one of —CH$_2$— in $R^{k1}$ may be replaced by —O—, —COO—, —OCO—, —CH=CH— or —C≡C—, and at least one of hydrogen in $R^{k1}$ may be replaced by halogen;

$R^{k2}$ is halogen, cyano, —SF$_5$ or alkyl having 1 to 20 carbons, at least one of —CH$_2$— in $R^{k2}$ may be replaced by —O—, —COO—, —OCO—, —CH=CH— or —C≡C—, and at least one of hydrogen in $R^{k2}$ may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl, pyridine-2,5-diyl or 1,4-bicyclo-(2,2,2)-octylene, and at least one of hydrogen in the rings may be replaced by halogen;

$X^{k1}$ is a single bond, —O—, —CO—, —COO—, —OCO—, —OCH$_2$—, —CH$_2$O—, —CF$_2$O—, —OCF$_2$—, —CH=CH—, —CF$_2$CF$_2$—, —CF=CF— or —C≡C—;

$Y^{k1}$ is a single bond or —(CH$_2$)$_n$—, and n is an integer from 1 to 20;

$Z^{k1}$ is a single bond or alkylene having 1 to 10 carbons, at least one of —CH$_2$— in $Z^{k1}$ may be replaced by —O—, —COO—, —OCO—, —CH=CH—, —CF=CF— or —C≡C—, and at least one of hydrogen in $Z^{k1}$ may be replaced by halogen;

mk1 is an integer from 2 to 4; nk1 and nk2 are integers from 0 to 2; and when a plurality of $R^{k1}$, $R^{k2}$, $A^{k1}$, $A^{k2}$, $X^{k1}$, $Y^{k1}$, $Z^{k1}$, mk1, nk1 or nk2 exist, the plurality may be identical or different each other).

[2] A liquid-crystal composition composed of at least one chiral compound selected from compounds represented by general formulas (K1-1) to (K1-6) and at least one achiral liquid-crystal component:

(K1-1)

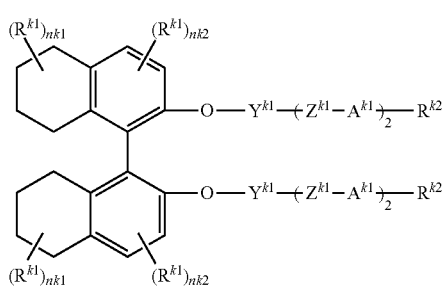

(K1-3)

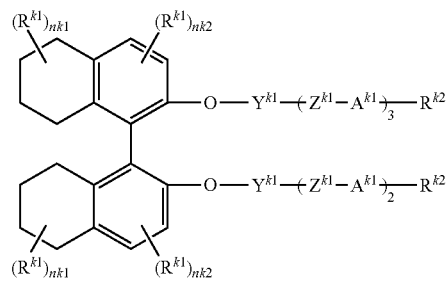

(K1-4)

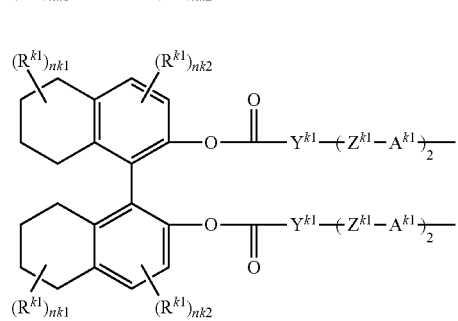

(K1-5)

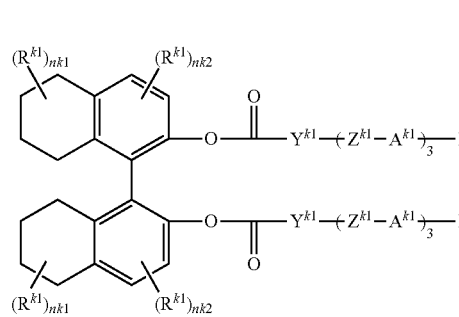

(K1-6)

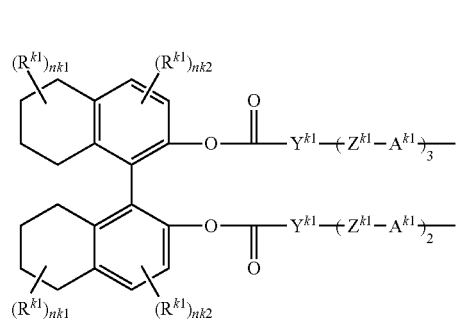

(wherein, in formulas (K1-1) to (K1-6), $R^{k1}$ is halogen, cyano, —SF$_5$ or alkyl having 1 to 5 carbons, at least one of —CH$_2$— in $R^{k1}$ may be replaced by —O—, —COO—, —OCO—, —CH=CH— or —C≡C—, and at least one of hydrogen in $R^{k1}$ may be replaced by halogen;

$R^{k2}$ is halogen, cyano, —SF$_5$ or alkyl having 1 to 20 carbons, at least one of —CH$_2$— in $R^{k2}$ may be replaced by —O—, —COO—, —OCO—, —CH═CH— or —C≡C—, and at least one of hydrogen in $R^{k2}$ may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyridine-2,5-diyl, pyrimidine-2,5-diyl or 1,4-bicyclo-(2,2,2)-octylene, and at least one of hydrogen in the rings may be replaced by halogen;

$Y^{k1}$ is a single bond or —(CH$_2$)$_n$—, and n is an integer from 1 to 20;

$Z^{k1}$ is a single bond or alkylene having 1 to 10 carbons, at least one of —CH$_2$— in $Z^{k1}$ may be replaced by —O—, —COO—, —OCO—, —CH═CH—, —CF═CF— or —C≡C—, and at least one of hydrogen in $Z^{k1}$ may be replaced by halogen;

nk1 and nk2 are an integer from 0 to 2; and when a plurality of $R^{k1}$, $R^{k2}$, $A^{k1}$, $A^{k2}$, $Y^{k1}$, $Z^{k1}$, nk1 or nk2 exist, the plurality may be identical or different each other).

[3] A liquid-crystal composition composed of at least one chiral compound represented by general formula (K2-1) or (K2-2) and at least one achiral liquid-crystal component:

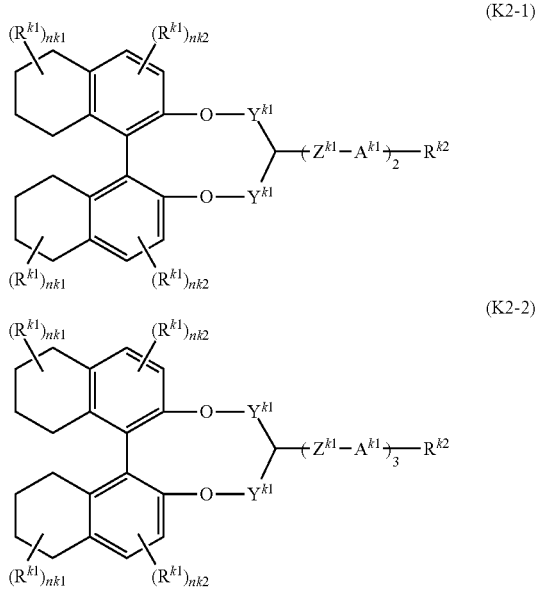

(wherein, in formulas (K2-1) to (K2-2), $R^{k1}$ is halogen, cyano, —SF$_5$ or alkyl having 1 to 5 carbons, at least one of —CH$_2$— in the alkyl may be replaced by —O—, —COO—, —OCO—, —CH═CH— or —C≡C— and at least one of hydrogen in the alkyl may be replaced by halogen;

$R^{k2}$ is halogen, cyano, —SF$_5$ or alkyl having 1 to 20 carbons, at least one of —CH$_2$— in the alkyl may be replaced by —O—, —COO—, —OCO—, —CH═CH— or —C≡C—, and at least one of hydrogen in the alkyl may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyridine-2,5-diyl, pyrimidine-2,5-diyl or 1,4-bicyclo-(2,2,2)-octylene, and at least one of hydrogen in the rings may be replaced by halogen;

$Y^{k1}$ is a single bond or —(CH$_2$)$_n$—, and n is an integer from 1 to 20;

$Z^{k1}$ is a single bond or alkylene having 1 to 10 carbons, at least one of —CH$_2$— in the alkylene may be replaced by —O—, —COO—, —OCO—, —CH═CH—, —CF═CF— or —C≡C—, and at least one of hydrogen in the alkylene may be replaced by halogen;

nk1 or nk2 is an integer from 0 to 2; and when a plurality of $R^{k1}$, $R^{k2}$, $A^{k1}$, $A^{k2}$, $Y^{k1}$, $Z^{k1}$, nk1 or nk2 exist, the plurality may be identical or different each other).

[4] A liquid-crystal composition composed of at least one chiral compound represented by general formula (K1-1-1), (K1-1-2), (K1-2-1), (K1-2-2), (K1-4-1), (K1-4-2), (K1-5-1) or (K1-5-2) and at least one achiral liquid-crystal component:

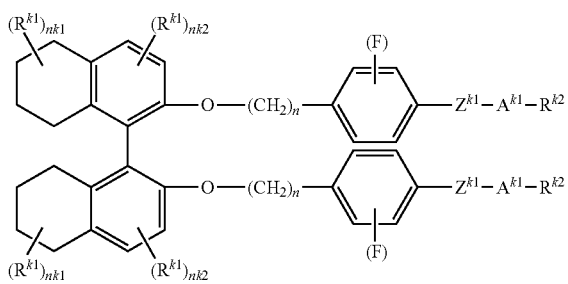

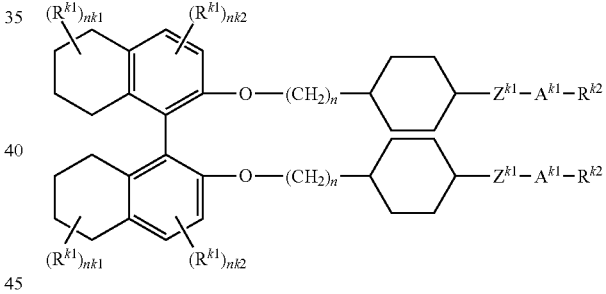

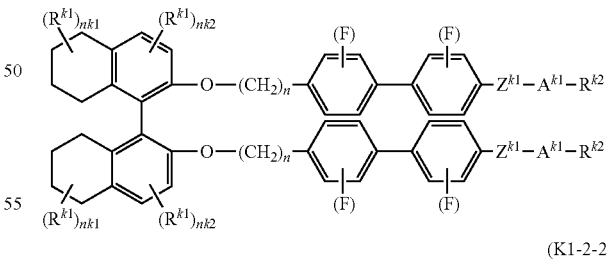

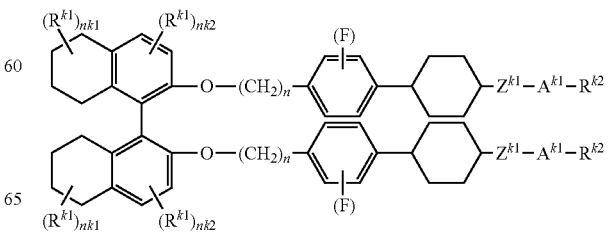

-continued (K1-4-1)
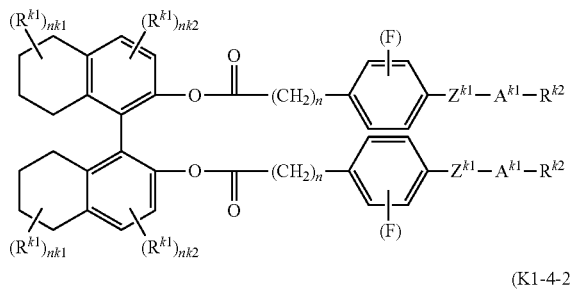

(K1-4-2)
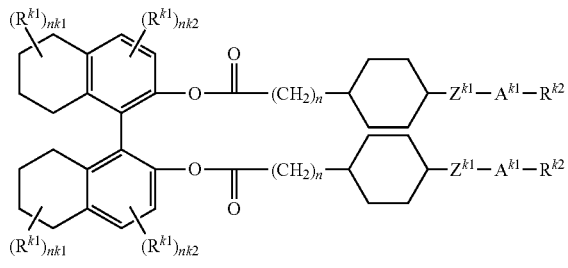

(K1-5-1)
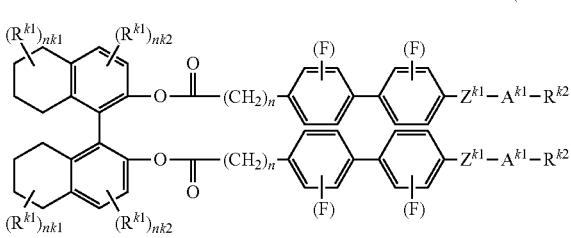

(K1-5-2)
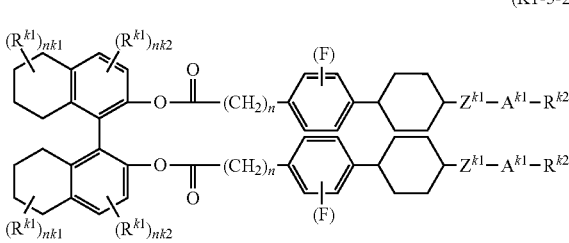

(K2-1-1)
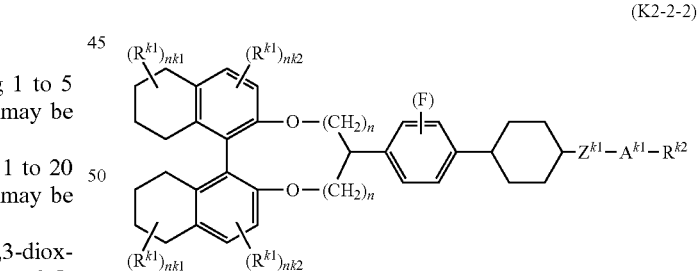

(K2-1-2)

(K2-2-1)

(K2-2-2)
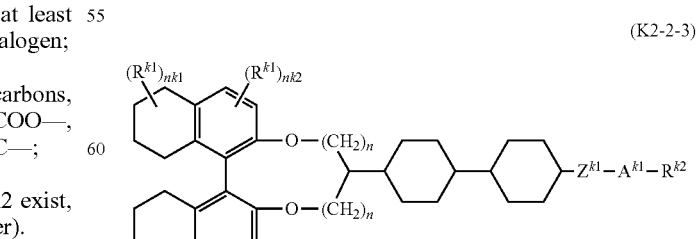

(K2-2-3)

(wherein, in the formulas, $R^{k1}$ is hydrogen, halogen, cyano or alkyl having 1 to 5 carbons, and at least one of hydrogen in the alkyl may be replaced by halogen;

$R^{k2}$ is hydrogen, halogen, cyano or alkyl having 1 to 20 carbons, and at least one of hydrogen in the alkyl may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl or pyridine-2,5-diyl, and at least one of hydrogen in the rings may be replaced by halogen;

n is an integer from 0 to 10;

$Z^{k1}$ is a single bond, alkylene having 1 to 10 carbons, —CH$_2$O—, —OCH$_2$—, —CF$_2$O—, —OCF$_2$—, —COO—, —OCO—, —CH═CH—, —CF═CF— or —C≡C—;

nk1 or nk2 is an integer from 0 to 2; and when a plurality of $R^{k1}$, $R^{k2}$, $A^{k1}$, $Z^{k1}$, nk1 or nk2 exist, the plurality may be identical or different each other).

[5] A liquid-crystal composition composed of at least one chiral compound represented by general formula (K2-1-1), (K2-1-2), (K2-2-1), (K2-2-2) or (K2-2-3) and at least one achiral liquid-crystal component:

(wherein, in formulas (K2-1-1) to (K2-2-3), $R^{k1}$ is hydrogen, halogen, cyano or alkyl having 1 to 5 carbons, and at least one of hydrogen in the alkyl may be replaced by halogen;

$R^{k2}$ is hydrogen, halogen, cyano or alkyl having 1 to 20 carbons, and at least one of hydrogen in the alkyl may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl or pyridine-2,5-diyl, and at least one of hydrogen in the rings may be replaced by halogen;

n is an integer from 0 to 10;

$Z^{k1}$ is a single bond, alkylene having 1 to 10 carbons, —CH$_2$O—, —OCH$_2$—, —CF$_2$O—, —OCF$_2$—, —COO—, —OCO—, —CH=CH—, —CF=CF— or —C≡C—;

nk1 or nk2 is an integer from 0 to 2; and when a plurality of $R^{k1}$, $R^{k2}$, $A^{k1}$, $Z^{k1}$, nk1 or nk2 exist, the plurality may be identical or different each other).

[6] The liquid-crystal composition according to any one of [1] to [5], containing at least one compound represented by general formula (1-A) is contained in the achiral liquid-crystal component:

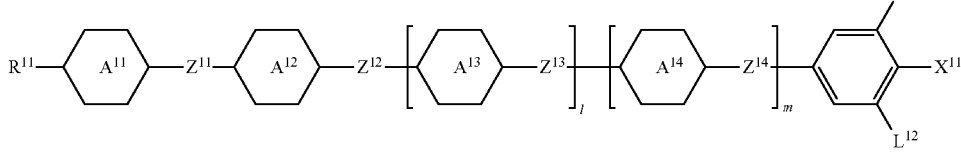

(1-A)

(wherein, in general formula (1-A), $R^{11}$ is hydrogen or alkyl having 1 to 20 carbons, at least one of —CH$_2$— in the alkyl may be replaced by —O—, —S—, —COO—, —OCO— or —C≡C— but a case where two successive —CH$_2$— are replaced by —O— is excluded, and at least one of hydrogen in the alkyl may be replaced by halogen; ring $A^{11}$, ring $A^{12}$, ring $A^{13}$ and ring $A^{14}$ are independently 1,4-phenylene, 1,3-dioxane-2,5-diyl, tetrahydropyran-2,5-diyl, tetrahydropyran-3,6-diyl, pyrimidine-2,5-diyl, pyridine-2,5-diyl, naphthalene-2,6-diyl, bicyclo[2,2,2]octane-1,4-diyl, 1,4-cyclohexylene or 2,6,7-trioxabicyclo[2,2,2]octane-1,4-diyl, and at least one of hydrogen in the rings may be replaced by halogen; $Z^{11}$, $Z^{12}$, $Z^{13}$ and $Z^{14}$ are independently a single bond and alkylene having 1 to 4 carbons, at least one of —CH$_2$— in the alkylene may be replaced by —O—, —S—, —COO—, —OCO—, —CF$_2$O—, —OCF$_2$—, —CH=CH—, —CF=CF— or —C≡C—, and at least one of hydrogen in the alkylene may be replaced by halogen; $L^{11}$ and $L^{12}$ are each independently hydrogen or halogen; $X^{11}$ is halogen, —C≡N, —N=C=S, —C≡C—C≡N, —SF$_5$, —CHF$_2$, —CF$_3$, —CF$_2$CH$_2$F, —CF$_2$CHF$_2$, —CF$_2$CF$_3$, —(CF$_2$)$_3$—F, —CF$_2$CHFCF$_3$, —CHFCF$_2$CF$_3$, —(CF$_2$)$_4$—F, —(CF$_2$)$_5$—F, —OCHF$_2$, —OCF$_3$, —OCF$_2$CH$_2$F, —OCF$_2$CHF$_2$, —OCH$_2$CF$_3$, —OCF$_2$CF$_3$, —O—(CF$_2$)$_3$—F, —OCF$_2$CHFCF$_3$, —OCHFCF$_2$CF$_3$, —O—(CF$_2$)$_4$—F, —O—(CF$_2$)$_5$—F, —CH=CF$_2$, —CH=CHCF$_3$ or —CH=CHCF$_2$CF$_3$; and l and m are independently 0 or 1).

[7] The liquid-crystal composition according to any one of [1] to [6], containing a compound represented by general formula (1-A) in an amount of 50 to 100% by weight in the achiral liquid-crystal component.

[8] The liquid-crystal composition according to any one of [1] to [7], containing a compound represented by general formula (1-A) in an amount of 50 to 100% by weight in the achiral liquid-crystal component, and further containing at least one chiral compound selected from compounds represented by general formulas (K11) to (K15):

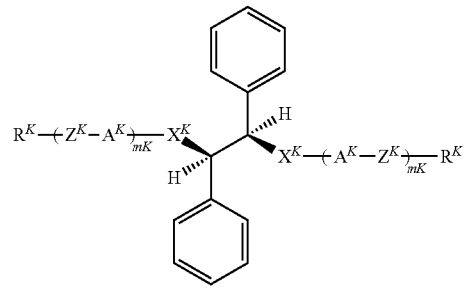

(K11)

-continued

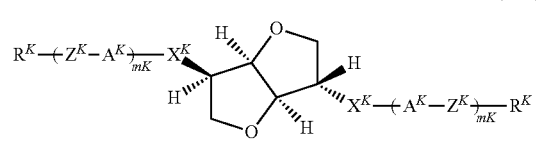

(K12)

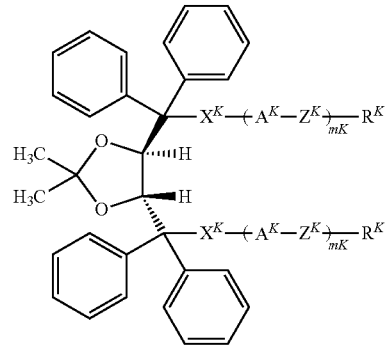

(K13)

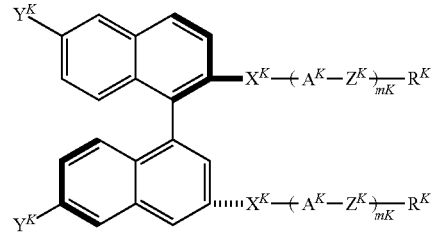

(K14)

-continued (K15)

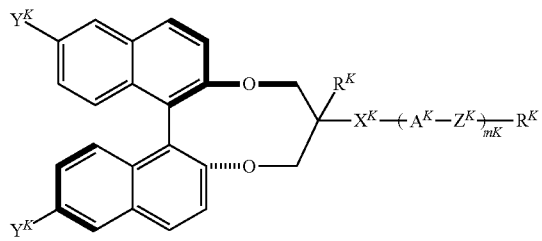

(wherein, in formulas (K11) to (K15), $R^K$ is independently hydrogen, halogen, —C≡N, —N=C=O, —N=C=S or alkyl having 1 to 20 carbons, at least one of —CH$_2$— in the alkyl may be replaced by —O—, —S—, —COO—, —OCO—, —CH=CH—, —CF=CF— or —C≡C—, and at least one of hydrogen in the alkyl may be replaced by halogen;

$A^K$ is independently an aromatic 6-membered to 8-membered ring, nonaromatic 3-membered to 8-membered ring or a condensed ring having 9 to 20 carbons, at least one of hydrogen in the rings may be replaced by halogen, alkyl or haloalkyl each having 1 to 3 carbons, —CH$_2$— in the ring may be replaced by —O—, —S— or —NH—, and —CH= may be replaced by —N=;

$Y^K$ is independently hydrogen, halogen, alkyl having 1 to 3 carbons, haloalkyl having 1 to 3 carbons, an aromatic 6-membered to 8-membered ring, a nonaromatic 3-membered to 8-membered ring or a condensed ring having 9 to 20 carbons, at least one of hydrogen in the rings may be replaced by halogen, alkyl or haloalkyl each having 1 to 3 carbons, —CH$_2$— may be replaced by —O—, —S— or —NH—, and —CH= may be replaced by —N=; $Z^K$ is independently a single bond or alkylene having 1 to 8 carbons, but at least one of —CH$_2$— may be replaced by —O—, —S—, —COO—, —OCO—, —CSO—, —OCS—, —N=N—, —CH=N—, —N=CH—, —CH=CH—, —CF=CF— or —C≡C—, and at least one of hydrogen may be replaced by halogen; $X^K$ is a single bond, —COO—, —OCO—, —CH$_2$O—, —OCH$_2$—, —CF$_2$O—, —OCF$_2$— or —CH$_2$CH$_2$—; and mK is an integer from 1 to 4.)

[9] The liquid-crystal composition according to any one of [1] to [5], containing at least one compound represented by any one of general formulas (1-A-01) to (1-A-16) in the achiral liquid-crystal component:

(1-A-01)

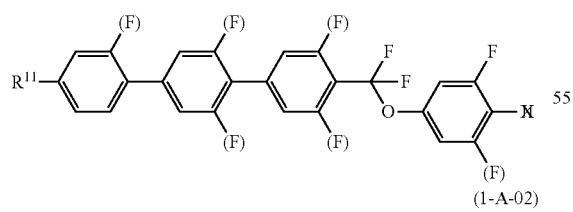

(1-A-02)

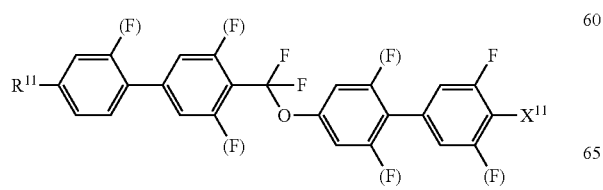

(1-A-03)

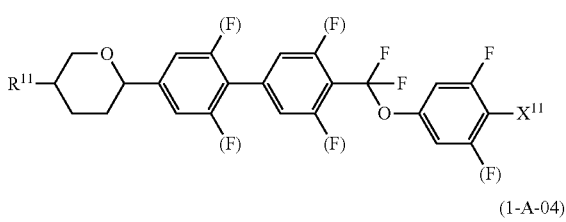

(1-A-04)

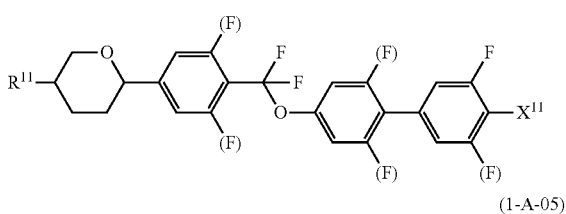

(1-A-05)

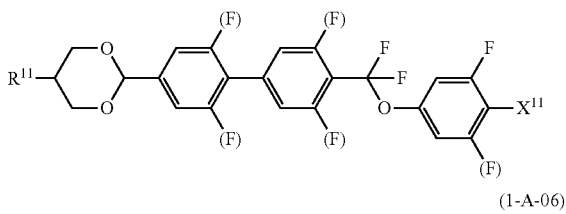

(1-A-06)

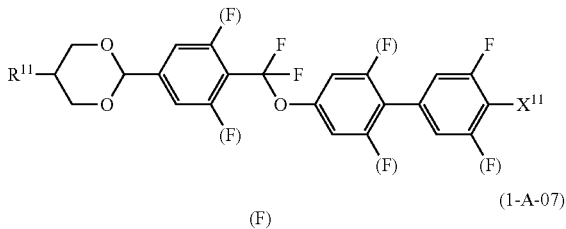

(1-A-07)

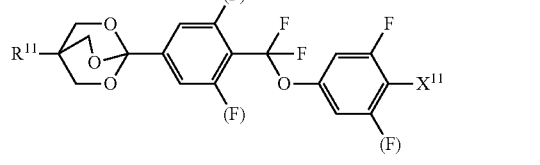

(1-A-08)

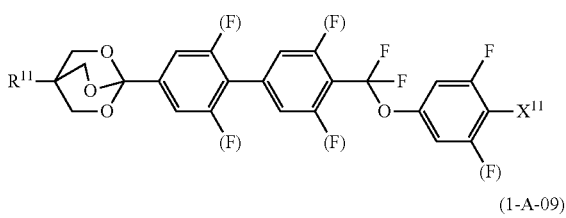

(1-A-09)

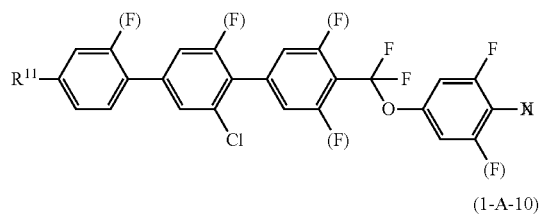

(1-A-10)

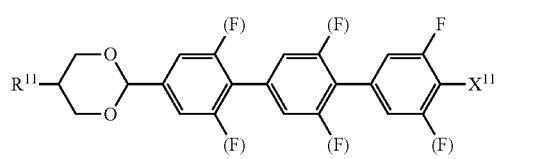

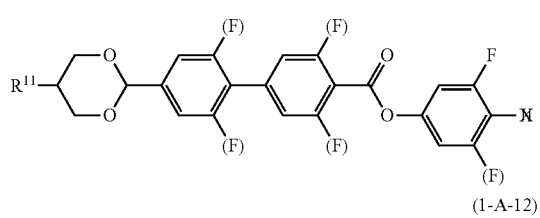
(1-A-11)

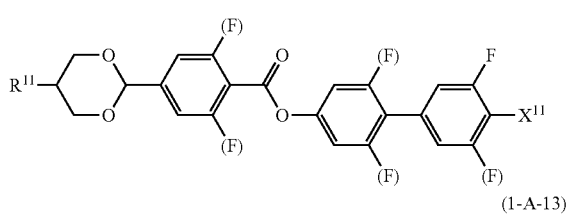
(1-A-12)

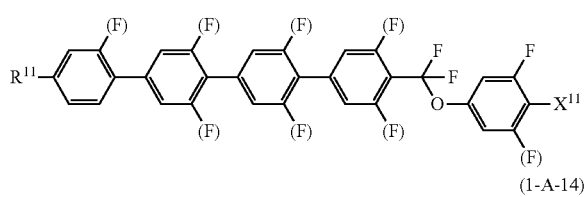
(1-A-13)

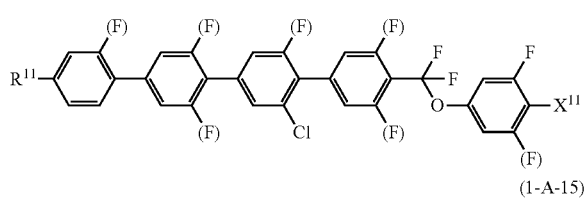
(1-A-14)

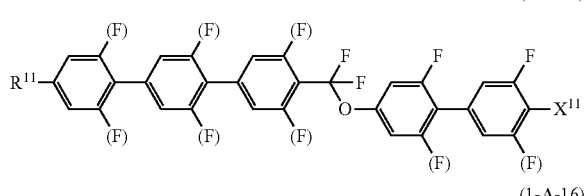
(1-A-15)

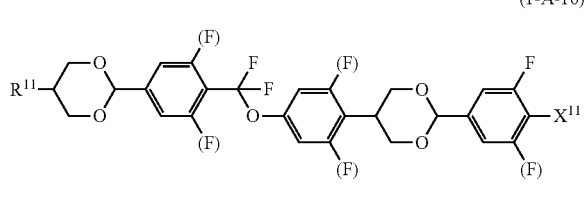
(1-A-16)

(wherein, in formulas (1-A-01) to (1-A-16), $R^{11}$ is hydrogen or alkyl having 1 to 8 carbons, $X^{11}$ is fluorine, chlorine, —C≡N, —CF$_3$, —CHF$_2$, —CH$_2$F, —OCF$_3$, —OCHF$_2$, —OCH$_2$F or —C≡C—CF$_3$, and (F) represents hydrogen or fluorine).

[10] The liquid-crystal composition according to any one of [1] to [5], containing at least one compound represented by any one of general formulas (1-A-01) to (1-A-16) in the achiral liquid-crystal component, wherein a content of the compound is 50 to 100% by weight.

[11] The liquid-crystal composition according to any one of [1] to [5], containing at least one compound represented by any one of general formulas (1-A-01) to (1-A-16) in the achiral liquid-crystal component, and further containing at least one compound represented by general formulas (K11) to (K15) in chiral component K.

[12] The liquid-crystal composition according to any one of [1] to [11], wherein a content of the chiral compound is 0.1 to 30% by weight.

[13] The liquid-crystal composition according to any one of [1] to [12], wherein a content of the compound represented by general formula (1-A) is 50 to 100% by weight in the achiral liquid-crystal component.

[14] The liquid-crystal composition according to any one of [1] to [12], wherein a content of the compound represented by any one of general formulas (1-A-01) to (1-A-16) is 50 to 100% by weight in the achiral liquid-crystal component.

[15] The liquid-crystal composition according to any one of [1] to [14], exhibiting a chiral nematic phase of at least 1° C. or more in the temperature range of 20 to 70° C., wherein a helical pitch is 700 nanometers or less at least partially in the temperature range.

[16] A monomer-liquid-crystal mixture, containing the optically isotropic liquid-crystal composition according to any one of [1] to [15] and a polymerizable monomer.

[17] The monomer-liquid-crystal mixture according to [16], exhibiting a chiral nematic phase of least 1° C. or more in the temperature range of −20 to 70° C., wherein a helical pitch is 700 nanometers or less at least partially in the temperature range.

[18] A polymer-liquid-crystal composite material, obtained by polymerizing the monomer-liquid-crystal mixture according to [16] or [17], and used in an element driven in the optically isotropic liquid-crystal phase.

[19] A polymer-liquid-crystal composite material, obtained by polymerizing the monomer-liquid-crystal mixture according to [16] or [17] in a non-liquid-crystal isotropic phase or an optically isotropic liquid-crystal phase, and used in an element driven in the optically isotropic liquid-crystal phase.

[20] A liquid-crystal device, having an electrode arranged on one side or both sides, a liquid-crystal composition or a polymer-liquid-crystal composite material arranged between substrates, and an electric field applying means for applying an electric field to the liquid-crystal composition or the polymer-liquid-crystal composite material through the electrode, wherein the polymer-liquid-crystal composite material is according to [18] or [19].

[21] The chiral compound, represented by general formula (K1-2-1) or (K1-2-2) according to [4].

[22] The chiral compound represented by general formula (K1-5-1) or (K1-5-2) according to [4].

[23] The chiral compound represented by general formula (K2-1-1) or (K2-1-2) according to [5].

[24] The chiral compound represented by any one of general formulas (K2-2-1) to (K2-2-3) according to [5].

"Liquid-crystal compound" herein is a generic term for a compound having a liquid-crystal phase such as a nematic phase or a smectic phase, and a compound having no liquid-crystal phase but being useful as a component for the liquid-crystal composition. The liquid-crystal compound, the liquid-crystal composition and a liquid-crystal display device may be occasionally abbreviated as "compound," "composition" and "device", respectively.

"Liquid-crystal device" herein is a generic term for a liquid-crystal display panel and a liquid-crystal display module. A maximum temperature of the nematic phase is a phase transition temperature between the nematic phase and an isotropic phase, and may be occasionally abbreviated simply as a clearing point or the maximum temperature. A minimum temperature of the nematic phase may be occasionally abbreviated simply as the minimum temperature.

"Compound represented by formula (1)" herein may be occasionally abbreviated as "compound (1)." The abbreviation may also apply to a compound represented by formula (2) or the like. In chemical formulas, a symbol A, B or the like surrounded by a hexagonal shape corresponds to ring structure A, ring structure B or the like, respectively. "Ring structure A" and "ring structure B" may be occasionally abbreviated as "ring A" and "ring B." "Ring structure" means a cyclic group, and includes a benzene ring, a naphthalene ring, a cyclohexene ring, a bicyclooctane ring and a cyclohexane ring. Here, ring structure containing a plurality of rings, such as a condensed polycyclic hydrocarbon such as a naphthalene ring, and a crosslinked ring hydrocarbon such as a bicyclooctane ring is also counted as one in the form of ring structure.

A plurality of identical symbols such as ring $A^1$, $Y^1$ and B are described in identical or different formulas, and the plurality each may be identical or different.

"At least one" represents that not only positions but also the number is arbitrary without including the case where the number is zero (0). An expression "at least one of A may be replaced by B, C or D" means inclusion of a case where at least one of A is replaced by B, a case where at least one of A is replaced by C, and a case where at least one of A is replaced by D, and also a case where a plurality of A are replaced by at least two of B, C and D. For example, alkyl in which at least one of —$CH_2$— may be replaced by —O— or —CH=CH— includes alkyl, alkenyl, alkoxy, alkoxyalkyl, alkoxyalkenyl and alkenyloxyalkyl. In addition, in the invention, a case where two successive —$CH_2$— are replaced by —O— to form —O—O— or the like is not preferred. Then, a case where a terminal —$CH_2$— in alkyl is replaced by —O— is also not preferred, either.

Moreover, unless otherwise noted herein, "%" is expressed in terms of "% by weight."

Effects of Invention

A liquid-crystal composition composed of a chiral compound and an achiral liquid-crystal component according to a preferred embodiment of the invention are preferably used in the form of an optical element. The chiral compound having large HTP, a low melting point and good compatibility can efficiently prepare an optically isotropic liquid-crystal composition in a smaller content and in a short period of time. Moreover, a liquid-crystal phase can be shown in a wide temperature range including a low temperature.

The liquid-crystal composition, the optically isotropic liquid-crystal composition and a polymer-liquid-crystal composite material exhibit a relatively large Kerr coefficient. More specifically, a relatively low drive voltage is shown. The optically isotropic liquid-crystal composition and the polymer-liquid-crystal composite material according to the preferred embodiment of the invention have a high response speed. The optically isotropic liquid-crystal composition and the polymer-liquid-crystal composite material according to the preferred embodiment of the invention can be used in a wide temperature range.

Then, the optically isotropic liquid-crystal composition and the polymer-liquid-crystal composite material according to the preferred embodiment of the invention can be preferably used in a liquid-crystal display device for a high speed response or the like based on effects thereof.

DESCRIPTION OF EMBODIMENTS

Figure 1:
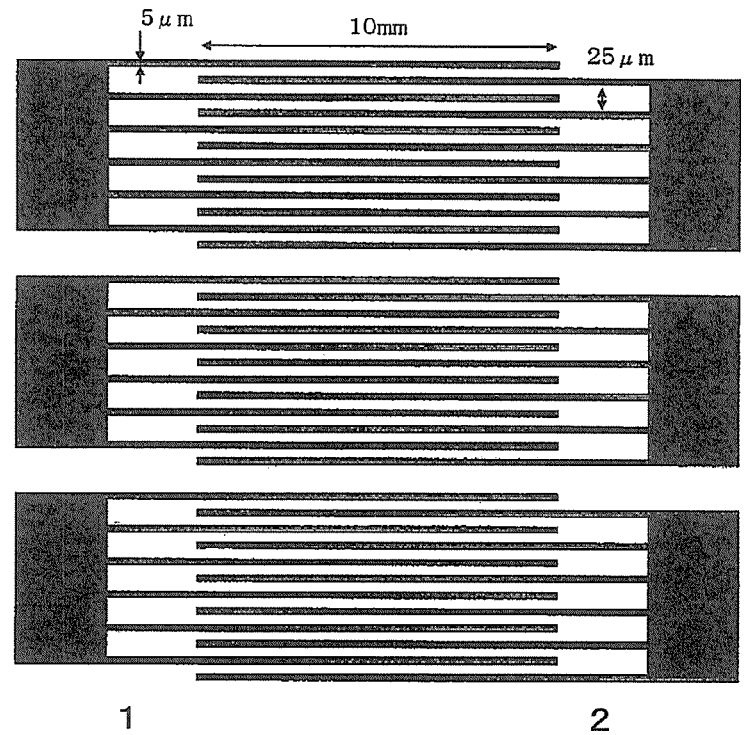
FIG. 1 shows a comb-like electrode substrate used in Examples.

1 Optically Isotropic Liquid-Crystal Composition of the Invention

A first embodiment of the invention is a liquid-crystal composition that can be used for a liquid-crystal device driven in an optically isotropic liquid-crystal phase.

The optically isotropic liquid-crystal composition of the invention has a compound represented by formula (K1) described above as a chiral agent and an achiral liquid-crystal component. Here, chirality of the chiral agent may be present or absent.

The compound contained in the liquid-crystal composition of the invention is generally prepared according to a publicly known method, for example, a method for allowing necessary components to react under a high temperature.

Moreover, with regard to each element of the compound constituting the liquid-crystal composition used in the invention, an analog including an isotopic element can be used, as long as no significant difference in physical characteristics exists.

1.1 Optically Isotropic Liquid-Crystal Phase

A liquid-crystal composition of the invention contains the optically isotropic liquid-crystal phase. Here, an expression "the liquid-crystal composition has optical isotropy" means that macroscopically, a liquid-crystal molecule sequence optically shows isotropy because the liquid-crystal molecule sequence is isotropic, but microscopically, a liquid-crystalline order exists.

Then, "optically isotropic liquid-crystal phase" herein represents a phase exhibiting the optically isotropic liquid-crystal phase without fluctuation, and for example, a phase exhibiting a platelet tissue (blue phase in a narrow sense) is one example thereof.

In general, the blue phase is classified into three kinds (blue phase I, blue phase II and blue phase III), and all of the three kinds of blue phases are optically active and isotropic. Two or more kinds of diffracted light beams due to Bragg reflection from different lattice planes in the blue phases of blue phase I and blue phase II are observed.

In the optically isotropic liquid-crystal composition of the invention, in order to exhibit the optically isotropic liquid-crystal phase, a helical pitch based on a microscopically included liquid-crystalline order (hereinafter, simply referred to as "pitch" in several cases) is preferably 1,000 nanometers or less.

Electric birefringence in the optically isotropic liquid-crystal phase becomes larger as the pitch becomes longer, and thus as long as desired optical characteristics (transmittance, diffraction wavelength or the like) are satisfied, the electric birefringence can be increased by adjusting a kind and a content of the chiral agent and setting a long pitch.

Moreover, "non-liquid-crystal isotropic phase" herein means an isotropic phase defined in general, namely, a disorder phase, and the isotropic phase in which even when a region whose local order parameter is not zero is formed, a cause thereof depends on fluctuation. For example, an isotropic phase exhibited on a high temperature side of the nematic phase corresponds to the non-liquid-crystal isotropic phase herein. A similar definition is to be applied to a chiral liquid-crystal herein.

1.2 Chiral Compound
1.2.1 Chiral Compound (K1) and (K2)

A chiral compound contained in the liquid-crystal composition of the invention is a compound represented by formula (K1) or (K2).

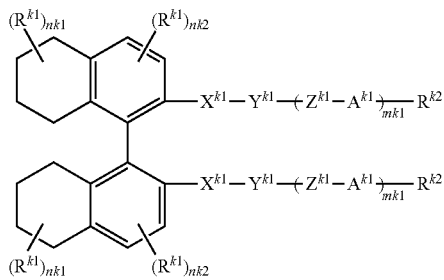

(K1)

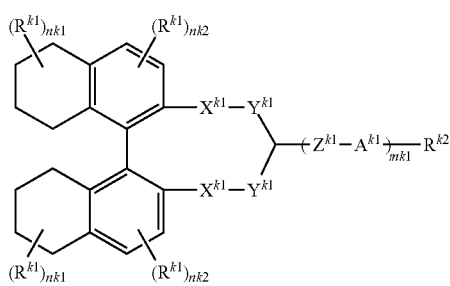

(K2)

In formulas (K1) and (K2), $R^{k1}$ is hydrogen, halogen, cyano, —$SF_5$ or alkyl having 1 to 5 carbons, at least one of —$CH_2$— in the alkyl may be replaced by —O—, —S—, —COO—, —OCO—, —CH=CH— or —C≡C—, and at least one of hydrogen in the alkyl may be replaced by halogen.

Preferred examples include hydrogen or alkyl having 1 to 5 carbons, alkenyl having 1 to 5 carbons and alkynyl having 2 to 5 carbons.

$R^{k2}$ is hydrogen, halogen, cyano, —$SF_5$ or alkyl having 1 to 20 carbons, at least one of —$CH_2$— in the alkyl may be replaced by —O—, —S—, —COO—, —OCO—, —CH=CH— or —C≡C— and at least one of hydrogen in the alkyl may be replaced by halogen.

Preferred examples include alkyl having 1 to 7 carbons, alkenyl having 2 to 7 carbons and alkynyl having 2 to 7 carbons.

Ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl, pyridine-2,5-diyl or 1,4-bicyclo-(2,2,2)-octylene, and at least one of hydrogen in the rings may be replaced by halogen.

Preferred examples include 1,4-phenylene, 1,4-cyclohexylene, 1,4-phenylene in which one or two of hydrogen are replaced by halogen, or 1,3-dioxane-diyl, and the compound has large HTP and good compatibility with other liquid-crystal compounds.

$X^{k1}$ is a single bond, —O—, —CO—, —COO—, —OCO—, —$OCH_2$—, —$CH_2O$—, —$CF_2O$—, —$OCF_2$—, —CH=CH—, —$CF_2CF_2$—, —CF=CF— or —C≡C—.

Preferred examples include a single bond, —O— or —OCO—, the compound has large HTP and good compatibility, and the compound has good stability.

$Y^{k1}$ is a single bond or —$(CH_2)_n$—, and n is an integer from 1 to 20.

Preferred examples include a single bond, —$CH_2CH_2$—, —$(CH_2)_4$— or —$(CH_2)_6$—, and HTP tends to be larger as n is smaller and compatibility tends to be better as n is larger.

$Z^{k1}$ is a single bond or alkylene having 1 to 10 carbons, at least one of —$CH_2$— in the alkylene may be replaced by —O—, —COO—, —OCO—, —CH=CH—, —CF=CF— or —C≡C—, and at least one of hydrogen may be replaced by halogen.

Preferred examples include a single bond, —COO—, —OCO—, alkylene having 1 to 10 carbons, —$CH_2O$—, —$OCH_2$—, —$CF_2O$— or —$OCF_2$—, and a balance between HTP and compatibility is good.

Then, mk1 is an integer from 2 to 4. A compound having mk1 of 2 has a low melting point and good compatibility. Moreover, a compound having mk1 of 3 or 4 tends to have large HTP.

Then, nk1 and nk2 are an integer from 0 to 2. A melting point tends to be high when nk is 0 and compatibility tends to be good when nk is 1 or 2.

A compound represented by general formula (K1) tends to have a higher melting point in comparison with a compound represented by general formula (K2). Moreover, a compound represented by general formula (K2) tends to have better compatibility and also slightly larger HIP in comparison with a compound represented by general formula (K1).

In addition, in "alkyl" described above, alkyl having 1 to 10 carbons is preferred, and alkyl having 1 to 6 carbons is further preferred. Specific examples of the alkyl is not particularly limited, but include methyl, ethyl, propyl, isopropyl, n-butyl, s-butyl, t-butyl, pentyl, hexyl and dodecanyl.

Specific examples of a preferred chiral compound include (K101) to (K130), and (K201) to (K220) described below.

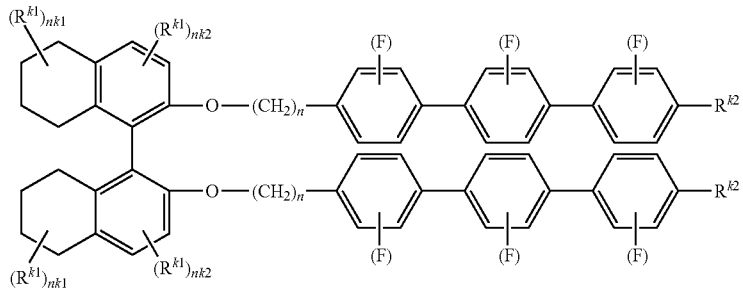

(K101)

-continued
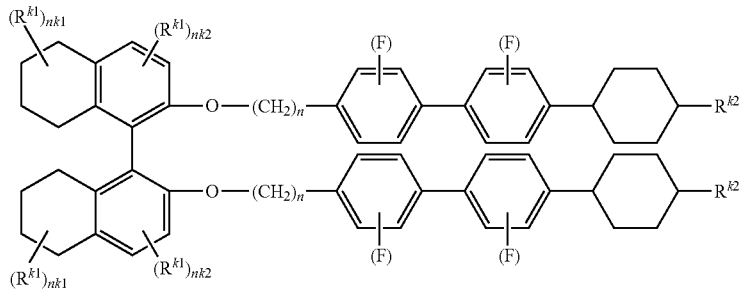
(K102)
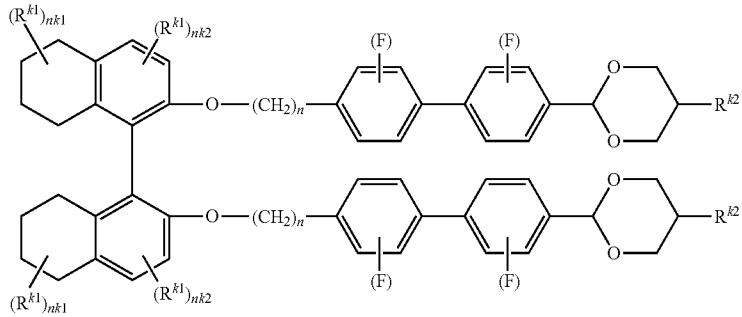
(K103)
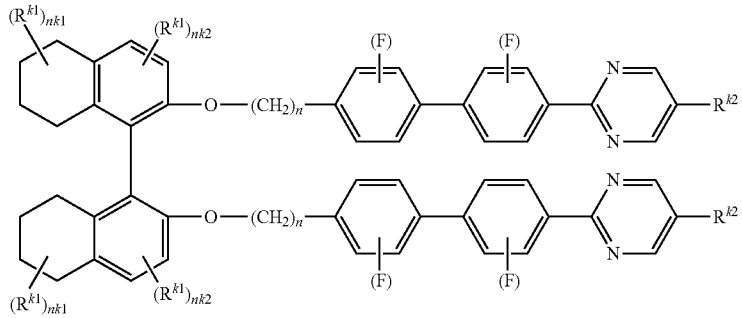
(K104)
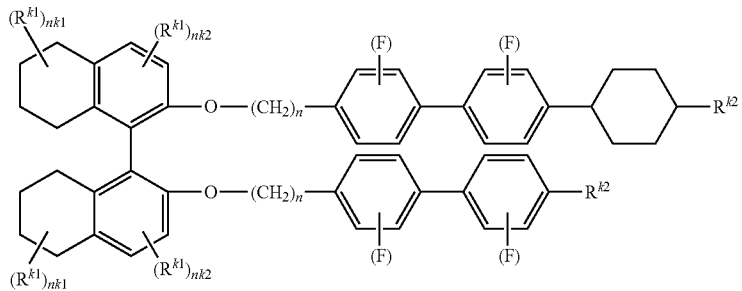
(K105)
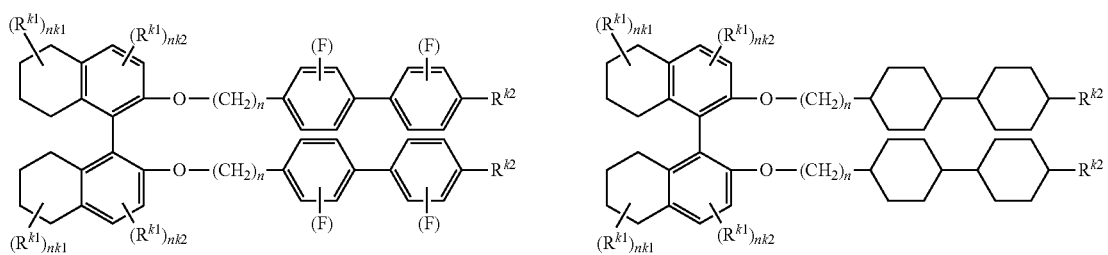
(K106) (K107)

-continued
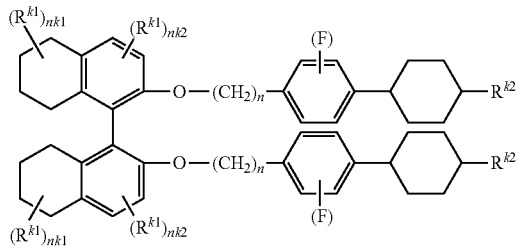
(K108)
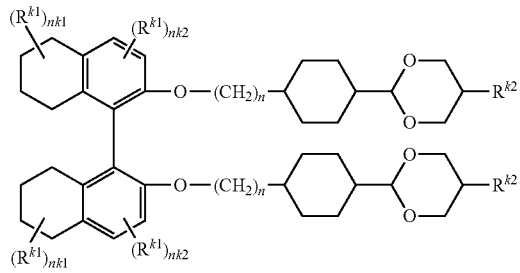
(K109)
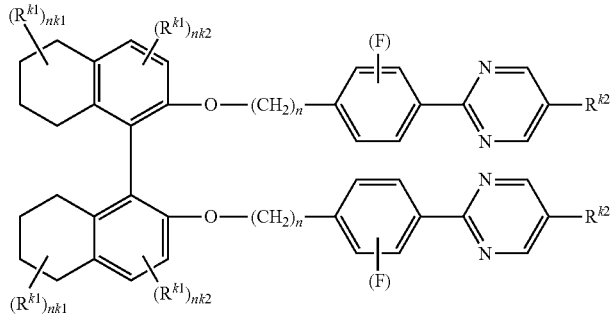
(K110)
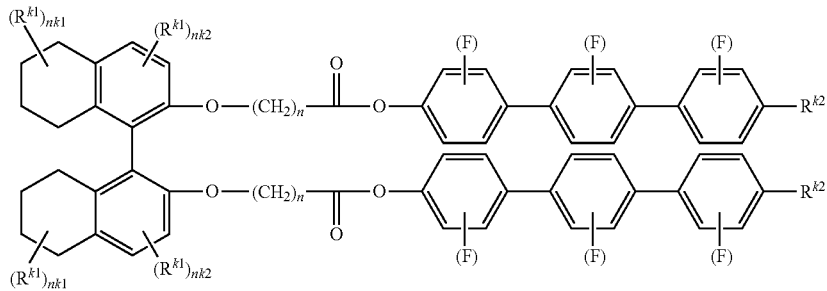
(K111)
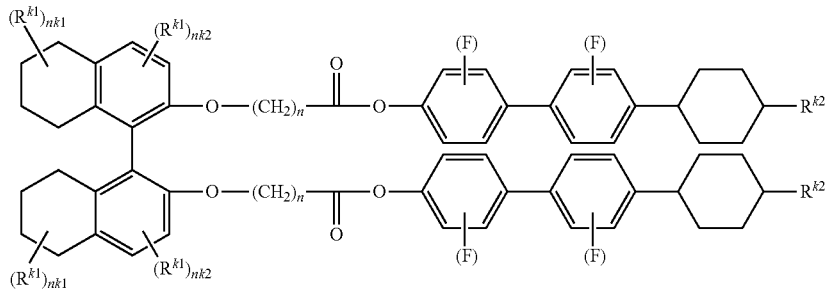
(K112)
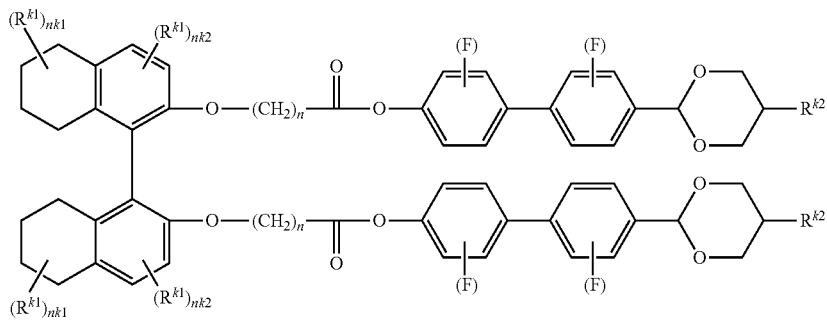
(K113)

-continued
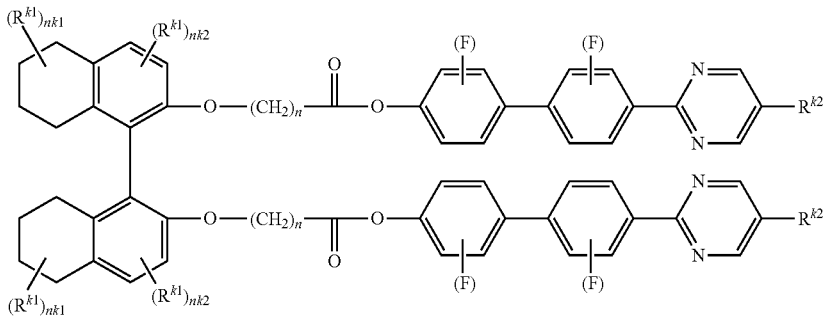
(K114)
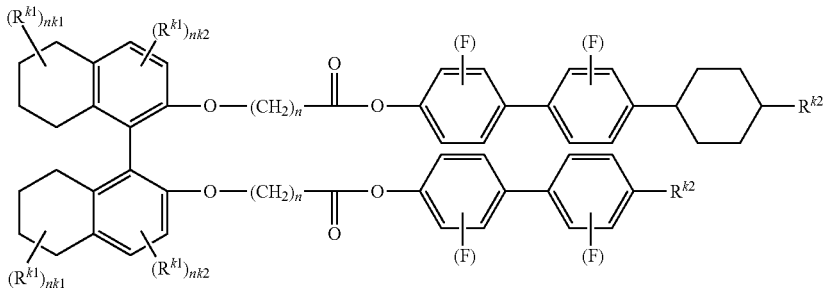
(K115)
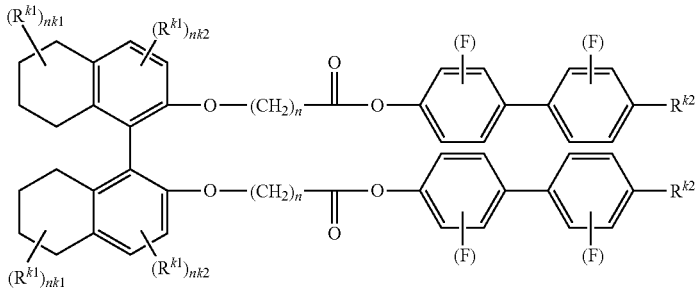
(K116)
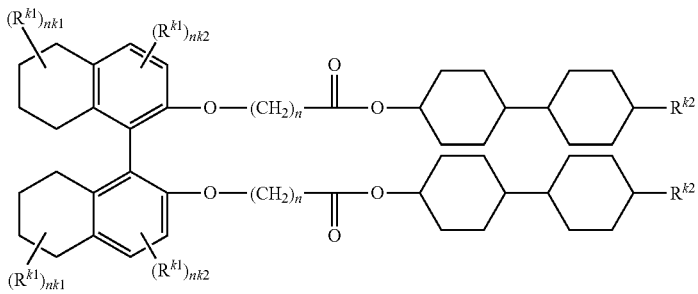
(K117)
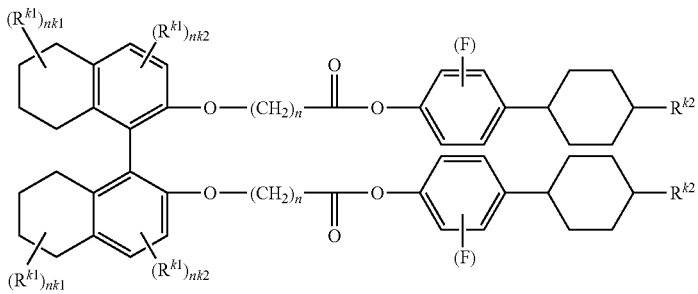
(K118)

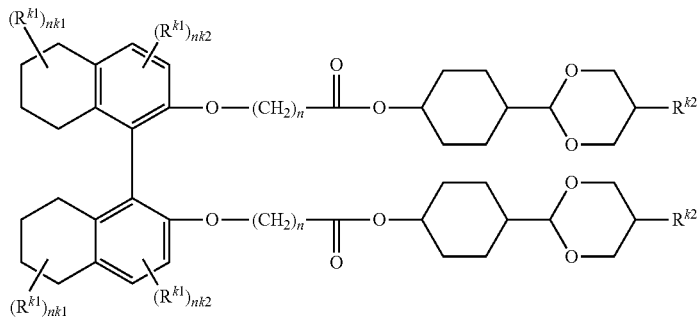
(K119)
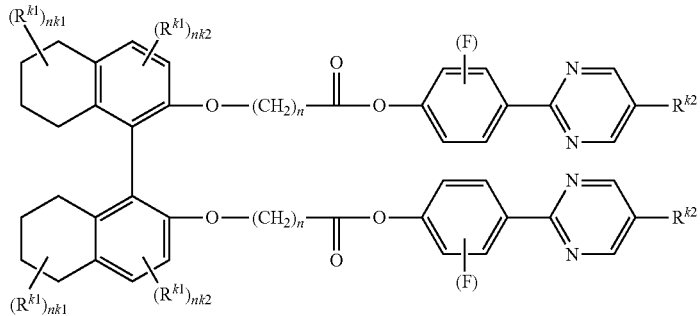
(K120)
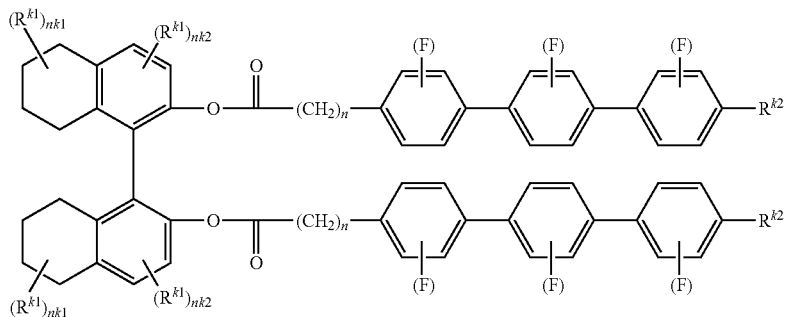
(K121)
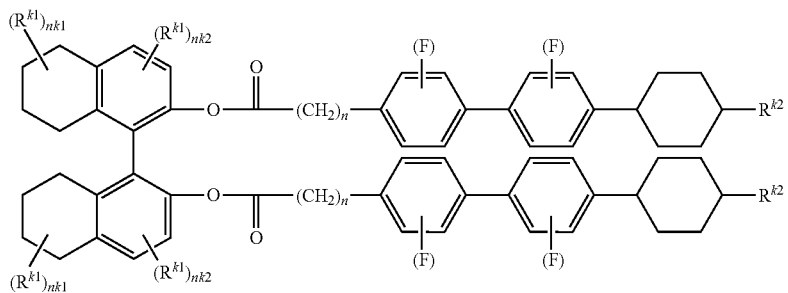
(K122)
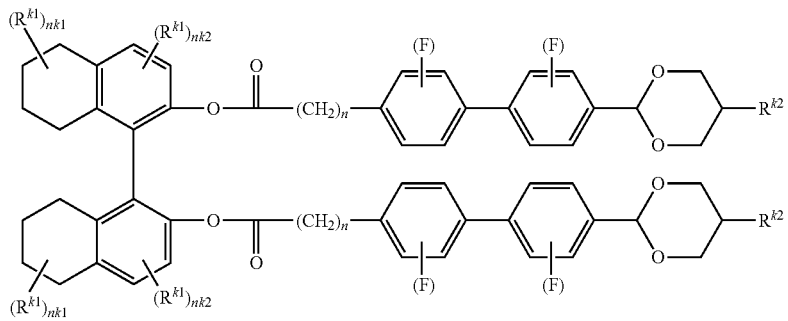
(K123)

-continued
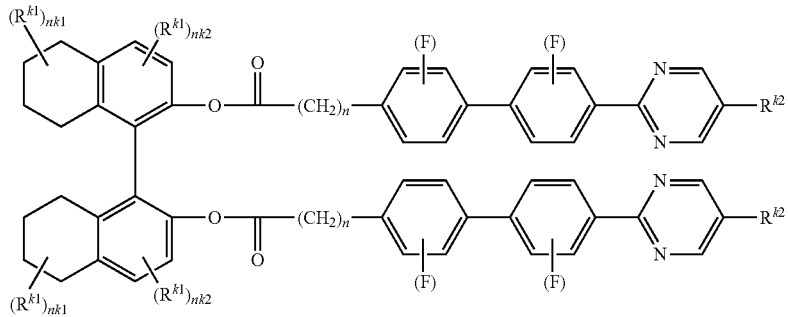
(K124)
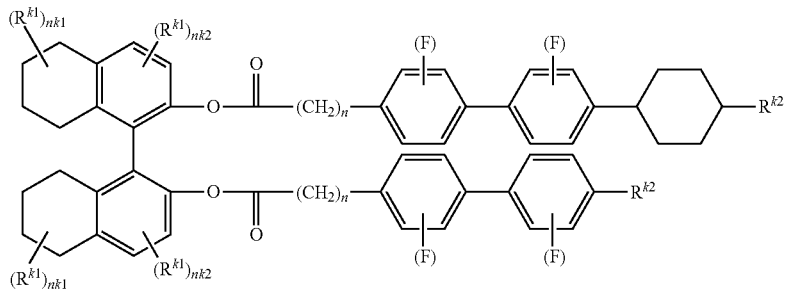
(K125)
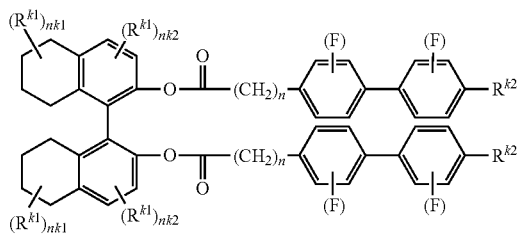
(K126)
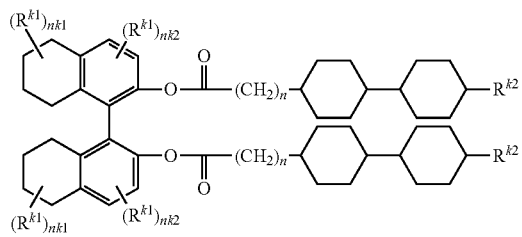
(K127)
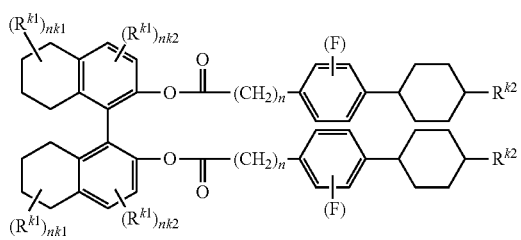
(K128)
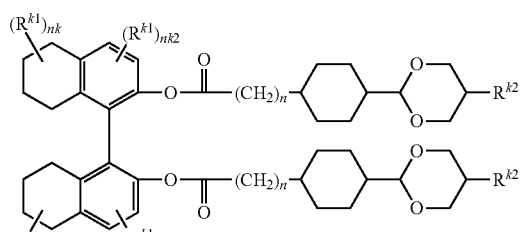
(K129)
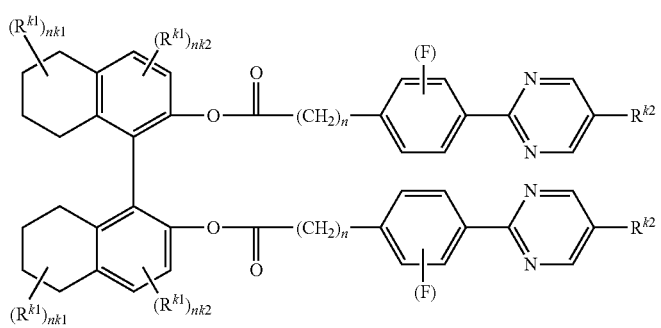
(K130)

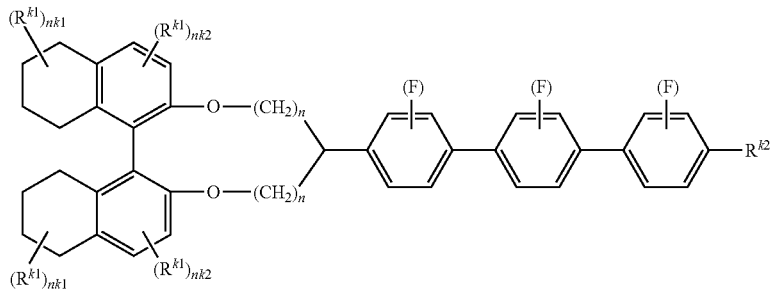
(K201)
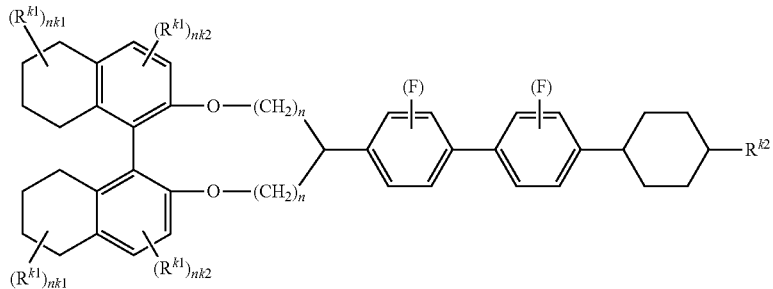
(K202)
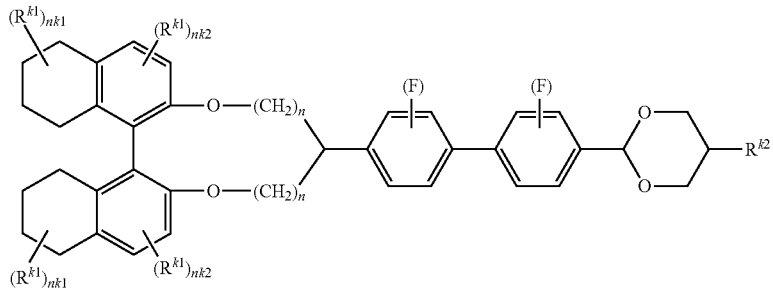
(K203)
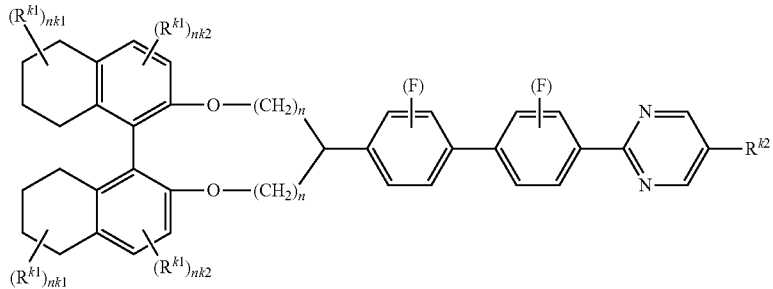
(K204)
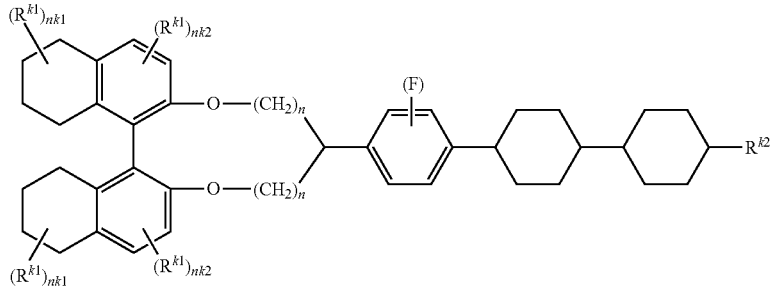
(K205)

-continued
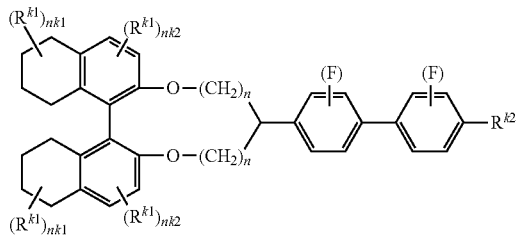
(K206)
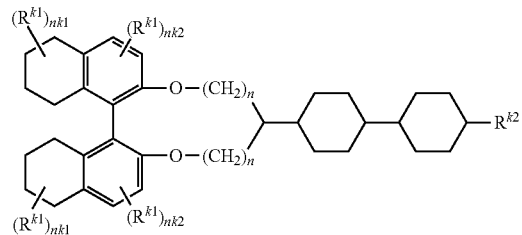
(K207)
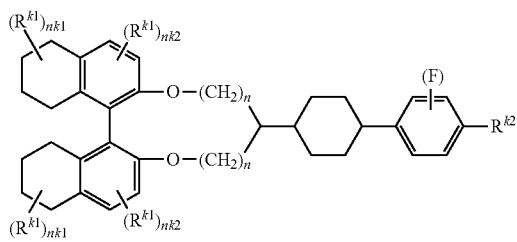
(K208)
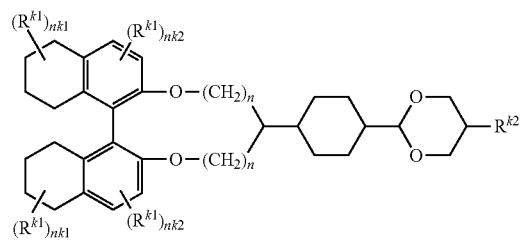
(K209)
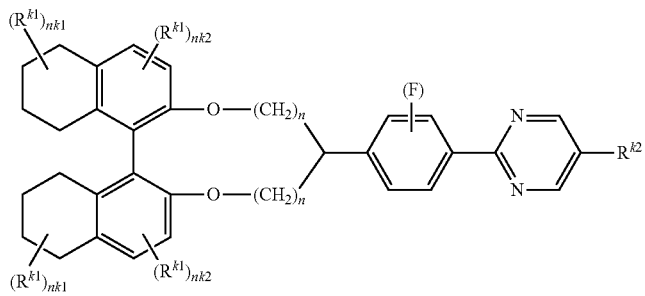
(K210)
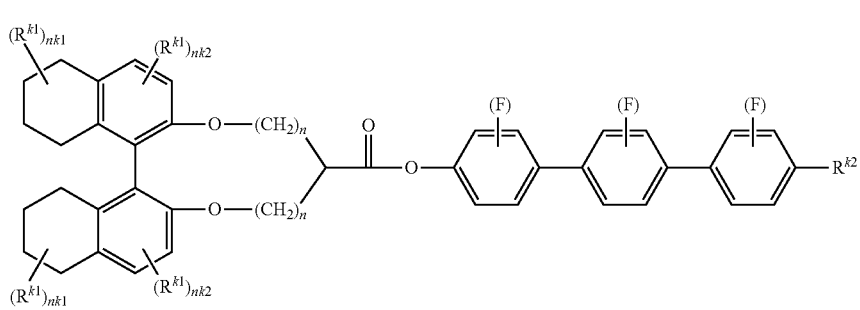
(K211)
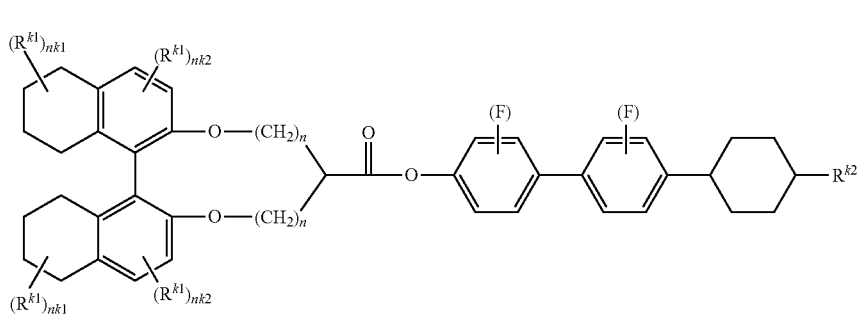
(K222)

-continued
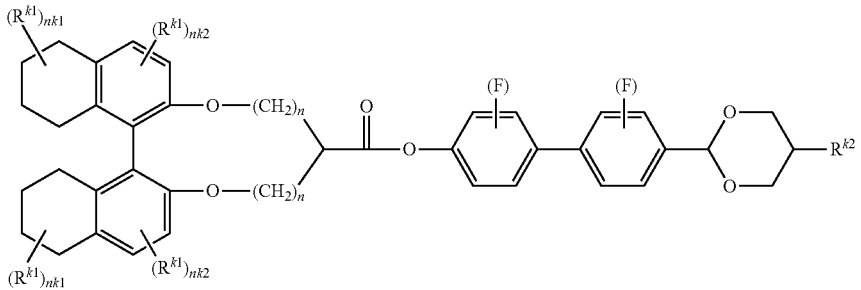
(K213)
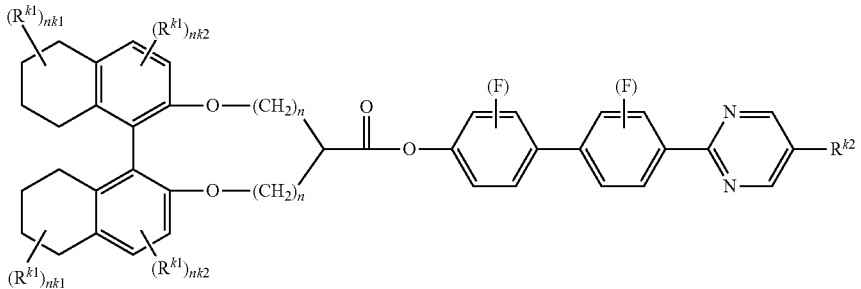
(K214)
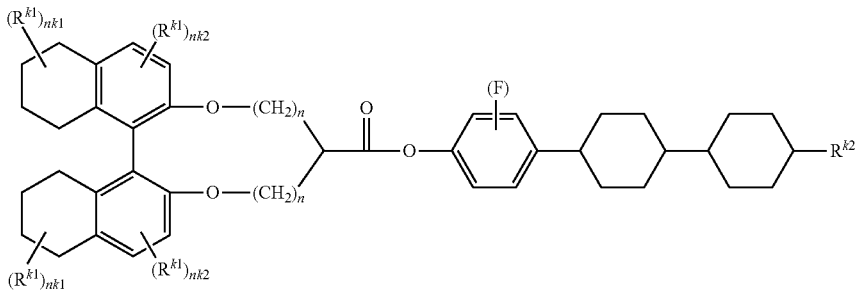
(K215)
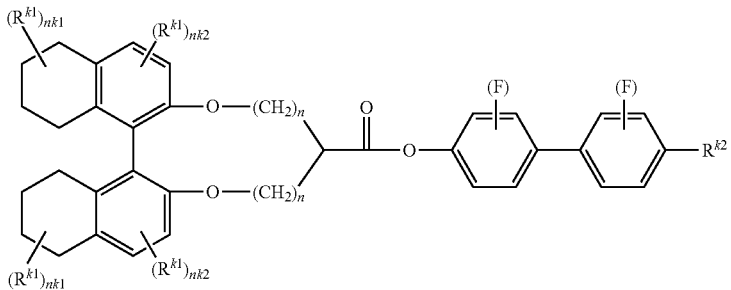
(K216)
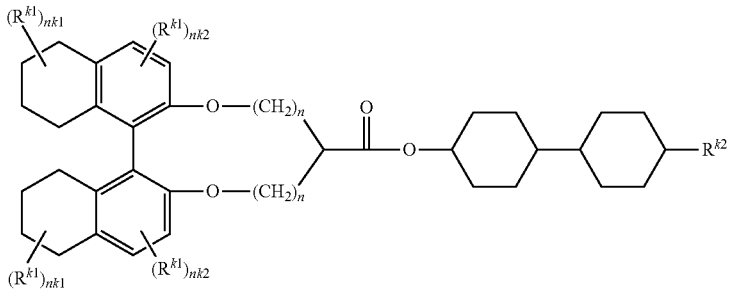
(K217)

-continued

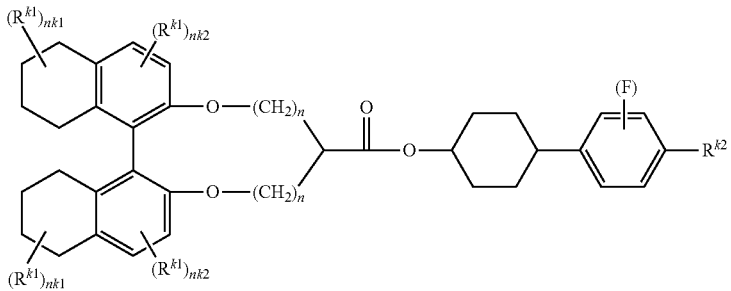
(K218)

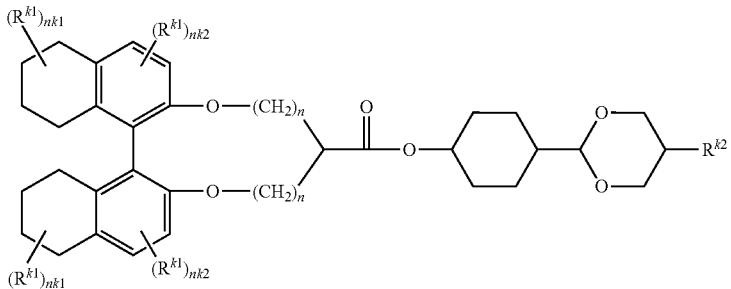
(K219)

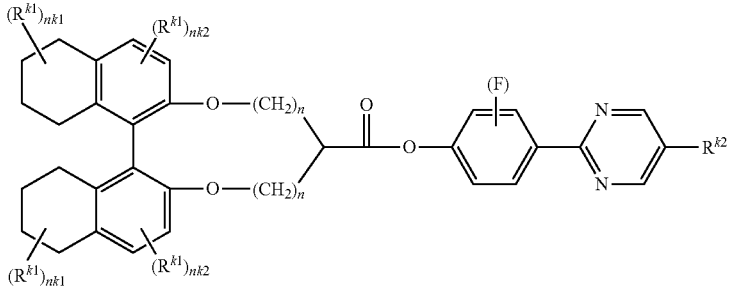
(K220)

(in formulas (K101) to (K130) and formulas (201) to (220), $R^{k1}$ is hydrogen, halogen, cyano, —SF$_5$, alkyl having 1 to 5 carbons in which at least one of hydrogen may be replaced by halogen, or alkoxy in which at least one of hydrogen may be replaced by halogen; $R^{k2}$ is hydrogen, halogen, cyano, —SF$_5$ or alkyl having 1 to 20 carbons;

n is an integer from 0 to 20; and nk1 and nk2 are an integer from 0 to 2;

partial structure formula (X1) or (X2) in which (F) is linked to 1,4-phenylene described below is 1,4-phenylene in which hydrogen may be replaced by one or two of fluorine; and when a plurality of $R^{k1}$, $R^{k2}$, nk1, nk2, n and partial structure formula (X1) or (X2) exist, the plurality each may be identical or different.)

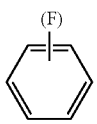
(X1)

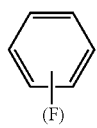
(X2)

In general, a content of the chiral agent in the optically isotropic liquid-crystal composition of the invention is preferably 1 to 20% by weight, and particularly preferably, 1 to 10% by weight. The liquid-crystal composition containing a chiral component in the range described above easily has the optically isotropic liquid-crystal phase.

Moreover, when the composition is used in a liquid-crystal display device, a concentration of the chiral component is adjusted, and thus neither diffraction nor reflection is preferably substantially found in a visible region.

In addition, the chiral compound constituting the chiral component contained in the liquid-crystal composition may include one kind or two or more kinds.

1.2.2 Synthesis of Chiral Compounds (K1) and (K2)

Next, synthesis of a compound represented by formula (K1) or (K2) will be described. Compounds (K1) and (K2) can be prepared by suitably combining methods in synthetic organic chemistry. Methods for introducing an objective terminal group, ring and bonding group into a starting material are described in Organic Synthesis (John Wiley & Sons, Inc.), Organic reactions (John Wiley & Sons, Inc.), Comprehensive Organic Synthesis (Pergamon Press), New Experimental Chemistry Course (Shin Jikken Kagaku Koza in Japanese) (Maruzen Co., Ltd.) and so forth.

A plurality of methods for preparing compounds (K1) and (K2) exist, and compounds (K1) and (K2) can be appropriate prepared with referring to Examples herein or books.

First, one example of a method for forming compound (15) being a common intermediate will be described using a scheme.

(1) Synthesis of Octahydro-Naphthol Derivative (15)

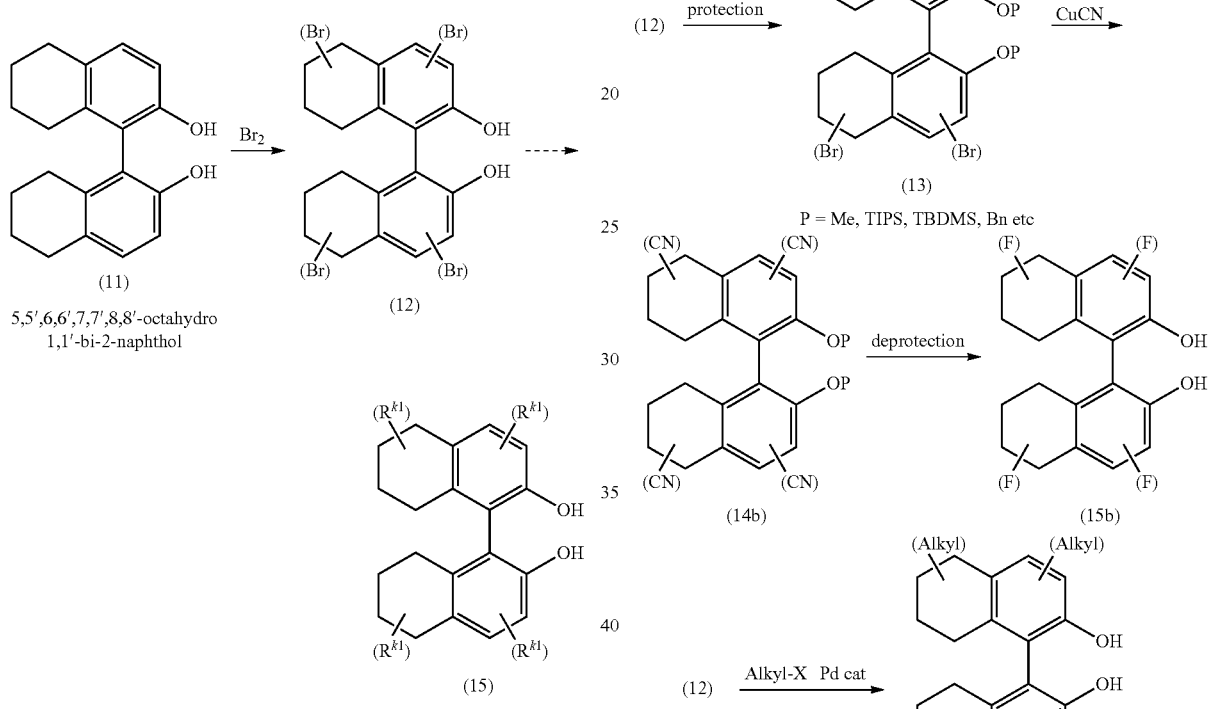

First, one example of the method for forming compound (15) will be described using the scheme. As chiral compound (11), both of (S) isomer and (R) isomer are commercially available. Compound (12) is obtained by acting bromine or a brominating agent on a compound. On the occasion, equivalence of bromine to be used is adjusted by the number of functional groups for use in replacement.

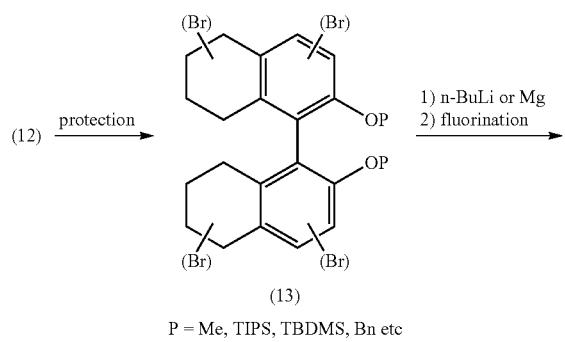

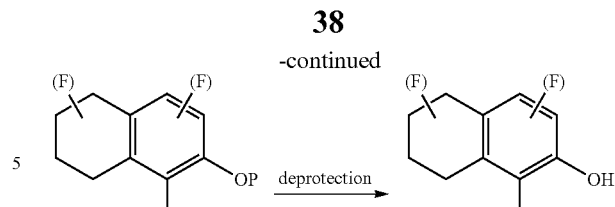

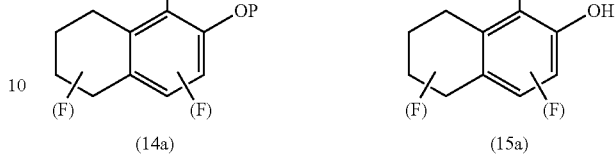

P = Me, TIPS, TBDMS, Bn etc

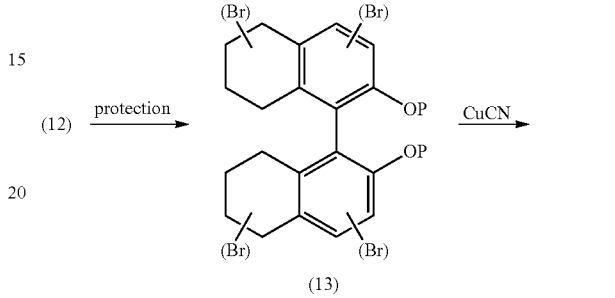

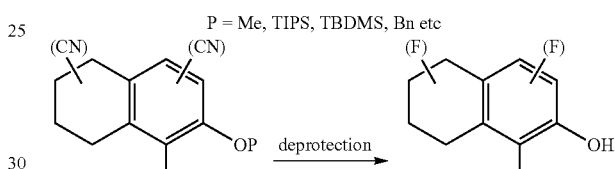

(i) Case where $R^{K1}$ is Fluorine

Compound (14a) is obtained by protecting compound (12) using a suitable protective group, and then acting a fluorinating agent such as n-BuLi and N-fluorobenzenesulfonimide thereon. Compound (15a) can be obtained by finally removing the protective group.

(ii) Case where $R^{K1}$ is —CN

Compound (14b) is obtained by protecting compound (12) using a suitable protective group, and then acting copper(II) cyanide or the like thereon. Compound (15b) can be obtained by finally removing the protective group.

(iii) Case where $R^{K1}$ is Alkyl or Alkenyl

Compound (15c) can be obtained by acting, in the present of a base such as potassium carbonate and a palladium catalyst, alkyl halide or alkenyl halide on compound (12) to perform a cross-coupling reaction.

(iv) Method for Preparing Compound (K1)

Compounds (K1) and (K2) can be derived from compound (15) by using compound (15) as a starting compound and combining general organic synthesis techniques. One example is shown below.

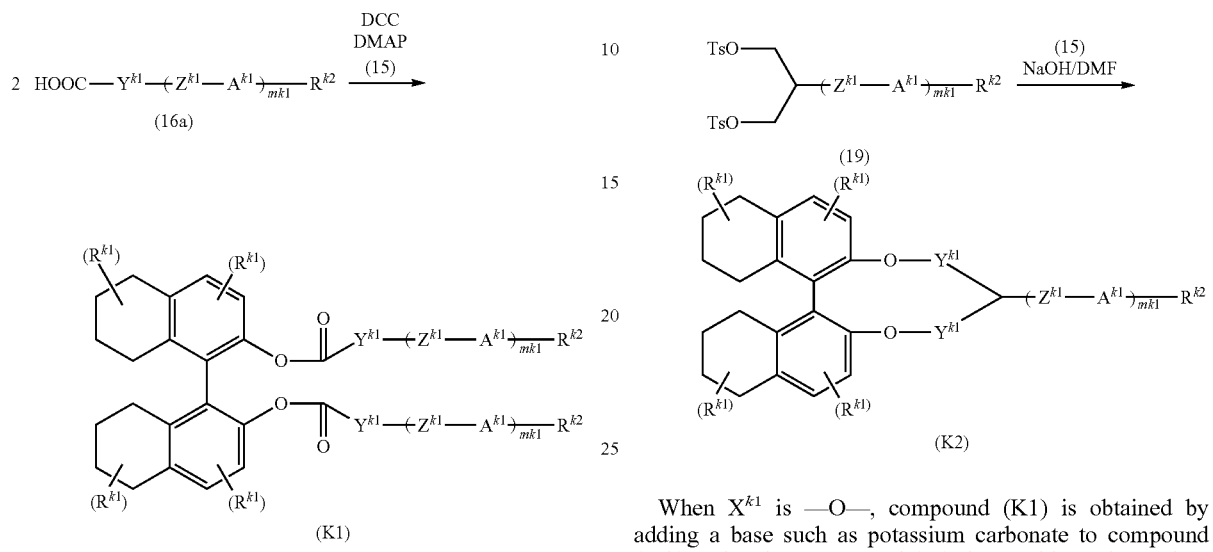

When $X^{k1}$ is —OCO—, compound (K1) is obtained by adding N,N'-dicyclohexylcarbodiimide (DCC) and 4-dimethylaminopyridine (DMAP) to compound (16a) and acting compound (15) the resulting mixture.

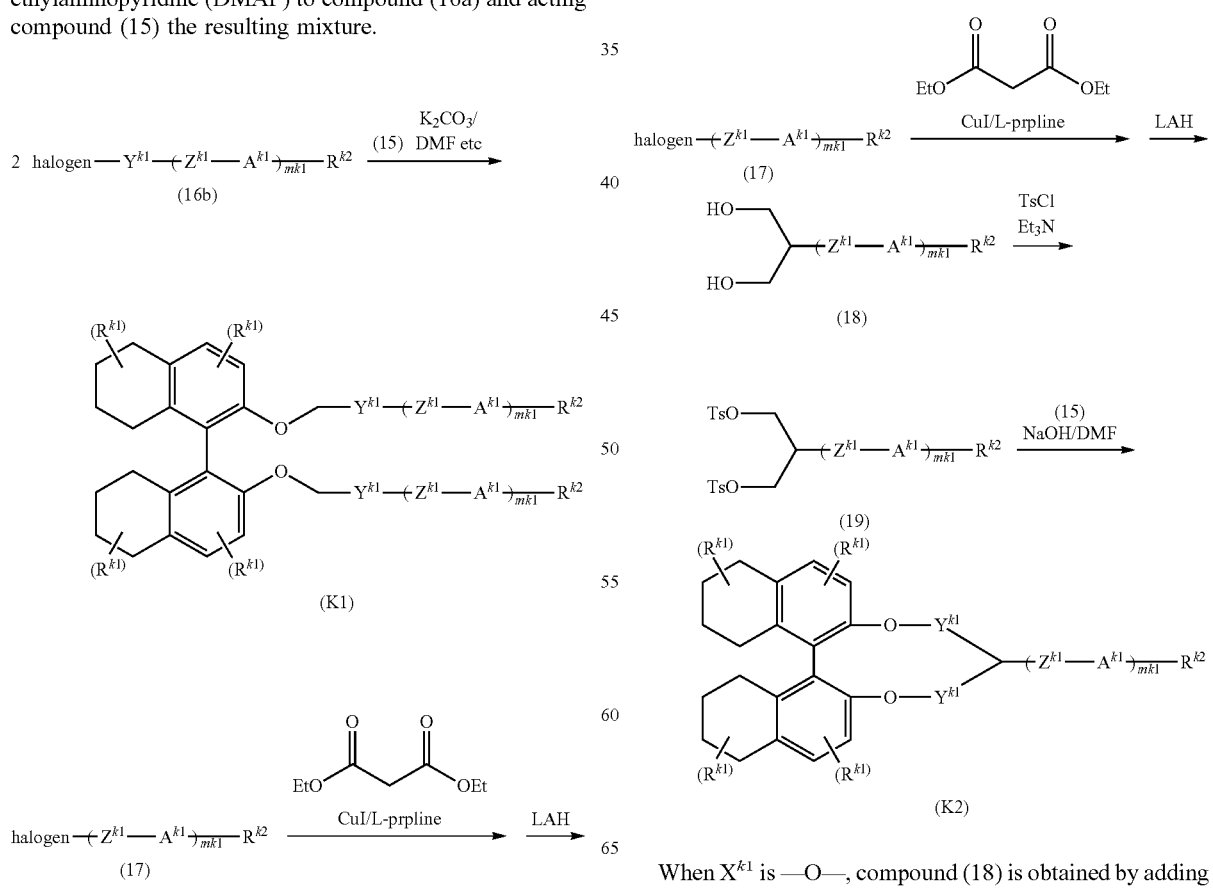

When $X^{k1}$ is —O—, compound (K1) is obtained by adding a base such as potassium carbonate to compound (16b) and acting compound (15) the resulting mixture in a solvent such as N,N-dimethylformamide (DMF).

(v) Method for Preparing Compound (K2)

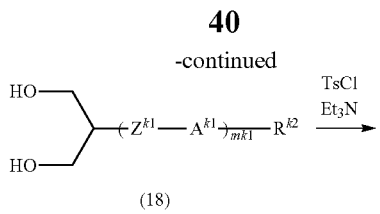

When $X^{k1}$ is —O—, compound (18) is obtained by adding a base such as diethyl malonate, copper iodide, L-proline and cesium carbonate to compound (17) to obtain a malonic acid derivative, and then acting a reducing agent such as lithium aluminum hydride (LAH) thereon. Then, compound (K2) is obtained by adding a base to compound (19) obtained by converting compound (18) into a tosyl isomer, and then acting compound (15) the resulting mixture.

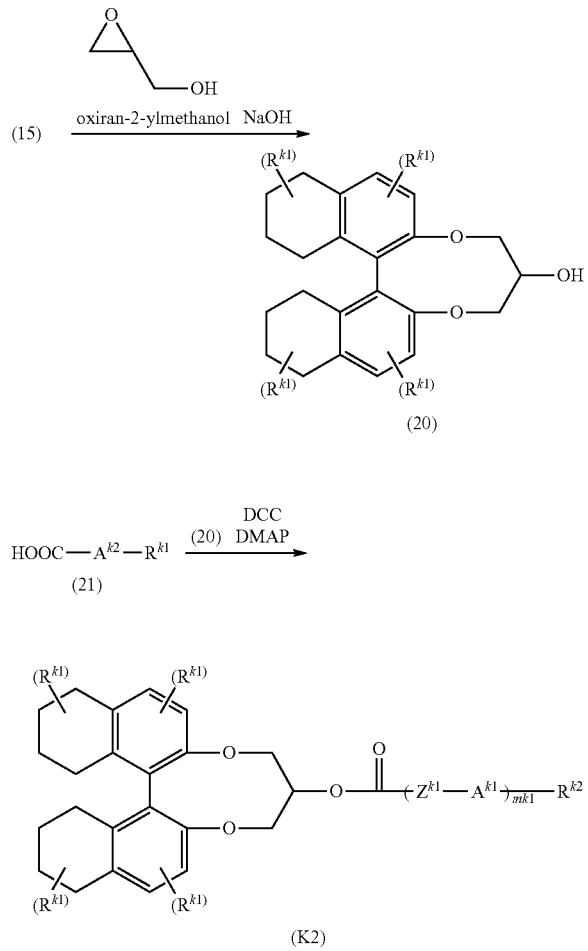

When $X^{k1}$ is —O— and $Z^{k1}$ is —OCO—, compound (20) is obtained by adding a base to compound (15), and act the resulting product on an oxirane derivative or the like. Then, compound (K2) is obtained by adding dicyclohexylcarbodiimide (DCC) and dimethylaminopyridine (DMAP) to compound (21) and acting compound (20) on the resulting mixture.

Next, one example of a method for forming bonding group $Z^{k1}$ will be described using a scheme. In the scheme, $MSG_1$ or $MSG_2$ is a monovalent organic group having at least one ring. A plurality of MSG1 (or MSG2) used in the scheme may be identical or different. Compounds (1A) to (1K) correspond to compound (K1) or (K2).

(I) Formation of a Single Bond

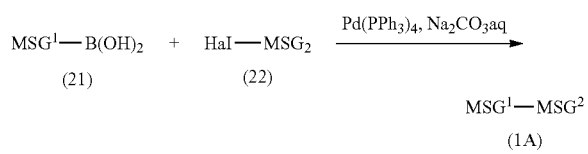

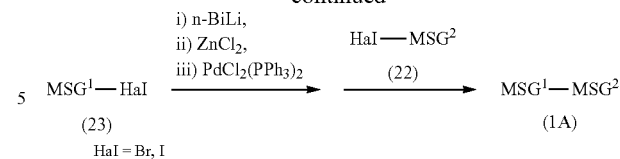

Compound (1A) is prepared by allowing aryl boronic acid (21) to react, in the presence of an aqueous carbonate solution and a catalyst such as tetrakis(triphenylphosphine)palladium, with compound (22) prepared according to a publicly known method. The compound (1A) is also prepared by allowing compound (23) prepared according to a publicly known method to react with n-butyllithium and subsequently with zinc chloride, and further with compound (22) in the presence of a catalyst such as dichlorobis (triphenylphosphine)palladium.

(II) Formation of —$CF_2O$— and —$OCF_2$—

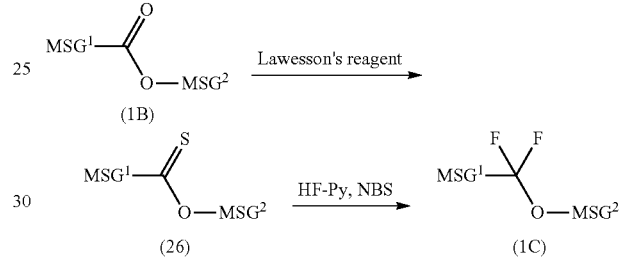

Compound (26) is obtained by treating compound (1B) with a thiation reagent such as Lawesson's reagent. Compound (1C) having —$CF_2O$— is prepared by fluorinating compound (26) with a hydrogen fluoride-pyridine complex and N-bromosuccinimide (NBS) (refer to M. Kuroboshi et al., Chem. Lett., 1992, 827). Compound (1C) is also prepared by fluorinating compound (26) with (diethylamino)sulfur trifluoride (DAST) (refer to W. H. Bunnelle et al., J. Org. Chem. 1990, 55, 768). A compound having —$OCF_2$— can also be prepared according to the method. The bonding groups can also be formed according to the method described in Peer. Kirsch et al., Angew. Chem. Int. Ed. 2001, 40, 1480.

(III) Formation of —CH=CH—

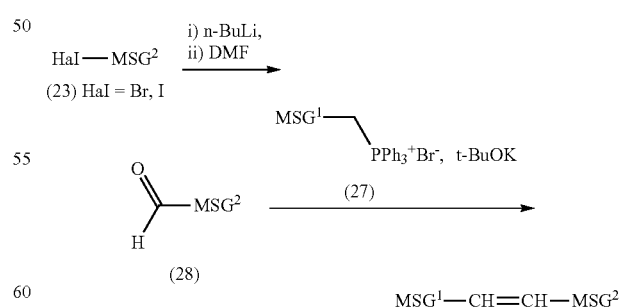

Aldehyde (28) is obtained by treating compound (23) with n-butyllithium, and then allowing the treated product to react with formamide such as N,N-dimethylformamide (DMF). Compound (1D) is prepared by allowing phosphorus ylide generated by treating phosphonium salt (27) prepared according to a publicly known method with a base such as potassium t-butoxide to react with aldehyde (28). A cis isomer is generated depending on reaction conditions, and therefore the cis isomer is isomerized into a trans isomer according to a publicly known method, when necessary.

(IV) Formation of —(CH$_2$)$_2$—

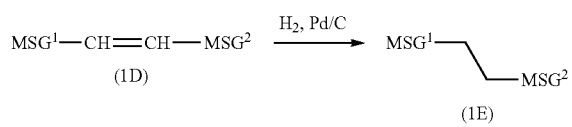

Compound (1E) is prepared by hydrogenating compound (1D) in the presence of a catalyst such as palladium on carbon.

(V) Formation of —(CH$_2$)$_4$—

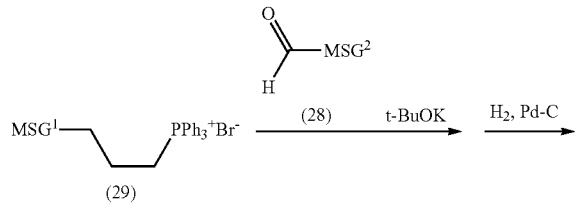

A compound having —(CH$_2$)$_2$— and —CH=CH— is obtained by using phosphonium salt (29) in place of phosphonium salt (27) according to the method described in section (III) or section (IV). Compound (1F) is prepared by catalytically hydrogenating the resulting compound.

(VI) Formation of —C≡C—

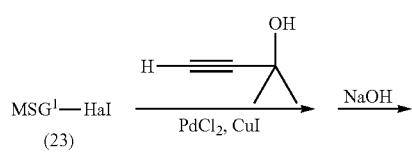

Compound (30) is obtained by allowing compound (23) to react with 2-methyl-3-butyn-2-ol in the presence of a catalyst including dichloropalladium and copper halide, and then performing deprotection under basic conditions. Compound (1G) is prepared by allowing compound (30) to react with compound (22) in the presence of a catalyst including dichloropalladium and copper halide.

(VII) Formation of —CF=CF—

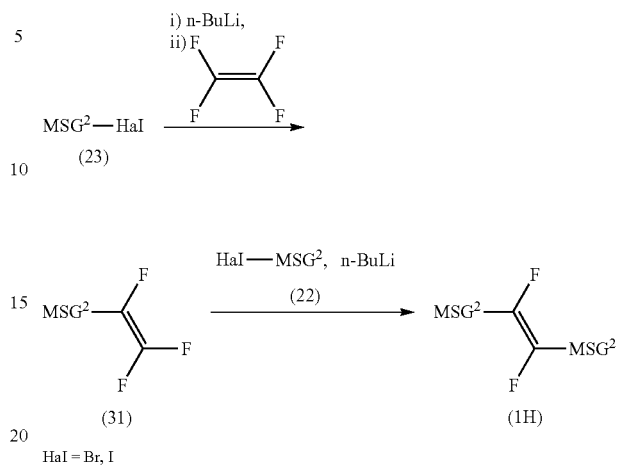

Compound (31) is obtained by treating compound (23) with n-butyllithium, and then allowing the treated product to react with tetrafluoroethylene. Compound (1H) is prepared by treating compound (22) with n-butyllithium, and then allowing the treated product to react with compound (31).

(VIII) Formation of —CH$_2$O— or —OCH$_2$—

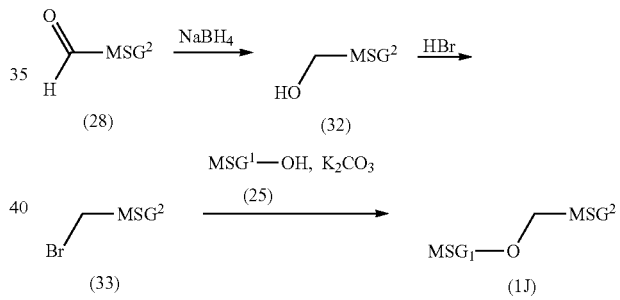

Compound (32) is obtained by reducing compound (28) with a reducing agent such as sodium boron hydride. Compound (33) is obtained by halogenating compound (32) with hydrobromic acid or the like. Compound (1J) is prepared by allowing compound (33) to react with compound (25) in the presence of potassium carbonate or the like.

(IX) Formation of —(CH$_2$)$_3$O— or —O(CH$_2$)$_3$—

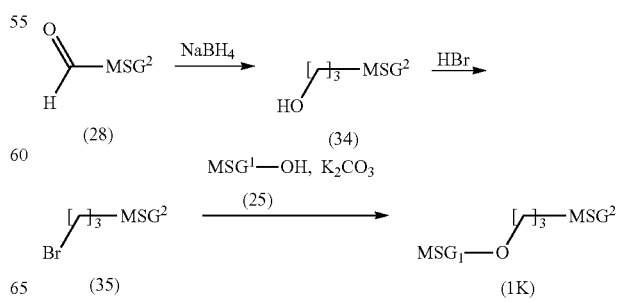

Compound (1K) is prepared by using compound (34) in place of compound (32) according to the method described in section (VIII).

(X) Formation of —(CF$_2$)$_2$—

According to the method described in "J. Am. Chem. Soc., 2001, 123, 5414," a compound having —(CF$_2$)$_2$— is obtained by fluorinating diketone (—COCO—) with sulfur tetrafluoride in the presence of a hydrogen fluoride catalyst.

1.3 Achiral Liquid-Crystal Component

An achiral liquid-crystal component constituting the liquid-crystal composition or the optically isotropic liquid-crystal composition according to the invention is a liquid-crystal composition by preparing one or more kinds of compounds to exhibit the liquid-crystal phase. An achiral liquid-crystal component containing one or more kinds of compounds represented by formula (1-A) is suitable as the liquid-crystal component used as in the form of the liquid-crystal device.

1.3.1 Compound (1-A)

Ring $A^{11}$, ring $A^{12}$, ring $A^{13}$ and ring $A^{14}$ are independently 1,4-phenylene, 1,3-dioxane-2,5-diyl, tetrahydropyran-2,5-diyl, tetrahydropyran-3,6-diyl, pyrimidine-2,5-diyl, naphthalene-2,6-diyl or bicyclo[2,2,2]octane-1,4-diyl, and at least one of hydrogen in the rings may be replaced by halogen.

Ring $A^{11}$, ring $A^{12}$, ring $A^{13}$ and ring $A^{14}$ are each independently preferably 1,4-phenylene in which hydrogen may be replaced by halogen, 1,3-dioxane-2,5-diyl, tetrahydropyran-2,5-diyl or 1,4-cyclohexylene.

$Z^{11}$, $Z^{12}$, $Z^{13}$ and $Z^{14}$ are independently a single bond or alkylene having 1 to 4 carbons, at least one of —CH$_2$— in the alkylene may be replaced by —O—, —S—, —COO—, —OCO—, —CF$_2$O—, —OCF$_2$—, —CH=CH—, —CF=CF— or —C≡C—, and at least one of hydrogen in the alkylene may be replaced by halogen.

$Z^{11}$, $Z^{12}$, $Z^{13}$ and $Z^{14}$ are preferably a single bond, —CH$_2$CH$_2$—, —CH=CH—, —C≡C—, —COO—, —CF$_2$O—, —OCF$_2$—, —CH$_2$O— or —OCH$_2$—, and above all, a single bond, —COO— or —CF$_2$O— is preferred.

Moreover, in the bonds, in a bonding group having a double bond, such as —CH=CH—, —CF=CF—,

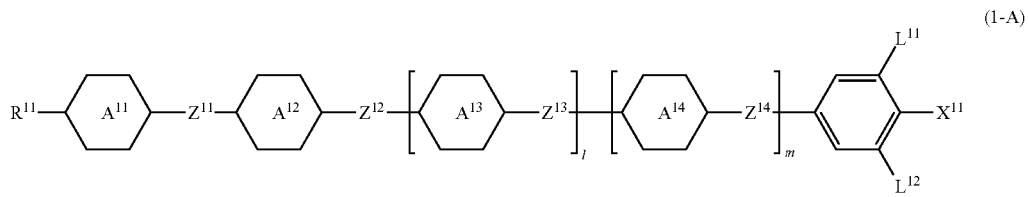

In formula (1-A) above, $R^{11}$ is hydrogen or alkyl having 1 to 20 carbons, at least one of —CH$_2$— in the alkyl may be replaced by —O—, —S—, —COO—, —OCO— or —C≡C—, and at least one of hydrogen in the alkyl may be replaced by halogen.

In such $R^{11}$, alkyl having 1 to 10 carbons and alkenyl having 2 to 10 carbons are preferred. Alkyl having 2 to 8 carbons and alkenyl having 2 to 8 carbons are further preferred. A preferred configuration of —CH=CH— in the alkenyl depends on a position of a double bond. A trans configuration is preferred in the alkenyl having the double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$. A cis configuration is preferred in the alkenyl having the double bond in an even-numbered position, such as —CH$_2$CH=CHCH$_3$, —CH$_2$CH=CHC$_2$H$_5$ and —CH$_2$CH=CHC$_3$H$_7$. An alkenyl compound having the preferred configuration has a high maximum temperature or a wide temperature range of the liquid-crystal phase. Detailed explanation is found in Mol. Cryst. Liq. Cryst., 1985, 131, 109 and Mol. Cryst. Liq. Cryst., 1985, 131, 327.

—CH=CH—(CH$_2$)$_2$— and —(CH$_2$)$_2$—CH=CH—, with regard to a configuration, trans is preferred to cis.

$L^{11}$ and $L^{12}$ are each independently hydrogen or halogen. Above all, $L^{11}$ and $L^{12}$ are each independently preferably hydrogen or fluorine.

$X^{11}$ is halogen, —C≡N, —N=C=S, —C≡C—C≡N, —SF$_5$, —CHF$_2$, —CF$_3$, —CF$_2$CH$_2$F, —CF$_2$CHF$_2$, —CF$_2$CF$_3$, —(CF$_2$)$_3$—F, —CF$_2$CHFCF$_3$, —CHFCF$_2$CF$_3$, —(CF$_2$)$_4$—F, —(CF$_2$)$_5$—F, —OCHF$_2$, —OCF$_3$, —OCF$_2$CH$_2$F, —OCF$_2$CHF$_2$, —OCH$_2$CF$_3$, —OCF$_2$CF$_3$, —O—(CF$_2$)$_3$—F, —OCF$_2$CHFCF$_3$, —OCHFCF$_2$CF$_3$, —O—(CF$_2$)$_4$—F, —O—(CF$_2$)$_5$—F, —CH=CF$_2$, —CH=CHCF$_3$ or —CH=CHCF$_2$CF$_3$.

Specific examples of preferred $X^{11}$ include fluorine, chlorine, —C≡N, —N=C=S, —CF$_3$, —CHF$_2$, —OCF$_3$ and —OCHF$_2$. Specific examples of most preferred $X^{11}$ include fluorine, chlorine, —C≡N, —N=C=S, —CF$_3$ and —OCF$_3$.

Then, l and m are independently 0 or 1.

The compound represented by formula (1-A) above particularly preferably includes compounds represented by formulas (1-A-01) to (1-A-16) below.

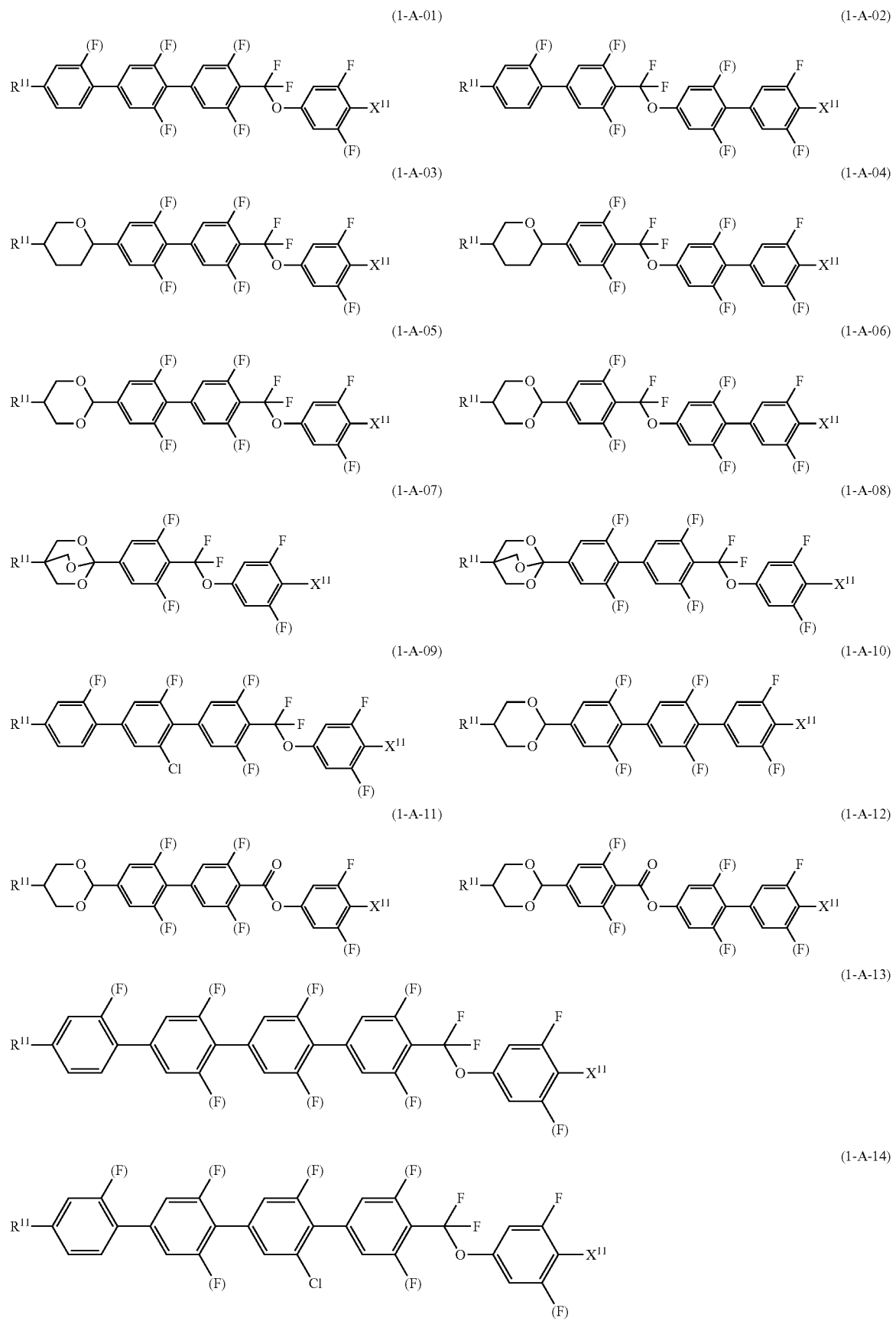

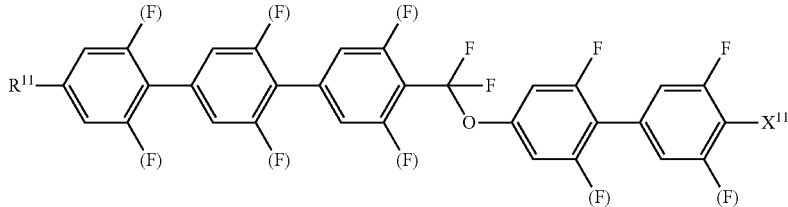

(1-A-15)

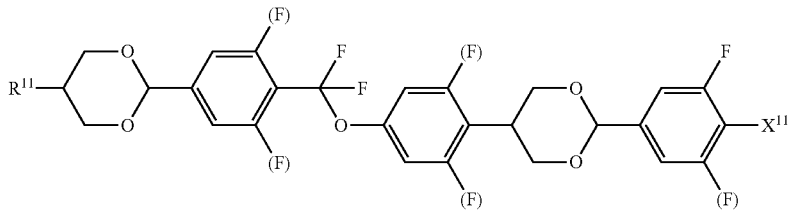

(1-A-16)

(In formulas (1-A-01) to (1-A-16), $R^{11}$ is hydrogen or alkyl having 1 to 8 carbons, $X^{11}$ is fluorine, chlorine, —C≡N, —CF$_3$, —CHF$_2$, —CH$_2$F, —OCF$_3$, —OCHF$_2$, —OCH$_2$F or —C≡C—CF$_3$, and (F) is hydrogen or fluorine.)

1.3.2 Properties of Compound (1-A)

A combination of l, m, n and o, a kind of rings $A^{11}$ to $A^{14}$, left-terminal group $R^{11}$, right-terminal group $X^{11}$, a group on a phenylene ring at a terminal and a replacement position thereof ($L^{11}$ and $L^{12}$), bonding groups $Z^{11}$ to $Z^{14}$ and so forth in compound (1-A) are suitably selected to allow adjustment of physical properties such as a clearing point, refractive index anisotropy and dielectric anisotropy of liquid-crystal component A.

A general relationship between physical properties of compound (1-A), and a combination of l and m, rings $A^{11}$ to $A^{14}$, left-terminal group $R^{11}$, right-terminal group $X^{11}$, bonding groups $Z^{11}$ to $Z^{14}$, and a kind of $L^{11}$ and $L^{12}$ will be described below.

In general, as (l+m) is larger, a clearing point of compound (1-A) is higher, and as (l+m) is smaller, a melting point of compound (1-A) is lower.

In general, as a larger amount of an aromatic ring is contained in rings $A^{11}$ to $A^{14}$, refractive index anisotropy of compound (1-A) becomes larger. Then, 1,4-phenylene in which at least one of hydrogen is replaced by halogen, pyrimidine-2,5-diyl, pyridine-2,5-diyl, tetrahydropyran-2,5-diyl, tetrahydropyran-3,6-diyl or 1,3-dioxane-2,5-diyl is effective in exhibiting large dielectric anisotropy, and a 1,4-cyclohexylene ring or a tetrahydropyran-2,5-diyl ring contributes to exhibition of good compatibility of compound (1-A).

In general, when $R^{11}$ has a straight chain, a temperature range of a liquid-crystal phase of compound (1-A) is wide and viscosity becomes small. On the other hand, when $R^{11}$ has a branched chain, compound (1-A) has good compatibility with other liquid-crystal compounds.

In general, when bonding groups $Z^{11}$, $Z^{12}$, $Z^{13}$ and $Z^{14}$ are each a single bond, —CH$_2$CH$_2$—, —CH=CH—, —CF$_2$O—, —OCF$_2$—, —CH$_2$O—, —OCH$_2$—, —CF=CF—, —(CH$_2$)$_3$—O—, —O—(CH$_2$)$_3$—, —(CH$_2$)$_2$—CF$_2$O—, —OCF$_2$—(CH$_2$)$_2$— or —(CH$_2$)$_4$—, viscosity of compound (1-A) is small. Moreover, in general, when bonding groups $Z^{11}$, $Z^{12}$, $Z^{13}$ and $Z^{14}$ are each a single bond, —(CH$_2$)$_2$—, —CF$_2$O—, —OCF$_2$— or —CH=CH—, viscosity of compound (1-A) becomes smaller. In general, when bonding groups $Z^{11}$, $Z^{12}$, $Z^{13}$ and $Z^{14}$ are each —C≡C—, refractive index anisotropy of compound (1-A) is large. In general, when a bonding group is —COO— or —CF$_2$O—, dielectric anisotropy of compound (1-A) is large. In general, when $Z^{11}$, $Z^{12}$, $Z^{13}$ and $Z^{14}$ are a single bond, —(CH$_2$)$_2$—, —CH$_2$O—, —CF$_2$O—, —OCF$_2$— or —(CH$_2$)$_4$—, compound (1-A) is relatively chemically stable, and hard to cause deterioration.

In general, when $X^{11}$ the refractive index anisotropy or the dielectric anisotropy is large, the liquid-crystal device of the invention tends to have a low voltage, and when the viscosity is low, a response speed becomes high.

In general, when $X^{11}$ is fluorine, chlorine, —C≡N, —N=C=S, —SF$_5$, —CF$_3$, —CHF$_2$, —CH$_2$F, —OCF$_3$, —OCHF$_2$ or —OCH$_2$F, the dielectric anisotropy of compound (1-A) is large. Moreover, in general, when $X^{11}$ is —C≡N or —N=C=S, optical anisotropy of compound (1-A) is large. When $X^{11}$ is fluorine, —OCF$_3$ or alkyl, compound (1-A) is chemically stable.

In general, when both $L^{11}$ and $L^{12}$ are fluorine and $X^{11}$ is fluorine, chlorine, —C≡N, —N=C=S, —SF$_5$, —CF$_3$, —CHF$_2$, —CH$_2$F, —OCF$_3$, —OCHF$_2$ or —OCH$_2$F, the dielectric anisotropy of compound (1-A) is large. Moreover, in general, when $L^{11}$ is fluorine and $X^{11}$ is —CF$_3$ or —OCF$_3$, both $L^{11}$ and $L^{12}$ are fluorine, and when $X^{11}$ is —CF$_3$ or —OCF$_3$, or when all of $L^{11}$, $L^{12}$ and $X^{11}$ are fluorine, compound (1-A) has a large dielectric anisotropy value and a wide temperature range of the liquid-crystal phase, and further, compound (1-A) is chemically stable, and hard to cause deterioration.

2 Mixture Containing Optically Isotropic Liquid-Crystal Composition and Polymerizable Monomer, and Polymer-Liquid-Crystal Composite Material A second embodiment of the invention includes a mixture containing an optically isotropic liquid-crystal composition and a polymerizable monomer. Moreover, a third embodiment of the invention includes an optically isotropic polymer-liquid-crystal composite material. For example, the material can be manufactured by performing a polymerization reaction in the mixture containing the optically isotropic liquid-crystal composition and the polymerizable monomer of the second embodiment of the invention.

2.1 Polymerization Conditions Upon Manufacture of Polymer-Liquid-Crystal Composite Material The optically isotropic polymer-liquid-crystal composite material in the third embodiment of the invention is not particularly limited, if the composite material contains both of a liquid-crystal material and a polymer compound, but the composite material may be in a state in which the polymer is partially or wholly not dissolved into the liquid-crystal material, and in a state in which the polymer is subjected to phase separation from the liquid-crystal material. The polymer-liquid-crystal composite material of the invention can also be manufactured by mixing an optically isotropic liquid-crystal composition and a polymer obtained by being previously polymerized, but is preferably manufactured by mixing a low molecular weight monomer, a macromonomer, an oligomer or the like (hereinafter, collectively referred to as "monomer or the like") serving as a material of the polymer, and the optically isotropic liquid-crystal composition, and then performing the polymerization reaction in the resulting mixture.

In the second embodiment of the invention in which the mixture contains the monomer or the like and the liquid-crystal composition, the mixture containing the optically isotropic liquid-crystal composition and the polymerizable monomer is also referred to as "polymerizable monomer-liquid-crystal mixture" herein. "Polymerizable monomer-liquid-crystal mixture" may contain, when necessary, a polymerization initiator, a curing agent, a catalyst, a stabilizer, a dichroic dye (merocyanine, styryl, azo, azomethine, azoxy, quinophthalone, anthraquinone, tetrazine dye or the like), a photochromic compound or the like as described below within the range in which advantageous effects of the invention are not adversely affected. For example, the polymerizable monomer-liquid-crystal mixture of the invention may contain, when necessary, the polymerization initiator in an amount of 0.1 to 20 parts by weight based on the polymerizable monomer.

The polymerization in the mixture is preferably performed in the mixture in the non-liquid-crystal isotropic phase or the optically isotropic liquid-crystal phase. More specifically, a polymerization temperature is preferably a temperature at which the polymer-liquid-crystal composite material shows high transparency and isotropy. The polymerization is further preferably terminated at a temperature at which the mixture of the monomer and the liquid-crystal material exhibits the non-liquid-crystal isotropic phase or the blue phase, and in the non-liquid-crystal isotropic phase or the optically isotropic liquid-crystal phase. More specifically, the temperature is preferably adjusted to a level at which the polymer-liquid-crystal composite material, after the polymerization, causes no substantial scattering of light on a side of a wavelength longer than a wavelength of visible light and an optically isotropic state is exhibited.

2.2 Polymer Raw Material Constituting Composite Material

As a polymer raw material constituting the composite material of the invention, for example, the low molecular weight monomer, the macromonomer or the oligomer can be used, and a polymer raw material monomer herein is used in the meaning of including the low molecular weight monomer, the macromonomer and the oligomer. Moreover, the resulting polymer preferably has three-dimensional cross-linked structure, and therefore a polyfunctional monomer having two or more polymerizable functional groups is preferably used as the polymer raw material monomer. The polymerizable functional group is not particularly limited, but specific examples include an acryl group, a methacryl group, a glycidyl group, an epoxy group, an oxetanyl group and a vinyl group. From a viewpoint of a rate of polymerization, an acryl group and a methacryl group are preferred. In the polymer raw material monomer, in a case where a monomer having two or more polymerizable functional groups is contained in an amount of 10% by weight or more, high transparency and isotropy are easily exhibited in the composite material of the invention, and therefore such a case is preferred.

Moreover, in order to obtain a preferred composite material, a polymer having a mesogen moiety is preferred, and as the polymer raw material monomer, a raw material monomer having the mesogen moiety can be partially or wholly used therefor.

2.2.1 Monofunctional or Bifunctional Monomer Having Mesogen Moiety

A monofunctional or bifunctional monomer having the mesogen moiety is not particularly limited in structure. Specific examples increase include a compound represented by formula (M1) or (M2) below.

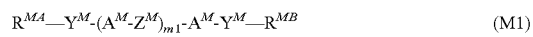

$$R^{MA}-Y^M-(A^M-Z^M)_{m1}-A^M-Y^M-R^{MB} \quad (M1)$$

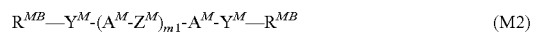

$$R^{MB}-Y^M-(A^M-Z^M)_{m1}-A^M-Y^M-R^{MB} \quad (M2)$$

In formulas (M1) and (M2), $R^{MA}$ is each independently hydrogen, halogen, —C≡N, —N=C=O, —N=C=S or alkyl having 1 to 20 carbons, at least one of —CH$_2$— in the alkyl may be replaced by —O—, —S—, —CO—, —COO—, —OCO—, —CH=CH—, —CF=CF— or —C≡C—, and at least one of hydrogen in the alkyl may be replaced by halogen or —C≡N.

Preferred $R^{MA}$ includes hydrogen, halogen, —C≡N, —CF$_3$, —CF$_2$H, —CFH$_2$, —OCF$_3$, —OCF$_2$H, alkyl having 1 to 20 carbons, alkoxy having 1 to 19 carbons, alkenyl having 2 to 21 carbons, and alkynyl having 2 to 21 carbons. Particularly preferred $R^{MA}$ includes —C≡N, alkyl having 1 to 20 carbons and alkoxy having 1 to 19 carbons. $R^{MB}$ is each independently a polymerizable group of group (M3-1) to group (M3-7).

(M3-1)

(M3-2)

(M3-3)

(M3-4)

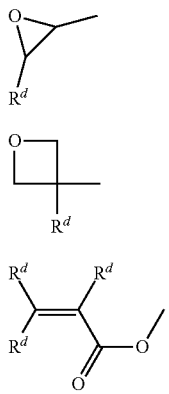

(M3-5)

(M3-6)

(M3-7)

Here, $R^d$ in group (M3-1) to group (M3-7) is each independently hydrogen, halogen or alkyl having 1 to 5 carbons, and at least one of hydrogen in the alkyl may be replaced by halogen. Preferred $R^d$ includes hydrogen, halogen and methyl. Particularly preferred $R^d$ includes hydrogen, fluorine and methyl.

Moreover, group (M3-2), group (M3-3), group (M3-4) and group (M3-7) are preferably polymerized in radical polymerization. Group (M3-1), group (M3-5) and group (M3-6) are preferably polymerized in cationic polymerization. All of the polymerization are living polymerization, and thus the polymerization are initiated if a small amount of radical or cation active species is generated in a reaction system. The polymerization initiator can be used for the purpose of accelerating generation of the active species. For example, light or heat can be used for generation of the active species.

In formulas (M1) and (M2), $A^M$ is each independently an aromatic or non-aromatic 5-membered ring or 6-membered ring, or a condensed ring having 9 or more carbons, but —$CH_2$— in the ring may be replaced by —O—, —S—, —NH— or —$NCH_3$—, and —CH= in the ring may be replaced by —N=, and a hydrogen atom on the ring may be replaced by halogen and alkyl having 1 to 5 carbons or alkyl halide. Specific examples of preferred $A^M$ include 1,4-cyclohexylene, 1,4-cyclohexenylene, 1,4-phenylene, naphthalene-2,6-diyl, tetrahydronaphthalene-2,6-diyl, fluorene-2,7-diyl or bicyclo[2.2.2]octane-1,4-diyl, at least one of —$CH_2$— in the ring may be replaced by —O—, at least one of —CH= may be replaced by —N=, and at least one of hydrogen in the ring may be replaced by halogen, alkyl having 1 to 5 carbons or alkyl halide having 1 to 5 carbons.

In consideration of stability of the compound, —$CH_2$—O—$CH_2$—O— in which oxygen and oxygen are not adjacent to each other is preferred to —$CH_2$—O—O—$CH_2$— in which oxygen and oxygen are adjacent to each other.

Above all, specific examples of particularly preferred $A^M$ include 1,4-cyclohexylene, 1,4-cyclohexenylene, 1,4-phenylene, 2-fluoro-1,4-phenylene, 2,3-difluoro-1,4-phenylene, 2,5-difluoro-1,4-phenylene, 2,6-difluoro-1,4-phenylene, 2-methyl-1,4-phenylene, 2-trifluoromethyl-1,4-phenylene, 2,3-bis(trifluoromethyl)-1,4-phenylene, naphthalene-2,6-diyl, tetrahydronaphthalene-2,6-diyl, fluorene-2,7-diyl, 9-methylfluorene-2,7-diyl, 1,3-dioxane-2,5-diyl, pyridine-2,5-diyl, and pyrimidine-2,5-diyl. In addition, in a configuration of 1,4-cyclohexylene and 1,3-dioxane-2,5-diyl as described above, trans is preferred to cis.

Then, 2-fluoro-1,4-phenylene is structurally identical with 3-fluoro-1,4-phenylene, and thus the latter is not exemplified. The above rule is also applied to a relationship between 2,5-difluoro-1,4-phenylene and 3,6-difluoro-1,4-phenylene, or the like.

In formulas (M1) and (M2), $Y^M$ is each independently a single bond or alkylene having 1 to 20 carbons, and in the alkylene, at least one of —$CH_2$— may be replaced by —O—, —S—, —CH=CH—, —C≡C—, —COO— or —OCO—, but a case where two oxygen atoms are adjacent, such as —O—O—, is excluded. Specific examples of preferred $Y^M$ include a single bond, —$(CH_2)_{m2}$—, —$O(CH_2)_{m2}$— and —$(CH_2)_{m2}O$— (in the formulas described above, m2 is an integer from 1 to 20). Specific examples of particularly preferred $Y^M$ include a single bond, —$(CH_3)_{m2}$, —$O(CH_3)_{m2}$— and —$(CH_3)_{m2}O$— (in the formulas described above, m2 is an integer from 1 to 10).

In formulas (M1) and (M2), $Z^M$ is each independently a single bond, —$(CH_2)_{m3}$—, —$O(CH_2)_{m3}$—, —$(CH_2)_{m3}O$—, —$O(CH_2)_{m3}O$—, —CH=CH—, —C≡C—, —COO—, —OCO—, —$(CF_2)_2$—, —$(CH_2)_2$—COO—, —OCO—$(CH_2)_2$—, —CH=CH—COO—, —OCO—CH=CH—, —C≡C—COO—, —OCO—C≡C—, —CH=CH—$(CH_2)_2$—, —$(CH_2)_2$—CH=CH—, —CF=CF—, —C≡C—CH=CH—, —CH=CH—C≡C—, —$OCF_2$—$(CH_2)_2$—, $(CH_2)_2$—$CF_2O$—, —$OCF_2$— or —$CF_2O$— (in the formulas described above, m3 is an integer from 1 to 20). Specific examples of preferred $Z^M$ include a single bond, —$(CH_2)_{m3}$—, —$O(CH_2)_{m3}$—, —$(CH_2)_{m3}O$—, —CH=CH—, —C≡C—, —COO—, —OCO—, —$(CH_2)_2$—COO—, —OCO—$(CH_2)_2$—, —CH=CH—COO—, —OCO—CH=CH—, —$OCF_2$— and —$CF_2O$—.

In formulas (M1) and (M2), m1 is an integer from 1 to 6. Specific examples of preferred m1 include an integer from 1 to 3. A formula when m1 is 1 represents a bicyclic compound having two rings such as a 6-membered ring. A formula when m1 is 2 and 3 represents a tricyclic compound and a tetracyclic compound, respectively. For example, when m1 is 1, two of $A^M$ may be identical or different. Moreover, for example, when m1 is 2, three of $A^M$ (or two of $Z^M$) may be identical or different. A same rule applies to $A^M$ or $Z^M$ when m1 is 3 to 6. A same rule also applies to $R^{MB}$, $R^d$ and $Y^M$.

Even if compound (M1) represented by formula (M1), and compound (M2) represented by formula (M2) contain an isotope such as $^2H$ (deuterium) and $^{13}C$ in an amount higher than natural abundance, compound (M1) and compound (M2) can be preferably used because such compounds similar characteristics.

Further preferred examples of compound (M1) and compound (M2) include compounds (M1-1) to (M1-41) and compounds (M2-1) to (M2-27) as represented by formulas (M1-1) to (M1-41) and (M2-1) to (M2-27) below. In the compounds, meanings of $R^{MA}$, $R^{MB}$, $R^d$, $Z^M$, $A^M$, $Y^M$ and p are identical with meanings thereof in formula (M1) and formula (M2) as described in the embodiment of the invention.

The partial structure below in compounds (M1-1) to (M1-41) and (M2-1) to (M2-27) will be described. Partial structure (a1) represents 1,4-phenylene in which at least one of hydrogen is replaced by fluorine. Partial structure (a2) represents 1,4-phenylene in which at least one of hydrogen may be replaced by fluorine. Partial structure (a3) represents 1,4-phenylene in which at least one of hydrogen may be replaced by any one of fluorine or methyl. Partial structure (a4) represents fluorene in which hydrogen in 9-position may be replaced by methyl.

(a1) 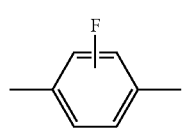
(a2) 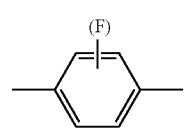
(a3) 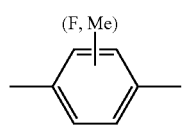
(a4) 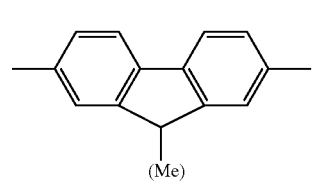
(M1-1) 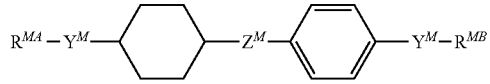
(M1-2) 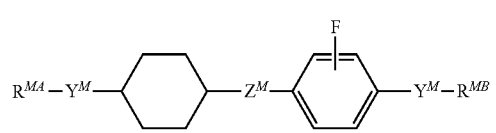
(M1-3) 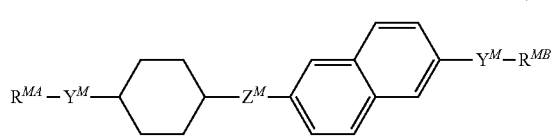
(M1-4) 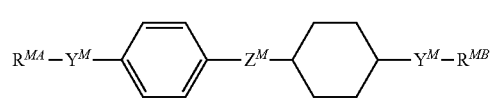
(M1-5) 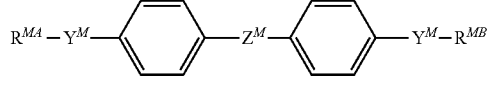
(M1-6) 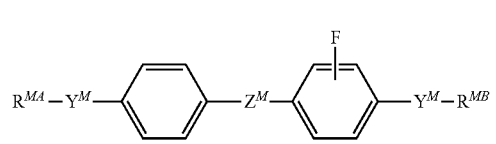
(M1-7) 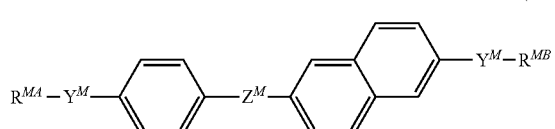
(M1-8) 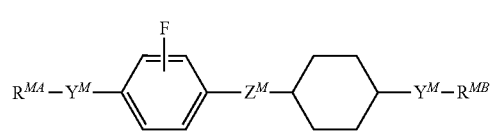
(M1-9) 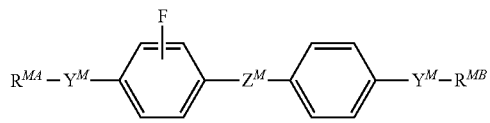
(M1-10) 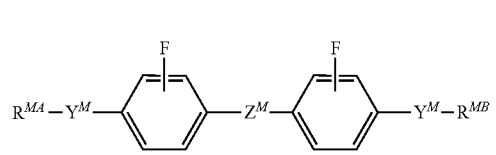
(M1-11) 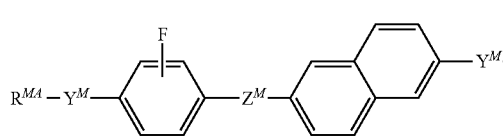
(M1-12) 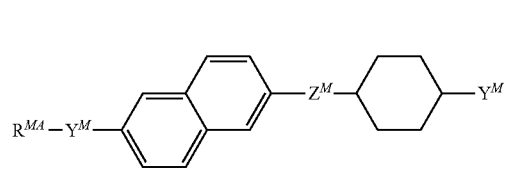
(M1-13) 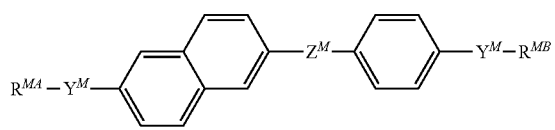
(M1-14) 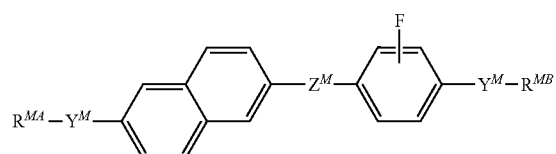
(M1-15) 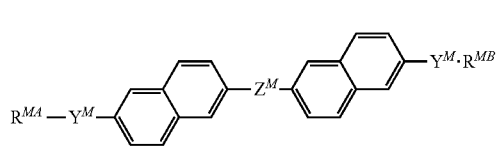
(M1-16) 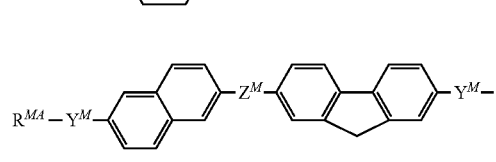

-continued
(M1-17)
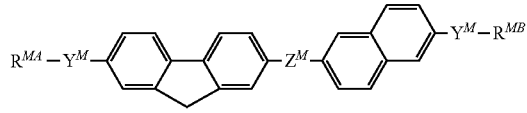
(M1-18)
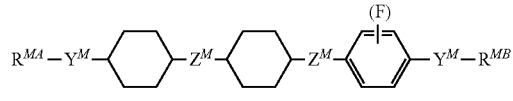
(M1-19)
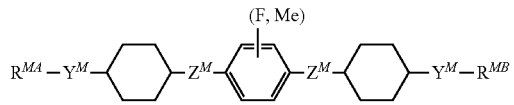
(M1-20)
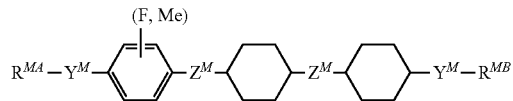
(M1-21)
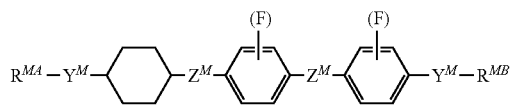
(M1-22)
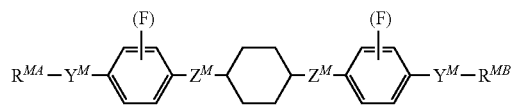
(M1-23)
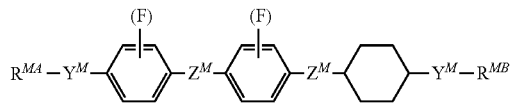
(M1-24)
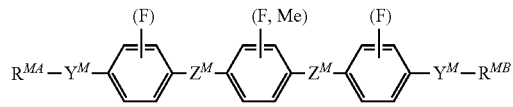
(M1-25)
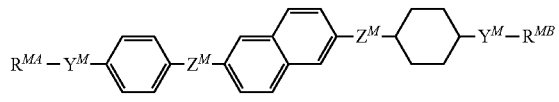
(M1-26)
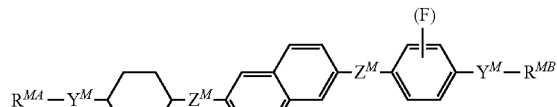
(M1-27)
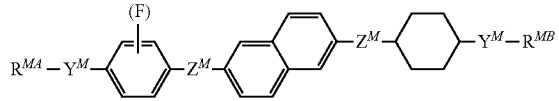
(M1-28)
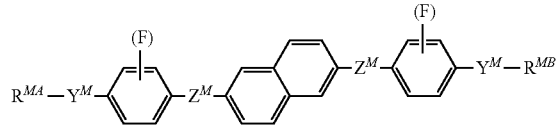
(M1-29)
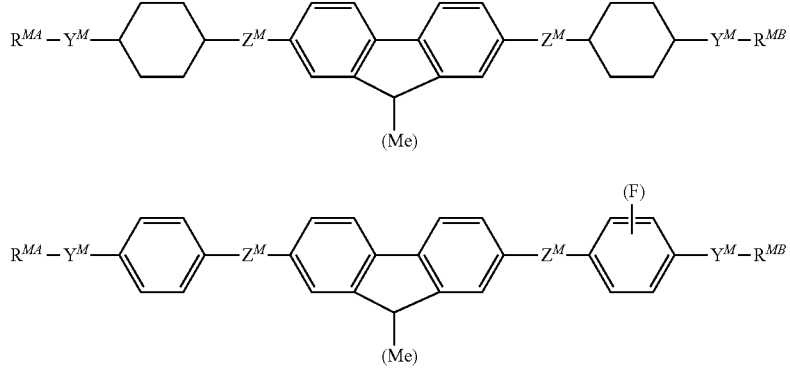
(M1-30)
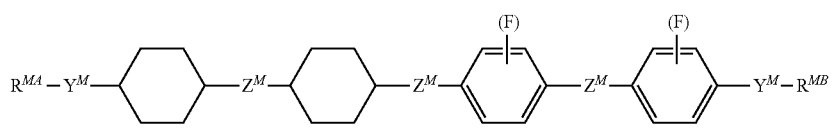
(M1-31)
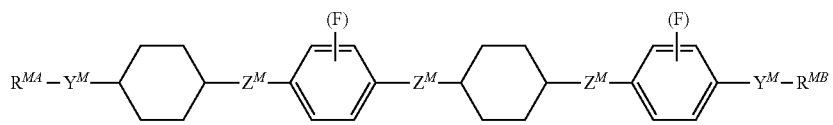
(M1-32)
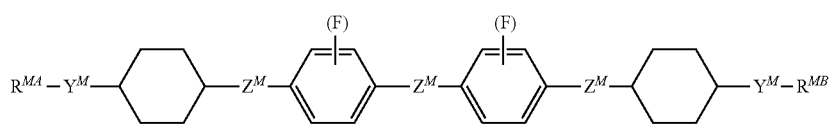
(M1-33)

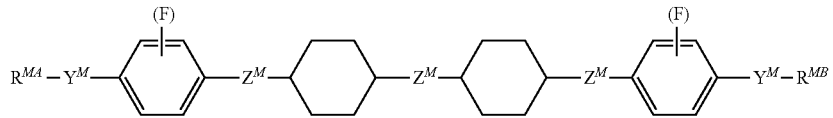
(M1-34)
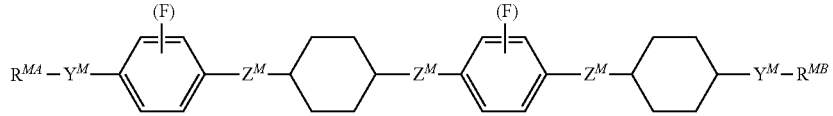
(M1-35)
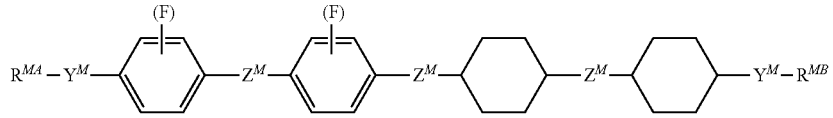
(M1-36)
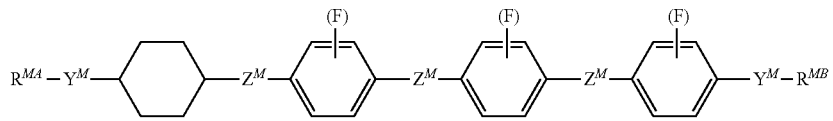
(M1-37)
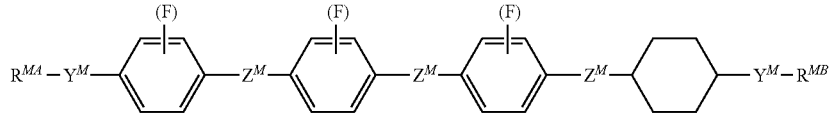
(M1-38)
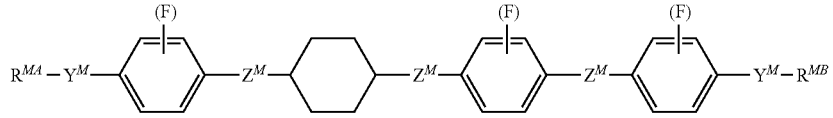
(M1-39)
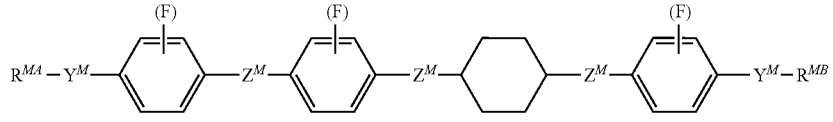
(M1-40)
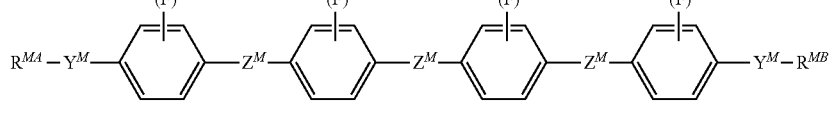
(M1-41)
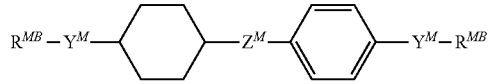
(M2-1)
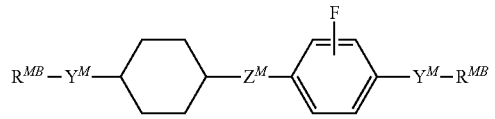
(M2-2)
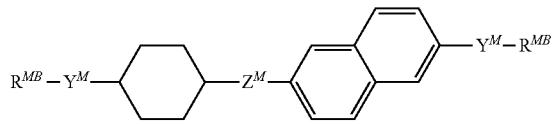
(M2-3)
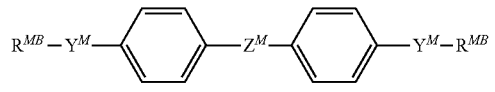
(M2-4)
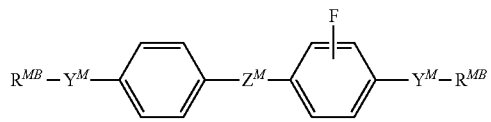
(M2-5)
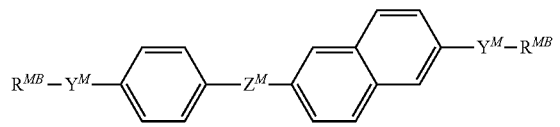
(M2-6)

-continued
(M2-7)
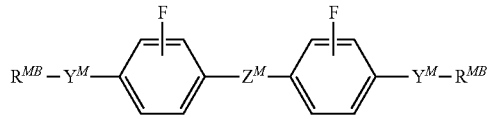
(M2-8)
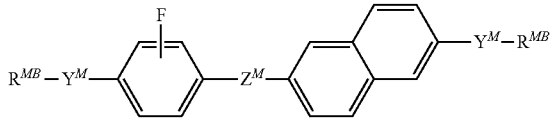
(M2-9)
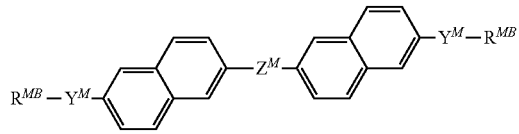
(M2-10)
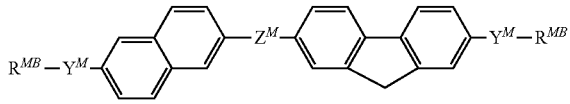
(M2-11)
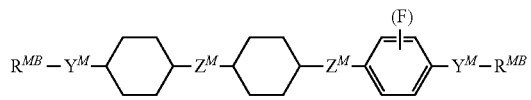
(M2-12)
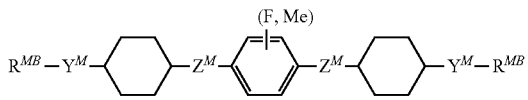
(M2-13)
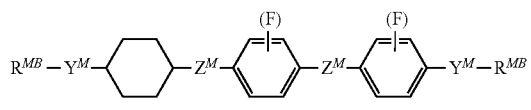
(M2-14)
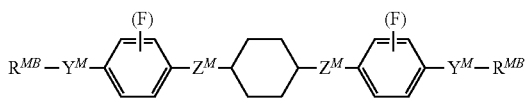
(M2-15)
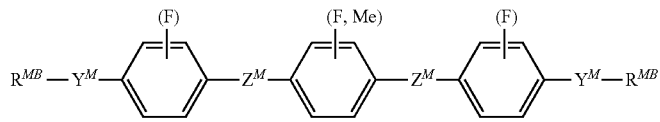
(M2-16)
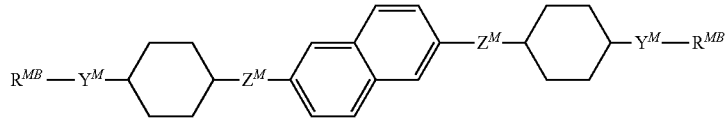
(M2-17)
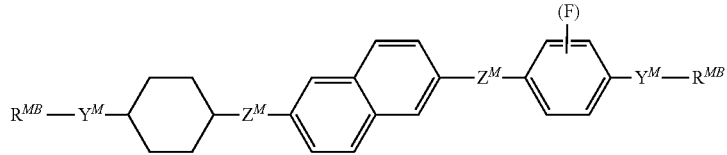
(M2-18)
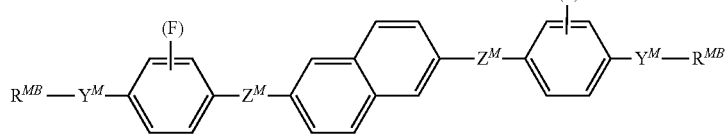
(M2-19)
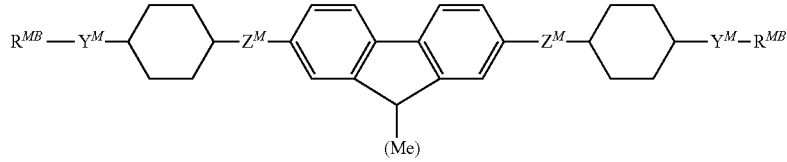
(M2-20)
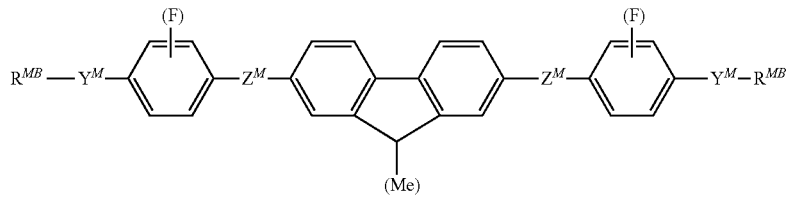

-continued

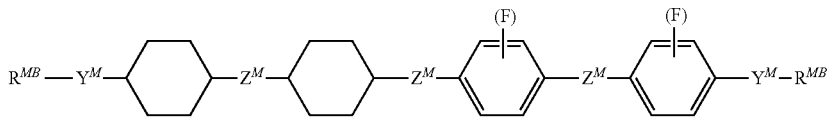
(M2-21)

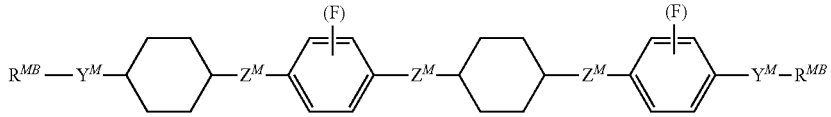
(M2-22)

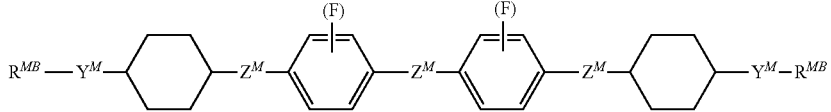
(M2-23)

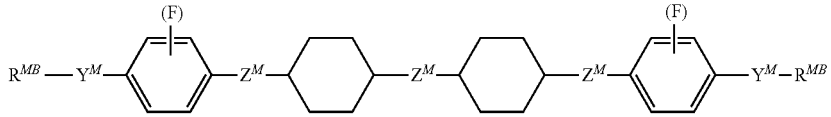
(M2-24)

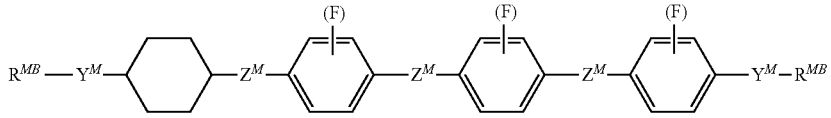
(M2-25)

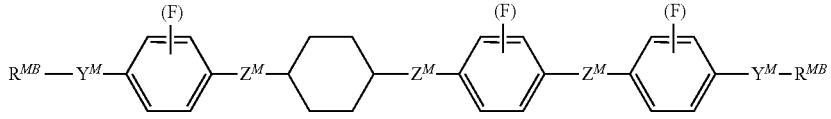
(M2-26)

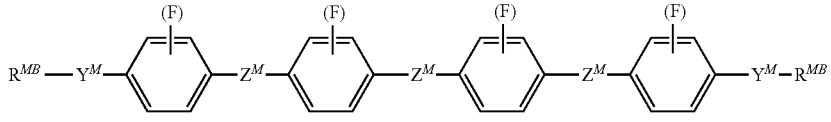
(M2-27)

A monomer having no mesogen moiety, a monomer (M1) having the mesogen moiety and a polymerizable compound other than (M2) as described above can be used when necessary.

For the purpose of optimizing the optical isotropy of the polymer-liquid-crystal composite material of the invention, a monomer having the mesogen moiety and three or more polymerizable functional groups can also be used. A publicly known compound can be preferably used as the monomer having the mesogen moiety and the three or more polymerizable functional groups. Specific examples include (M4-1) to (M4-3), and further specific examples include compounds described in JP 2000-327632 A, JP 2004-182949 A and JP 2004-59772 A. However, in (M4-1) to (M4-3), $R^{MB}$, $Z^M$, $Y^M$ and (F) represent meanings identical to the meanings described above.

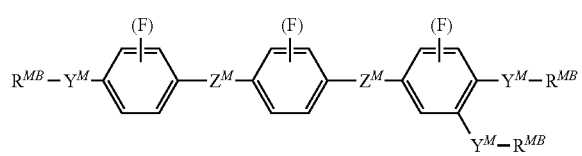
(M4-1)

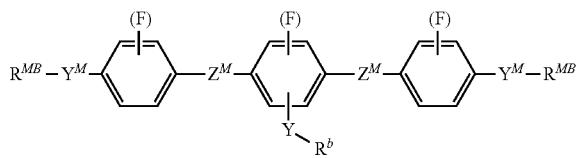
(M4-2)

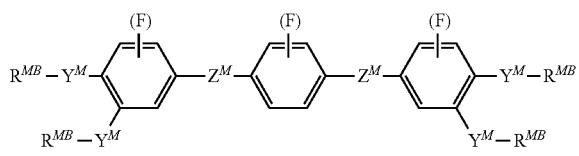
(M4-3)

In addition, "alkyl having 1 to 20 carbons" herein is preferably alkyl having 1 to 10 carbons, and further preferably, alkyl having 1 to 6 carbons. Specific examples of the alkyl are include, but not limited thereto, methyl, ethyl, propyl, isopropyl, n-butyl, s-butyl, t-butyl, pentyl, hexyl and dodecanyl.

"Alkenyl having 2 to 21 carbons" herein is preferably alkenyl having 2 to 10 carbons, and further preferably, alkenyl having 2 to 6 carbons. Specific examples of the alkenyl include, but not limited thereto, vinyl, allyl, propenyl, isopropenyl, 2-methyl-1-propenyl, 2-methylallyl and 2-butenyl.

"Alkynyl having 2 to 21 carbons" herein is preferably alkynyl having 2 to 10 carbons, and further preferably, alkynyl having 2 to 6 carbons. Specific examples of the alkynyl include, but not limited thereto, ethynyl, propynyl and butynyl.

"Alkoxy having 1 to 19 carbons" herein is preferably alkoxy having 1 to 10 carbons, and further preferably, alkoxy having 2 to 6 carbons. Specific examples of the alkoxy include, but not limited thereto ethoxy, propoxy, butoxy and pentyloxy.

2.2.2 Monomer Having No Mesogen Moiety and Having Polymerizable Functional Group Specific examples of the monomer having no mesogen moiety and having the polymerizable functional group include straight-chain or branched-chain acrylate having 1 to 30 carbons and straight-chain or branched-chain diacrylate having 1 to 30 carbons. Specific examples of the monomer having three or more polymerizable functional groups include glycerol propoxylate (1PO/OH)triacrylate, pentaerythritol propoxylate triacrylate, pentaerythritol triacrylate, trimethylolpropane ethoxylate triacrylate, trimethylolpropane propoxylate triacrylate, trimethylolpropane triacrylate, di(trimethylolpropane)tetraacrylate, pentaerythritol tetraacrylate, di(pentaerythritol)pentaacrylate and di(pentaerythritol)hexaacrylate, but the monomer is in no way limited thereto.

2.3 Polymerization Initiator

The polymerization reaction in manufacture of the polymer constituting the composite material of the invention is not particularly limited, and for example, photoradical polymerization, thermal radical polymerization or photocationic polymerization is performed.

Specific examples of a photoradical polymerization initiator that can be used in the photoradical polymerization include DAROCUR (registered trademark) 1173 and 4265 (trade names for all, made by Ciba Specialty Chemicals Inc.) and IRGACURE (registered trademark) 184, 369, 500, 651, 784, 819, 907, 1300, 1700, 1800, 1850 and 2959 (trade names for all, made by Ciba Specialty Chemicals Inc.).

Specific examples of a preferred initiator of radical polymerization by heat that can be used in the thermal radical polymerization include benzoyl peroxide, diisopropyl peroxydicarbonate, t-butylperoxy-2-ethylhexanoate, t-butyl peroxypivalate, t-butyl peroxydiisobutyrate, lauroyl peroxide, dimethyl 2,2'-azobis(isobutyrate) (MAIB), di-t-butyl peroxide (DTBPO), azobisisobutyronitrile (AIBN) and azobiscyclohexanecarbonitrile (ACN).

Specific examples of a photocationic polymerization initiator that can be used in the photocationic polymerization include diaryliodonium salt (hereinafter, referred to as "DAS") and triarylsulfonium salt (hereinafter, referred to as "TAS").

Specific examples of DAS include diphenyliodonium tetrafluoroborate, diphenyliodonium hexafluorophosphonate, diphenyliodonium hexafluoroarsenate, diphenyliodonium trifluoromethanesulfonate, diphenyliodonium trifluoroacetate, diphenyliodonium p-toluenesulfonate, diphenyliodonium tetra(pentafluorophenyl)borate, 4-methoxyphenyl phenyliodonium tetrafluoroborate, 4-methoxyphenyl phenyliodonium hexafluorophosphonate, 4-methoxyphenyl phenyliodonium hexafluoroarsenate, 4-methoxyphenyl phenyliodonium trifluoro methanesulfonate, 4-methoxyphenyl phenyliodonium trifluoroacetate and 4-methoxyphenyl phenyliodonium-p-toluenesulfonate.

High sensitivity can be achieved by adding, to DAS, a photosensitizer such as thioxanthone, phenothiazine, chlorothioxanthone, xanthone, anthracene, diphenylanthracene and rubrene.

Specific examples of TAS include triphenylsulfonium tetrafluoroborate, triphenylsulfonium hexafluorophosphonate, triphenylsulfonium hexafluoroarsenate, triphenylsulfonium trifluoromethanesulfonate, triphenylsulfonium trifluoroacetate, triphenylsulfonium-p-toluenesulfonate, triphenylsulfonium tetra(pentafluorophenyl)borate, 4-methoxyphenyl diphenylsulfonium tetrafluoroborate, 4-methoxyphenyl diphenylsulfonium hexafluorophosphonate, 4-methoxyphenyl diphenylsulfonium hexafluoroarsenate, 4-methoxyphenyl diphenylsulfonium trifluoromethanesulfonate, 4-methoxyphenyl diphenylsulfonium trifluoroacetate and 4-methoxyphenyl diphenylsulfonium-p-toluenesulfonate.

Specific examples of trade names of the photocationic polymerization initiator include Cyracure (registered trademark) UVI-6990, Cyracure UVI-6974 and Cyracure UVI-6992 (trade names for each, made by UCC), Adekaoptomer SP-150, SP-152, SP-170 and SP-172 (trade names for each, (made by ADEKA Corporation), Rhodorsil Photoinitiator 2074 (trade name, made by Rhodia Japan, LTD.), IRGACURE (registered trademark) 250 (trade name, made by Ciba Specialty Chemicals Inc.) and UV-9380C (trade name, (made by GE Toshiba Silicones Co., Ltd.).

2.4 Curing Agent or the Like

In manufacture of the polymer constituting the composite material of the invention, one or two or more kinds of other preferred components, in other than the monomer or the like and the polymerization initiator for example, the curing agent, the catalyst, the stabilizer or the like may be added.

As the curing agent, a conventionally known latent curing agent that is ordinarily used as the curing agent for an epoxy resin can be used. Specific examples of the latent curing agent for the epoxy resin include an amine curing agent, a novolak resin curing agent, an imidazole curing agent and an acid anhydride curing agent. Specific examples of the amine curing agent include aliphatic polyamine such as diethylenetriamine, triethylenetetramine, tetraethylenepentamine, m-xylenediamine, trimethyl hexamethylenediamine, 2-methyl pentamethylene diamine and diethylamino propylamine, alicyclic polyamine such as isophorone diamine, 1,3-bisaminomethylcyclohexane, bis(4-aminocyclohexyl)methane, norbornene diamine, 1,2-diaminocyclohexane and laromine, and aromatic polyamine such as diaminodiphenylmethane, diaminodiphenylethane and metaphenylene diamine.

Specific examples of the novolak resin curing agent include a phenol novolak resin and a bisphenol novolak resin. Specific examples of the imidazole curing agent include 2-methylimidazole, 2-ethylhexylimidazole, 2-phenylimidazole and 1-cyanoethyl-2-phenylimidazolium trimellitate.

Specific examples of the acid anhydride curing agent include tetrahydrophthalic anhydride, hexahydrophthalic anhydride, methyltetrahydrophthalic anhydride, methylhexahydrophthalic anhydride, methylcyclohexenetetracarboxylic dianhydride, phthalic anhydride, trimellitic anhydride, pyromellitic anhydride and benzophenonetetracarboxylic dianhydride.

Moreover, a curing accelerator for accelerating a curing reaction between the curing agent and a polymerizable compound having glycidyl, epoxy and oxetanyl may be further used. Specific examples of the curing accelerator include benzyldimethylamine, tris(dimethylaminomethyl)

phenol, tertiaryamines such as dimethylcyclohexylamine, 1-cyanoethyl-2-ethyl-4-methylimidazole, imidazoles such as 2-ethyl-4-methylimidazole, an organophosphorus compound such as triphenylphosphine, quaternaryphosphonium salts such as tetraphenylphosphonium bromide, diazabicycloalkene such as 1,8-diazabicyclo[5.4.0]undecene-7 and an organic acid salt thereof, quaternaryammonium salts such as tetraethylammonium bromide and tetrabutylammonium bromide, boron trifluoride and a boron compound such as triphenylborate. The curing accelerator can be used alone or in combination of two or more kinds.

Moreover, for example, in order to prevent unwanted polymerization in storage, addition of the stabilizer is preferred. As the stabilizer, all the compounds known to those skilled in the art can be used. Typified examples of the stabilizer include 4-ethoxyphenol, hydroquinone and butylated hydroxytoluene (BHT).

The optically isotropic polymer-liquid-crystal composite material related to a preferred embodiment of the invention can exhibit the optically isotropic liquid-crystal phase in a wide temperature range. Moreover, the polymer-liquid-crystal composite material related to the preferred embodiment of the invention has a significantly high response speed. Moreover, the polymer-liquid-crystal composite material related to the preferred embodiment of the invention can be preferably used for an optical element or the like such as a display device based on effects thereof.

2.5 Content of Liquid-Crystal Composition or the Like

A content of the liquid-crystal composition in the polymer-liquid-crystal composite material of the invention is preferably as high as possible it the content is in the range in which the composite material can exhibit isotropy, because as the content of the liquid-crystal composition is higher, an electric birefringence value (Kerr coefficient) of the composite material of the invention becomes larger.

In the polymer-liquid-crystal composite material of the invention, the content of the liquid-crystal composition is preferably 60 to 99% by weight, further preferably, 60 to 95% by weight, and particularly preferably, 75 to 95% by weight, based on the composite material. A content of the polymer is preferably 1 to 40% by weight, further preferably, 3 to 30% by weight, and particularly preferably, 3 to 25% by weight, based on the composite material.

2.6 Any Other Component

The polymer-liquid-crystal composite material of the invention may contain, for example, a dichroic dye and a photochromic compound within the range in which the advantageous effects of the invention are not adversely affected.

The invention will be described in more detail by way of Examples below, but the invention is not limited by the Examples. In addition, unless otherwise noted, "%" is expressed in terms of "% by weight."

3 Liquid-Crystal Device

A fourth embodiment of the invention includes the optical element driven in the optically isotropic liquid-crystal phase containing the optically isotropic liquid-crystal composition or the polymer-liquid-crystal composite material (hereinafter, the liquid-crystal composition and the polymer-liquid-crystal composite material are collectively referred to as "liquid-crystal medium" in several cases).

As shown in FIG. 1, specific examples of structure of the liquid-crystal display device include structure in which, in electrodes in a comb electrode substrate, electrode 1 extended from a left-hand side and electrode 2 extended from a right-hand side are alternately arranged. When a potential difference exists between electrode 1 and electrode 2, on the comb electrode substrate as shown in FIG. 1, a state in which electric fields in two directions, an upper direction and a lower direction, exist can be provided.

4 Use for Optical Element

A fifth embodiment of the invention includes use, for the optical element, of the liquid-crystal composition containing the achiral component containing at least one compound selected from the group of compounds represented by formula (1-A), and the chiral compound represented by formula (K1) or (K2), and exhibiting the optically isotropic liquid-crystal phase. The liquid-crystal composition shows a low drive voltage and a short response time, and therefore is effective in achieving a low voltage drive and a high speed response of the optical element.

EXAMPLES

The invention will be further specifically described by way of Examples below, but the invention is in no way limited by the Examples.

In Examples herein, I represents a non-liquid-crystal isotropic phase, N represents a nematic phase, N* represents a chiral nematic phase, BP represents a blue phase, and BPX represents an optically isotropic liquid-crystal phase in which diffracted light having two or more colors are not observed. An I-N phase transition point herein is referred to as an N-I point in several cases. An I-N* phase transition point is referred to as an N*-I point in several cases. An I-BP phase transition point is referred to as a BP-I point in several cases.

In Examples herein, unless otherwise noted, measurement and calculation of values of physical properties or the like were carried out by the methods described in EIAJ ED-2521A as the Standard of Electronic Industries Association of Japan.

Specific measuring methods, calculating methods and so forth other than the methods of measurement of an elastic constant and dielectric anisotropy and measurement of refractive index anisotropy above were as described below.

(1) I-N Phase Transition Point ($T_{NI}$)

A sample was put on a hot plate in a melting point apparatus equipped with a polarizing microscope, and in a state of a crossed nicol, the sample was first heated to a temperature at which the sample was changed to a non-liquid-crystal isotropic phase, and then cooled at a rate of 1° C. per minute to allow a chiral nematic phase or an optically anisotropic phase to completely appear. A phase transition temperature in a process thereof was measured, and then the sample was heated at a rate of 1° C. per minute, and a phase transition temperature in a process thereof was measured. When discrimination of the phase transition point was difficult in a dark field under the crossed nicol in the optically isotropic liquid-crystal phase, a polarizing plate was shifted by 1 to 10 degrees from the state of the crossed nicol, and then the phase transition temperature was measured.

(2) Refractive Index (n∥ and n⊥; Measured at 25° C.)

Measurement was carried out by an Abbe refractometer with a polarizing plate mounted on an ocular by using light at a wavelength of 589 nanometers. A surface of a main prism was rubbed in one direction (rubbing), and then a sample was added dropwise onto the main prism. A refractive index (n∥) was measured when the direction of polarized light was parallel to the direction of the rubbing. A refractive index (n⊥) was measured when the direction of polarized light was perpendicular to the direction of the rubbing.

(3) Pitch (P; Measured at 25° C.; Nm)

A pitch length was measured by using selective reflection (*Handbook of Liquid Crystals* (Ekisho Binran, page 196 (Maruzen Co., Ltd., issued in 2000)). In a selective reflection wavelength λ, a relational expression: <n>p/λ=1 holds, in which <n> represents an average refractive index, and is given by the following formula: $<n>=\{(n\|^2+n\perp^2)/2\}^{1/2}$. The selective reflection wavelength was measured by a microspectrophotometer (trade name FE-3000, Otsuka Electronics Co., Ltd.). A pitch was determined by dividing the resulting reflection wavelength by the average refractive index.

With regard to the pitch of a cholesteric liquid-crystal having a reflection wavelength in a long wavelength region or a short wavelength region of visible light, and the cholesteric liquid-crystal difficult measurement of which was difficult, the pitch was determined by adding a chiral compound at a concentration (concentration C') at which a sample had the selective reflection wavelength in a visible light region to measure a selective reflection wavelength (λ'), and an original selective reflection wavelength (λ) was calculated from an original chiral concentration (concentration C) according to a linear extrapolation method (λ=λ'× C'/C).

(4) HTP (Helical Twisting Power) (25° C.; μm⁻¹)

HTP was given by using values of the average refractive index <n> and the pitch as determined by the method described above according to the following expression: HTP=<n>/(λ·C), in which λ represents a selective reflection wavelength (nm) and C represents a chiral concentration (% by weight).

A ratio (percentage) of a component or a liquid-crystal compound was expressed in terms of weight percentage (% by weight) based on the total weight of the liquid-crystal compound. The composition was prepared by measuring a weight of the component of the liquid-crystal compound or the like and then by mixing the components. Therefore, calculation of % by weight of the component is easy.

Example 1

Synthesis of Compound (K122-S1) of the Invention

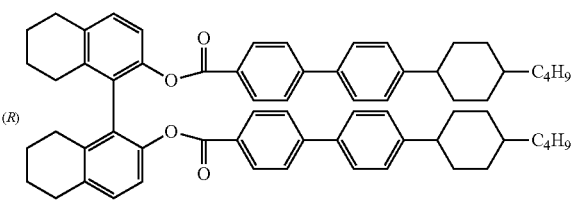

(in compound (K122), a compound in which nk1=nk2=0, n=0 and $R^{k2}=C_4H_9$.)

Compound (K122-S1) was prepared according to a scheme described below.

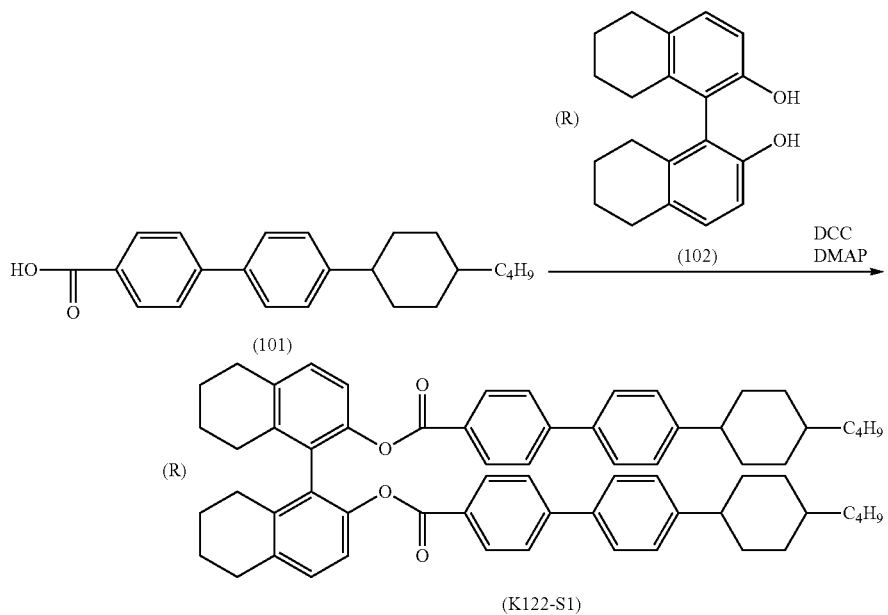

Under a nitrogen atmosphere, a dichloromethane (5 mL) solution of compound (102) (0.500 g, 1.70 mmol) was cooled to 0° C., N,N'-dicyclohexylcarbodiimide (0.770 g, 3.74 mmol), 4-dimethylaminopyridine (0.120 g, 1.02 mmol) and a carboxylic acid derivative (106) (1.14 g, 3.40 mmol) were added thereto, and the resulting mixture was stirred at an ordinary temperature for 8 hours. The resulting reaction liquid was poured into water and dichloromethane (50 mL) was added thereto, and the resulting mixture was washed twice with sodium bicarbonate water, and twice with water, subsequently concentrated, and then the resulting residue was isolated and purified by silica gel column chromatography (developing solvent: toluene) to obtain compound (K122-S1) (1.14 g, 1.22 mmol, yield: 71.8%). A melting point (° C.) of the compound was C 66.4 I.

¹H-NMR (CDCl₃, ppm): δ 0.909-0.923 (6H, t), 1.03-1.11 (4H, m), 1.23-1.33 (16H, m), 1.44-1.52 (4H, m), 1.64-1.77 (8H, m), 1.87-1.93 (8H, dt), 2.26-2.32 (2H, dt), 2.47-2.54

(4H, m), 2.70-2.82 (4H, m), 7.05-7.13 (4H, q), 7.29-7.30 (4H, d), 7.52-7.57 (8H, dd), 7.83-7.84 (4H, d).

Example 2

Synthesis of Compound (K122-S2) of the Invention

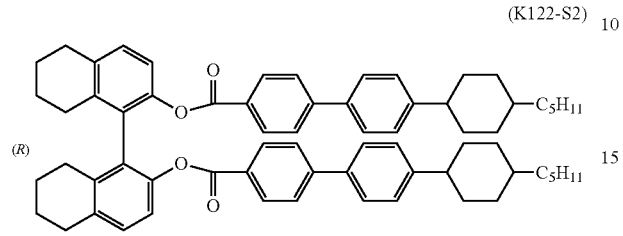

(K122-S2)

(in compound (K122), a compound in which nk1=nk2=0, n=0 and $R^{k2}=C_5H_{11}$.)

Compound (K122-S2) (0.50 g, 0.521 mmol, yield: 69.5%) was obtained by using compound (101) of $C_5H_{11}$ in place of $C_4H_9$ in an alkyl chain length in a manner similar to Example 1. A melting point (° C.) of the compound was C 56.4 I.

$^1$H-NMR (CDCl$_3$, ppm): δ 0.882-0.914 (6H, t), 1.06-1.10 (4H, m), 1.22-1.34 (18H, m), 1.47-1.56 (4H, m), 1.66-1.77 (8H, m), 1.87-1.94 (8H, dt), 2.26-2.32 (2H, dt), 2.48-2.52 (4H, m), 2.69-2.82 (4H, m), 7.07-7.13 (4H, q), 7.28-7.30 (4H, d), 7.52-7.57 (8H, dd), 7.83-7.84 (4H, d).

Example 3

Synthesis of Compound (K121-S1) of the Invention

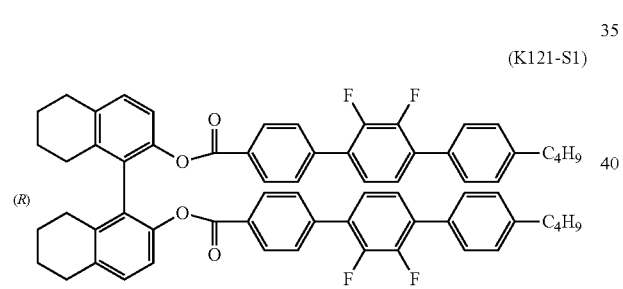

(K121-S1)

(in compound (K121), a compound in which nk1=nk2=0, n=0 and $R^{k2}=C_4H_9$.)

Compound (K121-S1) (1.00 g, 1.01 mmol, yield: 57.0%) was obtained by using compound (101A) described below in place of compound (101) in a manner similar to Example 1. A melting point (° C.) of the compound was C 131.4 I.

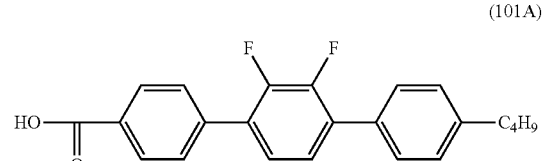

(101A)

$^1$H-NMR (CDCl$_3$, ppm): δ 0.941-0.971 (6H, t), 1.36-1.44 (4H, m), 1.62-1.79 (12H, m), 2.28-2.34 (2H, dt), 2.49-2.55 (2H, dt), 2.66-2.69 (4H, t), 2.72-2.84 (4H, m), 7.10-7.14 (4H, dd), 7.23-7.27 (4H, m), 7.29-7.31 (4H, d), 7.50-7.51 (4H, dd), 7.58-7.60 (4H, dd), 7.88-7.90 (4H, d).

$^{19}$F-NMR (CDCl$_3$, ppm): δ −143.0−−143.1 (2F, dd), −143.2−−143.3 (2F, dd).

Example 4

Synthesis of Compound (K207-S1) of the Invention

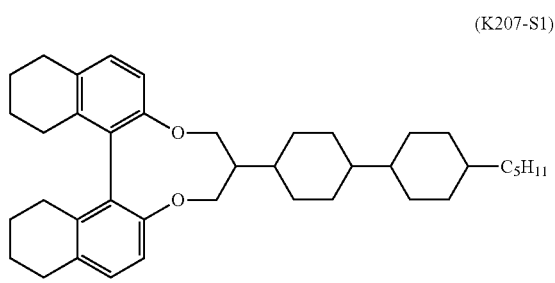

(K207-S1)

(in compound (K207), a compound in which nk1=nk2=0, n=1 and $R^{k2}=C_5H_{11}$.)

Compound (K207-S1) was prepared according to a scheme described below.

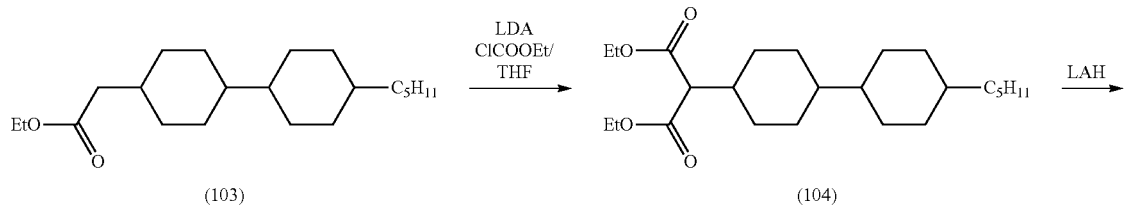

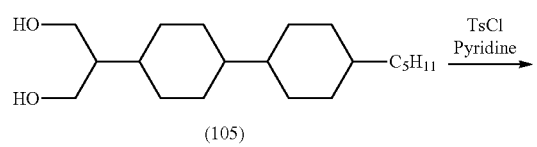

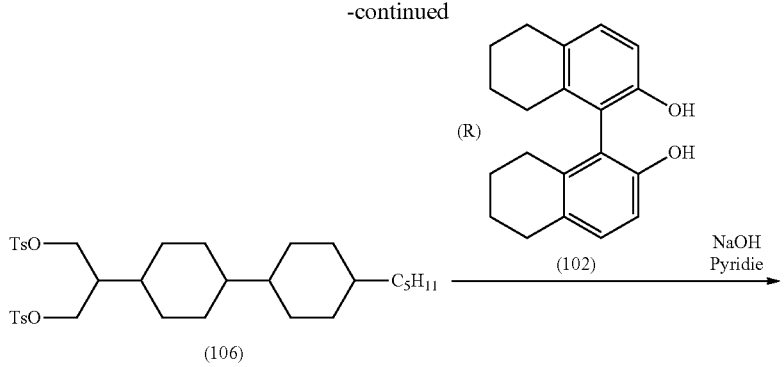

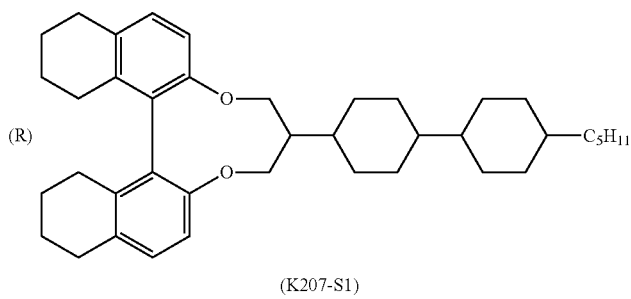

(Step 1) Synthesis of Compound (104)

Under a nitrogen atmosphere, a THF (300 mL) solution of compound (103) (20.0 g, 62.0 mmol) was cooled to −60° C., lithium diisopropylamide-THF (1.03 M/L) (67.7 mL, 74.4 mmol) was added dropwise thereto, and the resulting mixture was stirred at a temperature as was for 1 hour. Further, a THF (20 mL) solution of ethyl chloroformate (8.08 g, 74.4 mmol) was slowly added dropwise thereto in a system at the temperature as was, and the resulting mixture was stirred for 2 hours while the mixture was gradually returned to room temperature. The resulting reaction mixture was poured into water and subjected to extraction with toluene, and the resulting mixture was washed three times with water and then an organic phase was vacuumed. The resulting residue was purified by silica gel column chromatography (developing solvent: n-heptane/toluene=1/1) to obtain compound (104) (17.5 g, 44.4 mmol).

(Step 2) Synthesis of Compound (105)

Under a nitrogen atmosphere, a THF (50 mL) solution of lithium aluminum hydride (LAH) (0.48 g, 12.7 mmol) was cooled to −10° C., a THF (25 mL) solution of compound (104) (2.50 g, 6.34 mmol) was slowly added dropwise thereto, and the resulting mixture was stirred at 0° C. for two days. Then, a 3N-hydrochloric acid aqueous solution (10 mL) was added dropwise thereto in a system and the resulting mixture was stirred for 20 minutes, and then the resulting reaction liquid was subjected to filtration, extraction twice with ethyl acetate (100 mL), the resulting mixture was washed three times with water, and an organic phase was vacuumed and concentrated. The resulting residue was vacuumed and dried without purification to obtain compound (105) (1.60 g, 5.15 mmol).

(Step 3) Preparation of Compound (106)

Under a nitrogen atmosphere, a mixed solution of compound (105) (1.60 g, 5.15 mmol), pyridine (2.45 g, 2.58 mL) and dichloromethane (15 mL) was cooled to 0° C., p-toluenesulfonyl chloride (2.95 g, 15.5 mmol) was slowly added thereto, and the resulting mixture was stirred at a temperature as was for 3 hours. The resulting reaction mixture was poured into water and dichloromethane (50 mL) was added thereto, and the resulting mixture was washed three times with water and then an organic phase was vacuumed and concentrated. The resulting residue was purified by silica gel column chromatography (developing solvent: n-heptane/ethyl acetate=1/1) to obtain compound (106) (2.88 g, 4.65 mmol).

(Step 4) Preparation of Compound (K207-S1)

Under a nitrogen atmosphere, a mixed solution of compound (102) (0.50 g, 1.70 mmol), compound (106) (1.16 g, 1.87 mmol), sodium hydroxide (0.16 g, 3.91 mmol) and N,N-dimethylformamide (DMF) (10 mL) was heated and stirred at 100° C. for 4 hours. The resulting reaction mixture was poured into water, subjected to extraction twice with ethyl acetate (50 mL), the resulting mixture was washed three times with water, and then an organic phase was vacuumed and concentrated. The resulting residue was purified by silica gel column chromatography (developing solvent: n-heptane/toluene=1/1) and further recrystallization filtration (solvent: n-heptane/THF=20:1) to obtain compound (K207-S1). A melting point (° C.) of the compound was C 145.2 I.

$^1$H-NMR (CDCl$_3$, ppm): δ 0.823-0.945 (12H, m), 1.11-1.15 (5H, m), 1.20-1.32 (7H, m), 1.51-1.53 (1H, m), 1.62-1.82 (14H, m), 1.96-2.04 (1H, m), 2.21-2.28 (2H, m), 2.46-2.52 (2H, m), 2.75-2.80 (4H, m), 3.73-3.77 (1H, dd), 3.82-3.87 (1H, t), 4.41-4.45 (2H, m), 6.82-6.84 (1H, d), 6.95-6.96 (1H, d), 7.00-7.05 (2H, dd)

Example 5

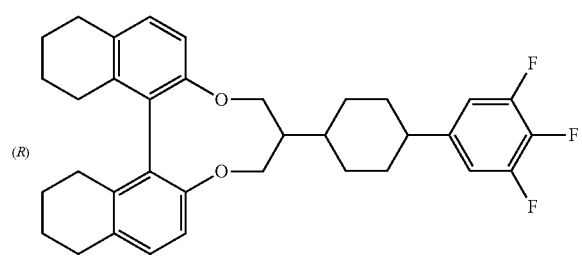
(K208-S1)

(in compound (K208), a compound in which nk1=nk2=0, n=1 and $R^{k2}$=F.)

Compound (K208-S1) (0.300 g, 0.549 mmol, yield: 57.0%) was obtained by using compound (103A) described below in place of compound (103) in a manner similar to Example 1. A melting point (° C.) of the compound was C 98.0 I.

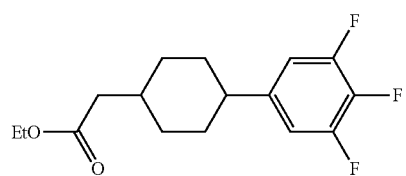
(103A)

$^1$H-NMR (CDCl$_3$, ppm): δ 1.26-1.33 (4H, m), 1.61-1.88 (13H, m), 2.05-2.08 (1H, m), 2.22-2.27 (2H, m), 2.34-2.39 (1H, m), 2.46-2.51 (2H, m), 2.72-2.79 (4H, m), 3.79-3.83 (1H, dd), 3.86-3.91 (1H, t), 4.44-4.48 (2H, dd), 6.72-6.78 (2H, dd), 6.84-6.85 (1H, d), 6.96-6.98 (1H, d), 7.02-7.06 (2H, dd).

$^{19}$F-NMR (CDCl$_3$, ppm): δ −135.6—135.7 (2F, dd), −164.8—164.9 (1F, dt).

Comparative Example 1

Liquid-crystal composition NLC-A was prepared by mixing liquid-crystal compounds shown in the figure below at ratios described below.

Liquid-Crystal Composition NLC-A

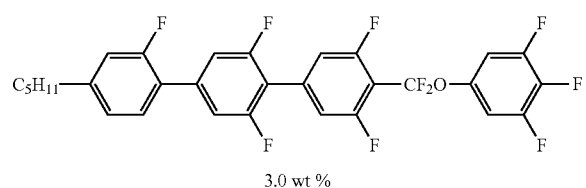
(1-A-01)

3.0 wt %

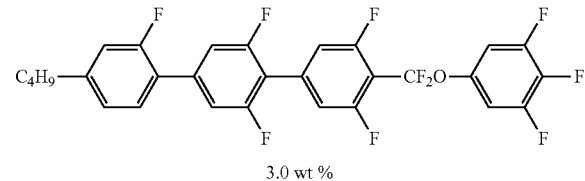
(1-A-01)

3.0 wt %

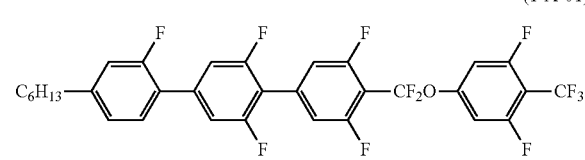
(1-A-01)

4.0 wt %

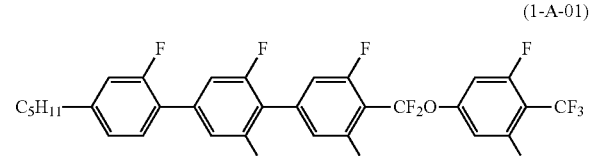
(1-A-01)

4.0 wt %

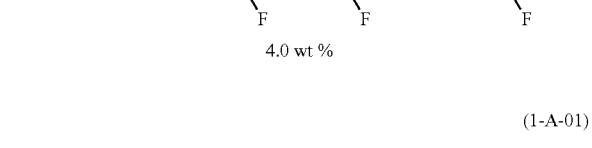
(1-A-01)

4.0 wt %

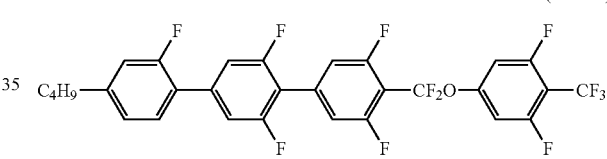
(1-A-01)

4.0 wt %

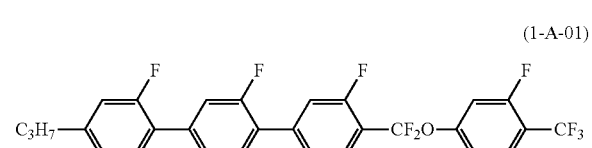
(1-A-01)

4.0 wt %

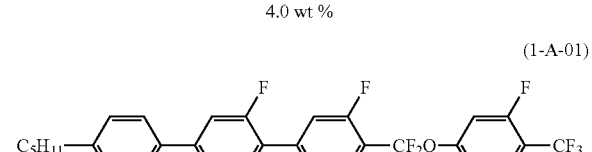
(1-A-01)

4.0 wt %

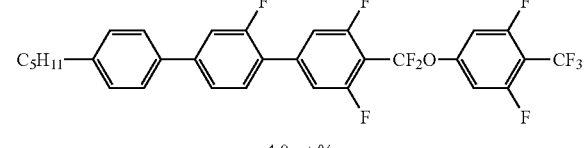
(1-A-01)

4.0 wt %

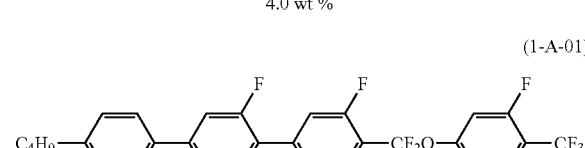
(1-A-01)

4.0 wt %

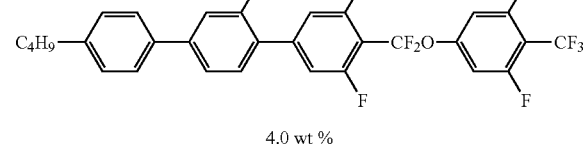
(1-A-01)

4.0 wt %

-continued

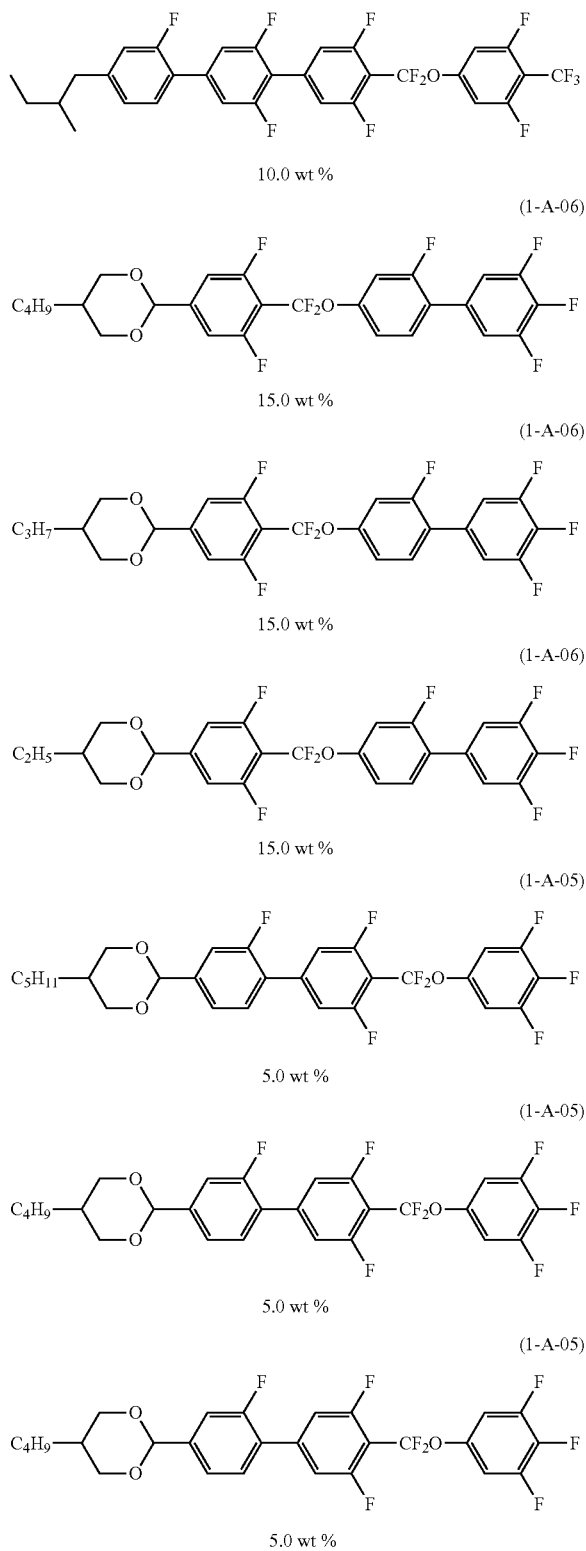

A phase transition temperature (° C.) of liquid-crystal composition NLC-A was N 79.7 I.

A melting point (° C.) of comparative compound (ref. 1) described below was C 153.2 I.

Next, into liquid-crystal composition NLC-A (97.5% by weight), comparative compound (ref. 1) (2.50% by weight) was heated and dissolved at 100° C. to obtain liquid-crystal composition CLC-A1. On the occasion, a heating time needed for obtaining liquid-crystal composition CLC-A1 in which the compound was completely dissolved into the composition was 6 hours.

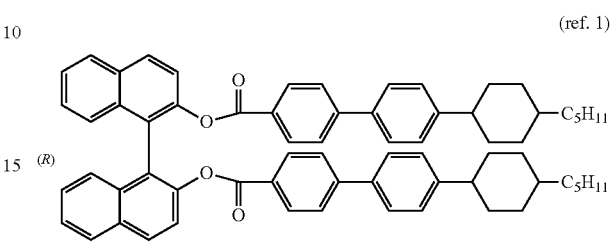

(ref. 1)

A phase transition temperature (° C.) of liquid-crystal composition CLC-A1 was N* 72.7 BP 73.6 I.

Average refractive index <n> of liquid-crystal composition CLC-A1 was 1.56, and a selective reflection wavelength (λ) was 428.0 (nm). HTP of compound (ref. 1) was 132 (μm$^{-1}$) from the values.

Example 6-1

Into liquid-crystal composition NLC-A (97.5% by weight), compound (K122-S2) (2.50% by weight) obtained in Example 2 was heated and dissolved at 100° C. to obtain liquid-crystal composition CLC-B1. On the occasion, a heating time needed for obtaining liquid-crystal composition CLC-B1 in which the compound was completely dissolved into the composition was 2 minutes. Compound (K122-S2) was found to show significantly high solubility.

A selective reflection wavelength (λ) of liquid-crystal composition CLC-B1 was 428.0 (nm). Average refractive index <n> of liquid-crystal composition NLC-A was 1.56. HTP of compound (K122-S2) calculated from the values was 146 (μm$^{-1}$).

HTP of compound E1 to compound E7 described in Table 3 on page 11 in JP 2004-250397 A of Patent literature No. 13 were 69 to 77 (μm$^{-1}$), and thus HTP of compound (K122-S2) was found to be significantly large.

Example 6-2

Into liquid-crystal composition NLC-A (95.2% by weight), compound (K122-S2) (4.80% by weight) obtained in Example 2 was completely dissolved by being heated and stirred at 100° C. for 2 minutes to obtain liquid-crystal composition CLC-B2.

A phase transition temperature (° C.) of liquid-crystal composition CLC-B2 was N* 70.7 BP 73.6 I.

Example 6-3

Preparation of Monomer-Liquid-Crystal Mixture

As a mixture of a liquid-crystal composition and a polymerizable monomer, liquid-crystal composition MLC-B2 was prepared, in which 88.8% by weight of liquid-crystal composition CLC-B2, 6.0% by weight of n-dodecylacrylate, 4.8% by weight of 1,4-di(4-(6-(acryloyloxy) dodecyloxy) benzoyloxy)-2-methylbenzene (LCA-12), and as a photopolymerization initiator, 0.4% by weight of 2,2'-dimethoxy phenylacetophenone were mixed. A phase transition temperature (° C.) of liquid-crystal composition MLC-B2 was N* 37.8 BP 43.5 BP+I 45.0 I and I 42.2 BP 36.4 N*.

LCA-12

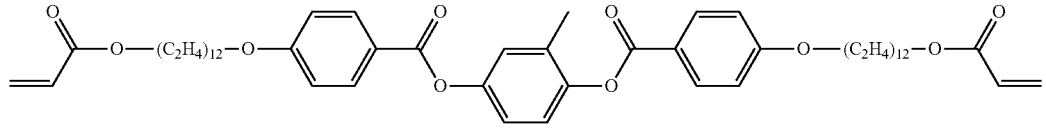

Example 6-4

Preparation of Polymer-Liquid-Crystal Composite Material

Liquid-crystal composition MLC-B2 was interposed between a comb-like electrode and a facing glass substrate (provided with no electrode) each substrate subjected to no alignment treatment (cell thickness: 8 μm), and the resulting cell was heated to a blue phase at 38° C. In the state, the resulting assembly was irradiated with ultraviolet light (ultraviolet light intensity: 23 mWcm$^{-2}$ (365 nm)) for 1 minute to perform a polymerization reaction.

Even if the thus obtained polymer-liquid-crystal composite material (PSBP-B2) was cooled to room temperature, the material maintained an optically isotropic liquid-crystal phase.

In addition, as shown in FIG. 1, in electrodes of the comb-like electrode substrate, electrode 1 extended rightward from an electrode part for connection on a left side, and electrode 2 extended leftward from an electrode part for connection on a right side were alternately arranged. Accordingly, when a potential difference exists between electrode 1 and electrode 2, on the comb-like electrode substrate as shown in FIG. 1, when attention is focused on one electrode, a state can be provided in which electric fields in two directions, an upper direction and a lower direction, on a drawing exist.

Example 6-5

Figure 2:
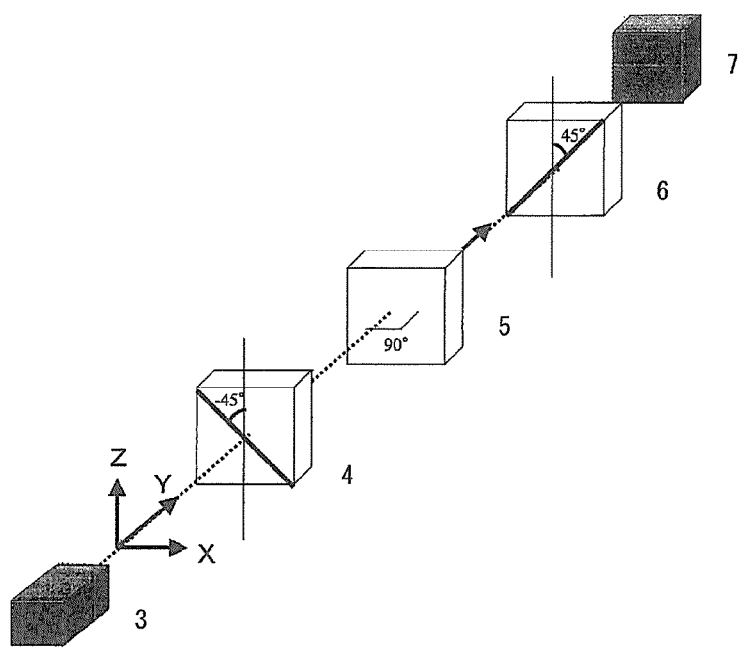
FIG. 2 shows an optical system used in Examples.

The cell obtained in Example 6-4 in which polymer-liquid-crystal composite material PSBP-B2 was interposed therebetween was set to an optical system shown in FIG. 2, and an electrooptical characteristics were measured. In FIG. 2, reference sign "3" represent a light source, reference sign "4" represent a polarizer, reference sign "5" represent a comb-like electrode cell, reference sign "6" represent an analyzer, and reference sign "7" represent a photodetector. A white light source for a polarizing microscope (ECLIPSE LV100POL, made by NIKON Corporation) was used as a light source to adjust an angle incident to the cell to be perpendicular to a cell face, and the cell was set to the optical system such that a line direction of a comb-like electrode formed an angle of 45 degrees to a polarizer and an analyzer, respectively. A relationship between an applied voltage and transmittance was investigated at room temperature. When a rectangular wave having 45 V was applied thereto, the transmittance became 87% and transmitted light intensity was saturated. Contrast was 1,474.

Example 7-1

Into liquid-crystal composition NLC-A (97.5% by weight), compound (K207-S1) (2.50% by weight) obtained in Example 2 was heated and dissolved at 100° C. to obtain liquid-crystal composition CLC-C1. On the occasion, a heating time needed for obtaining liquid-crystal composition CLC-C1 in which the compound was completely dissolved into the composition was 2 minutes.

A selective reflection wavelength (λ) of liquid-crystal composition CLC-C1 was 430.3 (nm). Average refractive index <n> of liquid-crystal composition NLC-A was 1.56. HTP of compound (K207-S1) calculated from the values was 145 (μm$^{-1}$).

Example 7-2

Into liquid-crystal composition NLC-A (95.2% by weight), compound (K207-S1) (4.80% by weight) obtained in Example 2 was heated and dissolved at 100° C. for 2 minutes to obtain liquid-crystal composition CLC-C2.

A phase transition temperature (° C.) of liquid-crystal composition CLC-C2 was N* 63.6 BP 66.0 I.

Example 7-3

Preparation of Monomer-Liquid-Crystal Mixture

As a mixture of a liquid-crystal composition and a polymerizable monomer, liquid-crystal composition MLC-C2 was prepared, in which 88.8% by weight of liquid-crystal composition CLC-C2, 6.0% by weight of n-dodecylacrylate and 4.8% by weight of 1,4-di(4-(6-(acryloyloxy)dodecyloxy)benzoyloxy)-2-methylbenzene (LCA-12), and as a photopolymerization initiator, 0.4% by weight of 2,2'-dimethoxy phenylacetophenone were mixed. A phase transition temperature (° C.) of liquid-crystal composition MLC-C2 was N* 40.2 BP 43.5 BP+I 45.1 I and I 43.4 I+BP 41.4 BP 37.6 N*.

Example 7-4

Preparation of Polymer-Liquid-Crystal Composite Material

Liquid-crystal composition MLC-C2 was interposed between a comb-like electrode substrate and a facing glass substrate (provided with no electrode) each subjected to no alignment treatment (cell thickness: 8 μm), and the resulting cell was heated to a blue phase at 40.4° C. In the state, the resulting assembly was irradiated with ultraviolet light (ultraviolet light intensity: 23 mWcm$^{-2}$ (365 nm)) for 1 minute to perform a polymerization reaction.

Even if the thus obtained polymer-liquid-crystal composite material (PSBP-C2) was cooled to room temperature, the material maintained an optically isotropic liquid-crystal phase.

In addition, as shown in FIG. 1, in electrodes of the comb-like electrode substrate, electrode 1 extended rightward from an electrode part for connection on a left side, and electrode 2 extended leftward from an electrode part for connection on a right side were alternately arranged. Accordingly, when a potential difference exists between electrode 1 and electrode 2, on the comb-like electrode substrate as shown in FIG. 1, when attention is focused on one electrode, a state can be provided in which electric fields in two directions, an upper direction and a lower direction, on a drawing exist.

Example 7-5

The cell obtained in Example 7-4 in which polymer-liquid-crystal composite material PSBP-C2 was interposed therebetween was set to an optical system shown in FIG. 2, and an electrooptical characteristics were measured. A white light source for a polarizing microscope (ECLIPSE LV100POL, made by NIKON Corporation) was used as a light source to adjust an angle incident to the cell to be perpendicular to a cell face, and the cell was set to the optical system such that a line direction of a comb-like electrode formed an angle of 45 degrees to a polarizer and an analyzer, respectively. A relationship between an applied voltage and transmittance was investigated at room temperature. When a rectangular wave having 45 V was applied thereto, the transmittance became 87% and transmitted light intensity was saturated. Contrast was 1,912.

Example 8-1

Liquid-crystal composition NLC-D was prepared by mixing liquid-crystal compounds shown in the figure below at ratios described below.
Liquid-Crystal Composition NLC-D

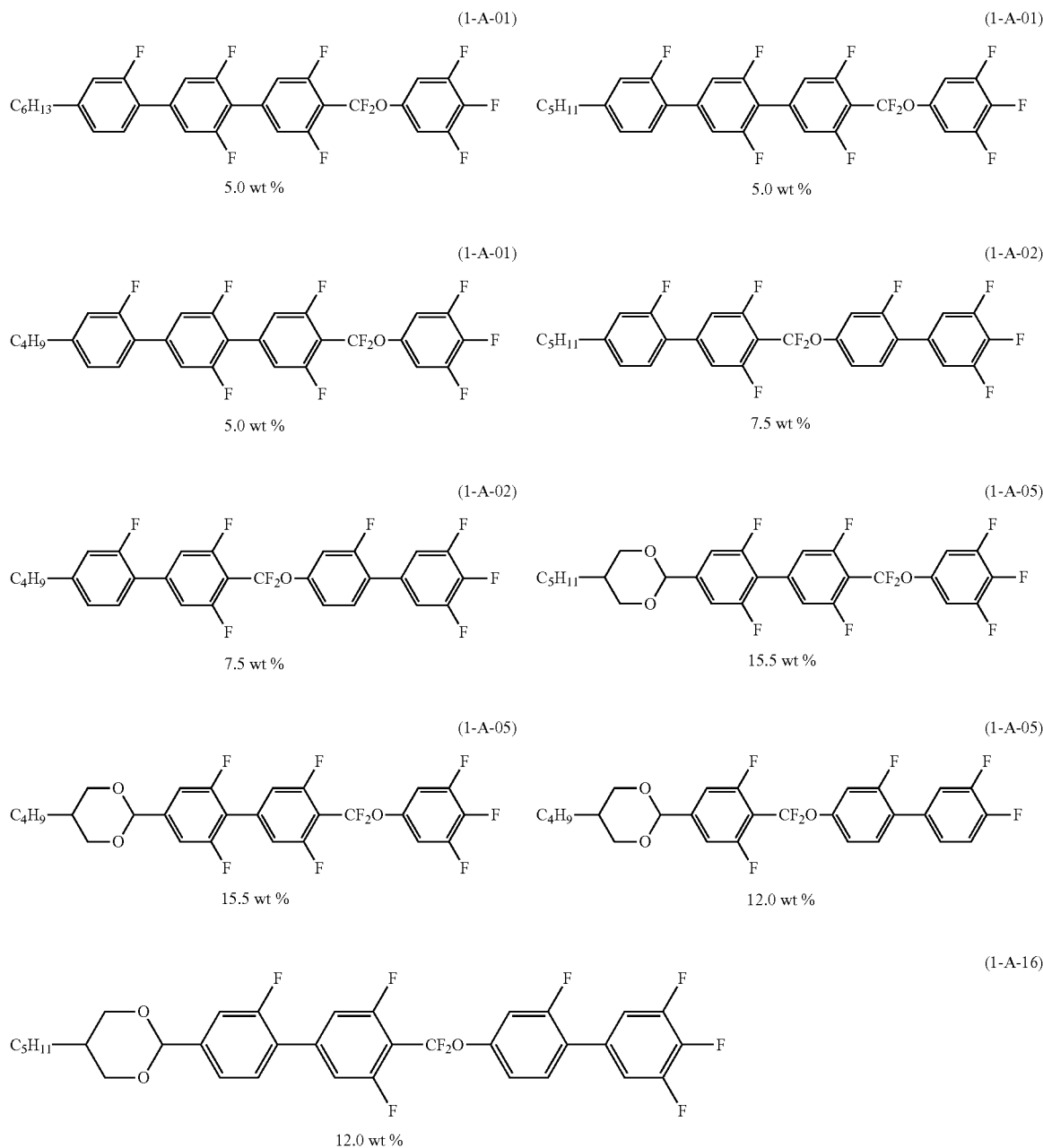

(1-A-02)

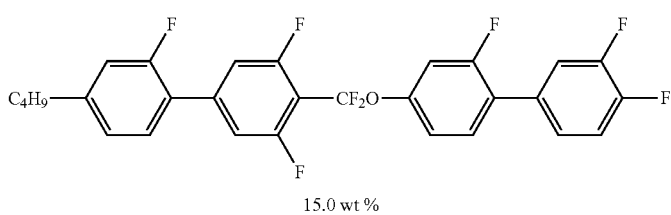

15.0 wt %

A phase transition temperature (° C.) of liquid-crystal composition NLC-D was N 110.6-111.8 I.

Into liquid-crystal composition NLC-D (97.5% by weight), compound (K122-S2) (2.50% by weight) obtained in Example 2 was heated and dissolved at 100° C. to obtain liquid-crystal composition CLC-D1. On the occasion, a heating time needed for obtain liquid-crystal composition CLC-D1 in which the compound was completely dissolved into the composition was 2 minutes.

A selective reflection wavelength (λ) of liquid-crystal composition CLC-D1 was 457.5 (nm). Average refractive index <n> of liquid-crystal composition NLC-D was 1.51. HTP of compound (K122-S2) calculated from the values was 137 ($\mu m^{-1}$).

Example 8-2

Into liquid-crystal composition NLC-D (94.8% by weight), compound (K122-S2) (5.20% by weight) obtained in Example 2 was heated and dissolved at 100° C. for 5 minutes to obtain liquid-crystal composition CLC-D2. A phase transition temperature (° C.) of liquid-crystal composition CLC-D2 was N* 101.3 to 101.6 BP 103.1 BP+I 104.5 I.

Example 8-3

Preparation of Monomer-Liquid-Crystal Mixture

As a mixture of a liquid-crystal composition and a polymerizable monomer, liquid-crystal composition MLC-D2 was prepared, in which 88.4% by weight of liquid-crystal composition CLC-D2, 6.2% by weight of n-dodecylacrylate and 5.0% by weight of 1,4-di(4-(6-(acryloyloxy)dodecyloxy) benzoyloxy)-2-methylbenzene (LCA-12), and as a photopolymerization initiator, 0.4% by weight of 2,2'-dimethoxy phenylacetophenone were mixed. A phase transition temperature (° C.) of liquid-crystal composition MLC-D2 was N* 67.5 to 68.1 BP 72.5 BP+I 73.4 I and I 72.4 65.9 N*.

Example 8-4

Preparation of Polymer-Liquid-Crystal Composite Material

Liquid-crystal composition MLC-D2 was interposed between a comb-like electrode substrate and a facing glass substrate (provided with no electrode) each subjected to no alignment treatment (cell thickness: 8 μm), and the resulting cell was heated to a blue phase at 68.0° C. In the state, the resulting assembly was irradiated with ultraviolet light (ultraviolet light intensity: 23 mWcm$^{-2}$ (365 nm)) for 1 minute to perform a polymerization reaction.

Even if the thus obtained polymer-liquid-crystal composite material (PSBP-D2) was cooled to room temperature, the material maintained an optically isotropic liquid-crystal phase.

In addition, as shown in FIG. 1, in electrodes of the comb-like electrode substrate, electrode 1 extended rightward from an electrode part for connection on a left side, and electrode 2 extended leftward from an electrode part for connection on a right side were alternately arranged. Accordingly, when a potential difference exists between electrode 1 and electrode 2, on the comb-like electrode substrate as shown in FIG. 1, when attention is focused on one electrode, a state can be provided in which electric fields in two directions, an upper direction and a lower direction, on a drawing exist.

Example 8-5

The cell obtained in Example 8-4 in which polymer-liquid-crystal composite material PSBP-D2 was interposed therebetween was set to an optical system shown in FIG. 2, and an electrooptical characteristics were measured. A white light source for a polarizing microscope (ECLIPSE LV100POL, made by NIKON Corporation) was used as a light source to adjust an angle incident to the cell to be perpendicular to a cell face, and the cell was set to the optical system such that a line direction of a comb-like electrode formed an angle of 45 degrees to a polarizer and an analyzer polarizing plate, respectively. A relationship between an applied voltage and transmittance was investigated at room temperature. When a rectangular wave having 45 V was applied thereto, the transmittance became 89% and transmitted light intensity was saturated. Contrast was 1,107.

As described above, the chiral compound of the invention has features of large HTP, a low melting point and good compatibility with the liquid-crystal composition. The optical element in which the chiral compound of the invention is used has a high maximum temperature in the liquid-crystal phase and high contrast to allow a low voltage drive, and has high contrast, and is superior to the device according to a conventional technology.

INDUSTRIAL APPLICABILITY

Specific examples of a method for utilizing the invention include an optical element such as a display device in which a polymer-liquid-crystal composite is used.

1: Electrode 1
2: Electrode 2
3: Light source
4: Polarizer
5: Comb-like electrode cell
6: Analyzer
7: Photodetector

What is claimed is:

1. A liquid-crystal composition, comprising at least one chiral compound represented by general formula (K1) or (K2) and at least one achiral liquid-crystal component:

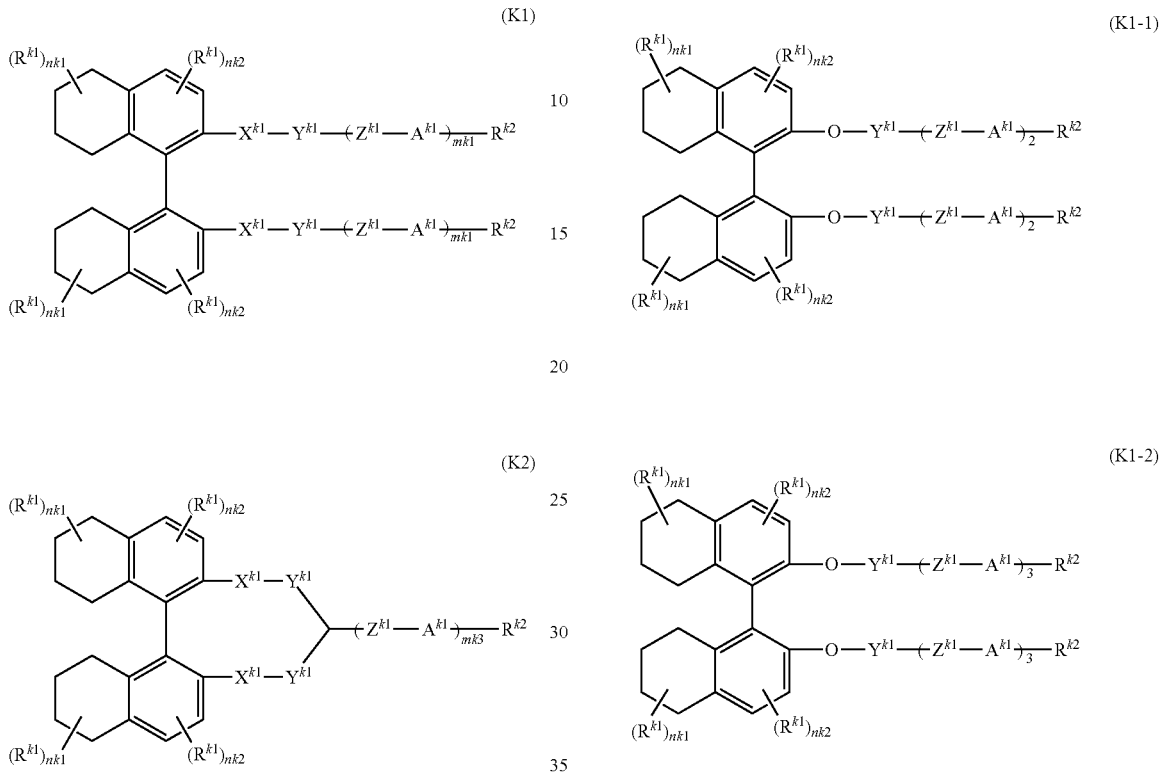

wherein, in formulas (K1) and (K2),
$R^{k1}$ is halogen, cyano, —$SF_5$ or alkyl having 1 to 5 carbons, at least one of —$CH_2$— in $R^{k1}$ may be replaced by —O—, and at least one of hydrogen in $R^{k1}$ may be replaced by halogen;
$R^{k2}$ is halogen, cyano, —$SF_5$ or alkyl having 1 to 20 carbons, at least one of —$CH_2$— in $R^{k2}$ may be replaced by —O—, and at least one of hydrogen in $R^{k2}$ may be replaced by halogen;
ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl, pyridine-2,5-diyl or 1,4-bicyclo-(2,2,2)-octylene, and at least one of hydrogen in the rings may be replaced by halogen;
$X^{k1}$ is a single bond, —O—, —CO—, —COO—, —OCO—, —$OCH_2$—, —$CH_2O$—, —$CF_2O$—, —$OCF_2$—, —CH=CH—, —$CF_2CF_2$—, —CF=CF— or —C≡C—;
$Y^{k1}$ is a single bond or —$(CH_2)_n$—, and n is an integer from 1 to 20;
$Z^{k1}$ is a single bond or alkylene having 1 to 10 carbons, at least one of —$CH_2$— in $Z^{k1}$ may be replaced by —O—, —COO—, —OCO—, —CH=CH—, —CF=CF— or —C≡C—, and at least one of hydrogen in $Z^{k1}$ may be replaced by halogen;
mk1 is an integer from 2 to 4; nk1 and nk2 is an integer from 0 to 2; and
when a plurality of $R^{k1}$, $R^{k2}$, $A^{k1}$, $A^{k2}$, $X^{k1}$, $Y^{k1}$, $Z^{k1}$, mk1, nk1 or nk2 exist, the plurality may be identical or different each other.

2. A liquid-crystal composition, comprising at least one chiral compound selected from compounds represented by general formulas (K1-1) to (K1-6) and at least one achiral liquid-crystal component:

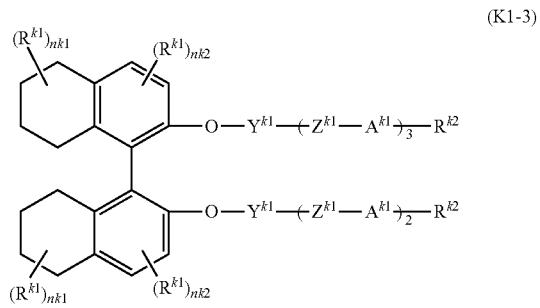

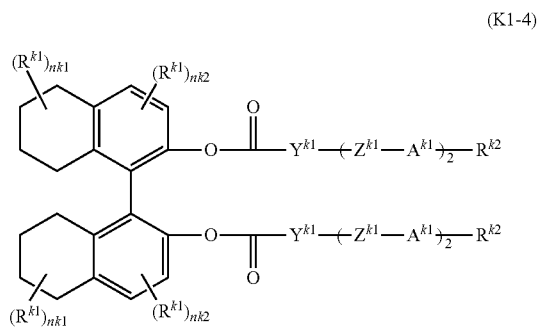

-continued (K1-5)

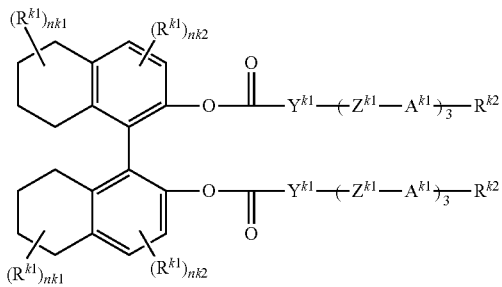
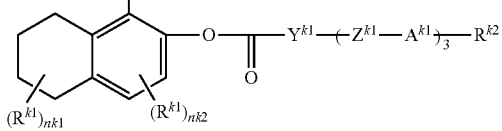

(K2-1)

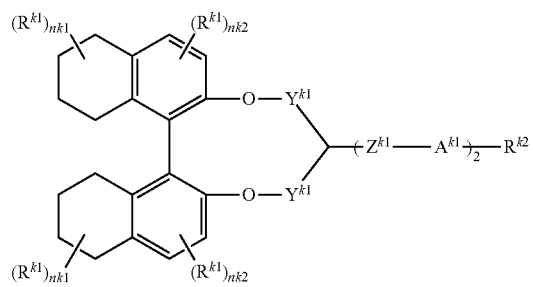
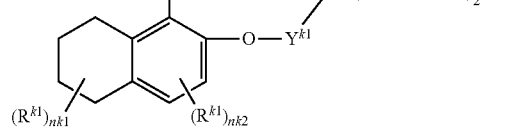

(K1-6)

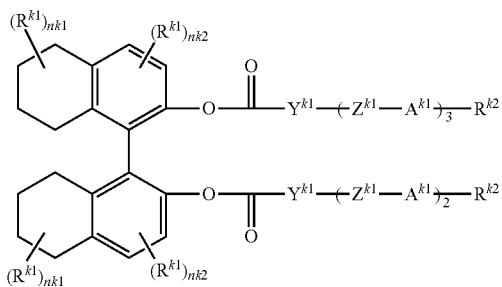
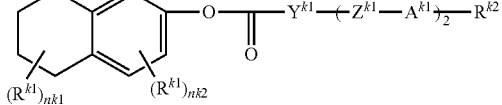

(K2-2)

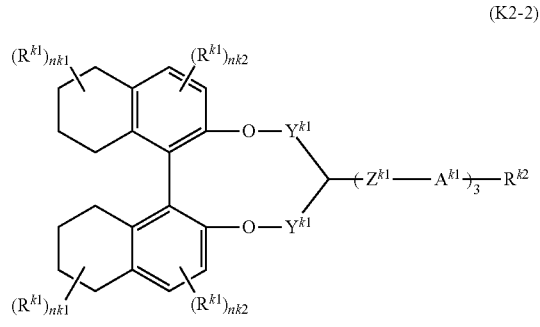

wherein, in formulas (K1-1) to (K1-6),
- $R^{k1}$ is halogen, cyano, —$SF_5$ or alkyl having 1 to 5 carbons, at least one of —$CH_2$— in $R^{k1}$ may be replaced by —O—, and at least one of hydrogen in $R^{k1}$ may be replaced by halogen;
- $R^{k2}$ is halogen, cyano, —$SF_5$ or alkyl having 1 to 20 carbons, at least one of —$CH_2$— in $R^{k2}$ may be replaced by —O—, and at least one of hydrogen in $R^{k2}$ may be replaced by halogen;
- ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl, pyridine-2,5-diyl or 1,4-bicyclo-(2,2,2)-octylene, and at least one of hydrogen in the rings may be replaced by halogen;
- $Y^{k1}$ is a single bond or —$(CH_2)_n$—, and n is an integer from 1 to 20;
- $Z^{k1}$ is a single bond or alkylene having 1 to 10 carbons, at least one of —$CH_2$— in $Z^{k1}$ may be replaced by —O—, —COO—, —OCO—, —CH=CH—, —CF=CF— or —C≡C— and at least one of hydrogen in $Z^{k1}$ may be replaced by halogen;
- nk1 and nk2 are an integer from 0 to 2; and
- when a plurality of $R^{k1}$, $R^{k2}$, $A^{k1}$, $A^{k2}$, $Y^{k1}$, $Z^{k1}$, nk1 or nk2 exist, the plurality may be identical or different each other.

3. A liquid-crystal composition, comprising at least one chiral compound represented by general formula (K2-1) or (K2-2) and at least one achiral liquid-crystal component:

wherein, in formulas (K2-1) to (K2-2),
- $R^{k1}$ is halogen, cyano, —$SF_5$ or alkyl having 1 to 5 carbons, at least one of —$CH_2$— in the alkyl may be replaced by —O—, and at least one of hydrogen in the alkyl may be replaced by halogen;
- $R^{k2}$ is halogen, cyano, —$SF_5$ or alkyl having 1 to 20 carbons, at least one of —$CH_2$— in the alkyl may be replaced by —O—, and at least one of hydrogen in the alkyl may be replaced by halogen;
- ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl, pyridine-2,5-diyl or 1,4-bicyclo-(2,2,2)-octylene, and at least one of hydrogen in the rings may be replaced by halogen;
- $Y^{k1}$ is a single bond or —$(CH_2)_n$—, and n is an integer from 1 to 20;
- $Z^{k1}$ is a single bond or alkylene having 1 to 10 carbons, at least one of —$CH_2$— in the alkylene may be replaced by —O—, —COO—, —OCO—, —CH=CH—, —CF=CF— or —C≡C—, and at least one of hydrogen in the alkylene may be replaced by halogen;
- nk1 or nk2 is an integer from 0 to 2; and
- when a plurality of $R^{k1}$, $R^{k2}$, $A^{k1}$, $A^{k2}$, $Y^{k1}$, nk1 or nk2 exist, the plurality may be identical or different each other.

4. A liquid-crystal composition, comprising at least one chiral compound represented by general formula (K1-1-1), (K1-1-2), (K1-2-1), (K1-2-2), (K1-4-1), (K1-4-2), (K1-5-1) or (K1-5-2) and at least one achiral liquid-crystal component:

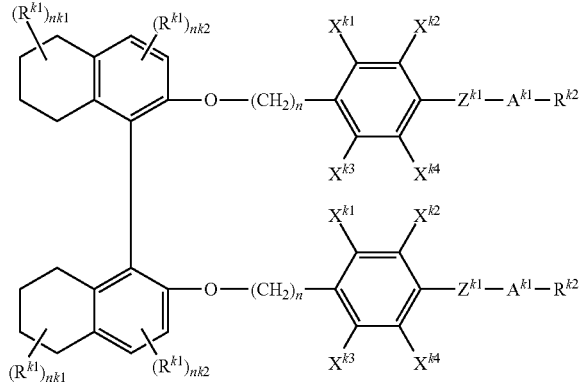
(K1-1-1)
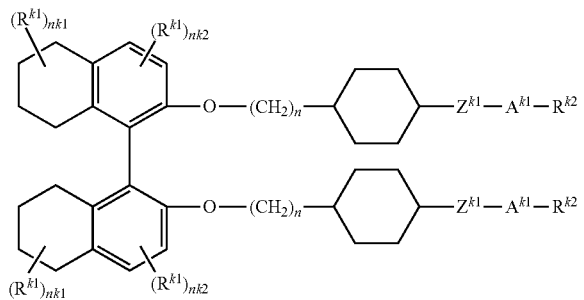
(K1-1-2)
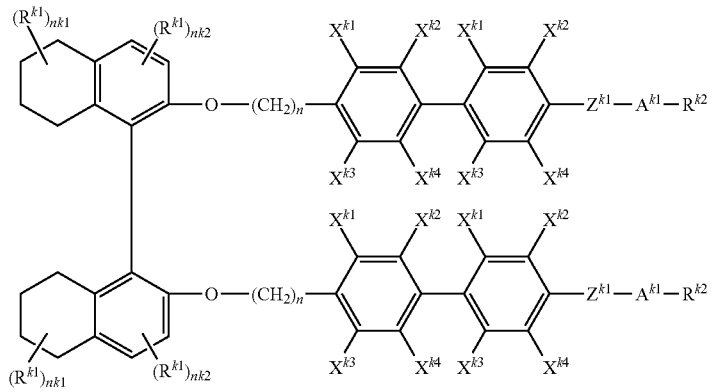
(K1-2-1)
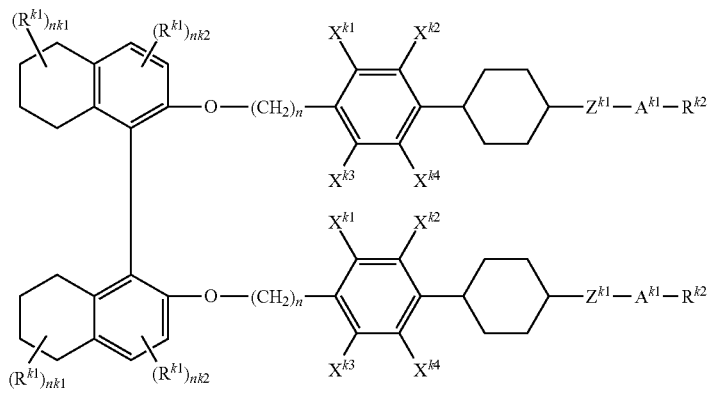
(K1-2-2)

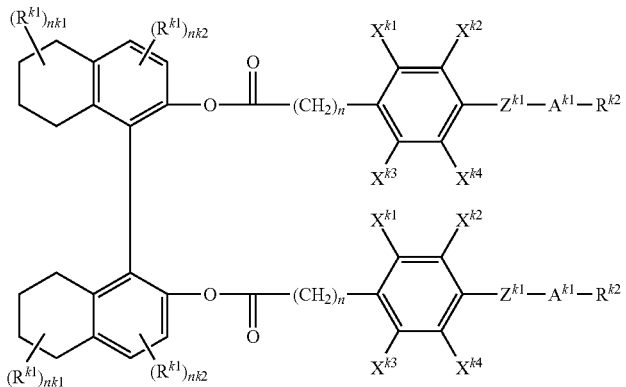
(K1-4-1)
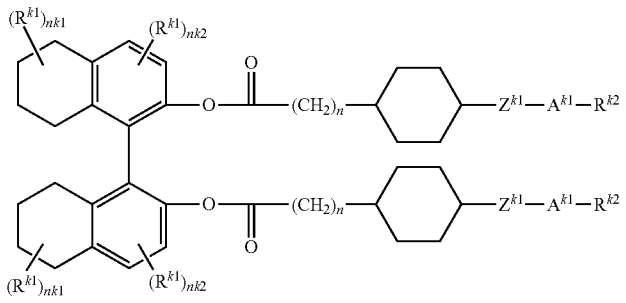
(K1-4-2)
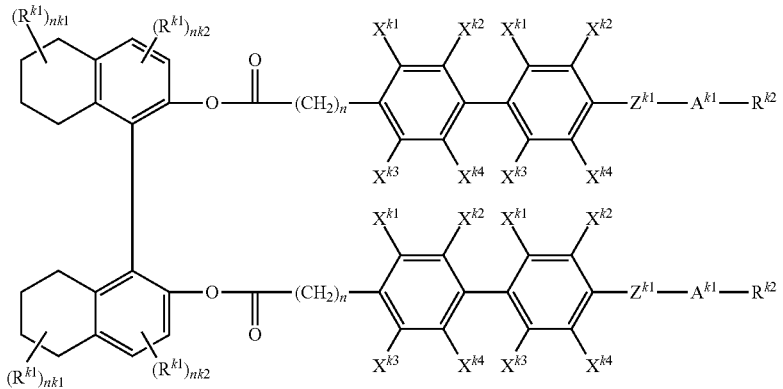
(K1-5-1)
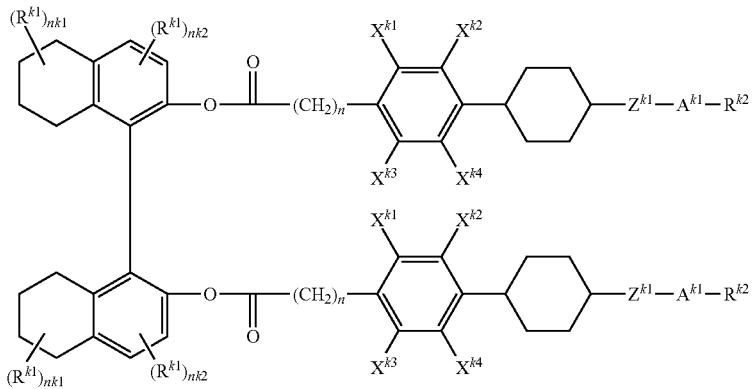
(K1-5-2)

wherein, in the formulas, $R^{k1}$ is hydrogen, halogen, cyano or alkyl having 1 to 5 carbons, and at least one of hydrogen in the alkyl may be replaced by halogen;

$R^{k2}$ is hydrogen, halogen, cyano or alkyl having 1 to 20 carbons, and at least one of hydrogen in the alkyl may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl or pyridine-2,5-diyl, and at least one of hydrogen in the rings may be replaced by halogen;

n is an integer from 0 to 10;

$Z^{k1}$ is a single bond, alkylene having 1 to 10 carbons, —$CH_2O$—, —$OCH_2$—, —$CF_2O$—, —$OCF_2$—, —COO—, —OCO—, —CH=CH—, —CF=CF— or —C≡C—;

$X^{k1}$, $X^{k2}$, $X^{k3}$ and $X^{k4}$ are independently hydrogen or fluorine, wherein three or more fluorine cannot exist at the same time in $X^{k1}$, $X^{k2}$, $X^{k3}$ and $X^{k4}$;

nk1 or nk2 is an integer from 0 to 2; and when a plurality of $R^{k1}$, $R^{k2}$, $A^{k1}$, $Z^{k1}$, nk1 or nk2 exist, the plurality may be identical or different each other.

5. A liquid-crystal composition, comprising at least one chiral compound represented by general formula (K2-1-1), (K2-1-2), (K2-2-1), (K2-2-2) or (K2-2-3) and at least one achiral liquid-crystal component:

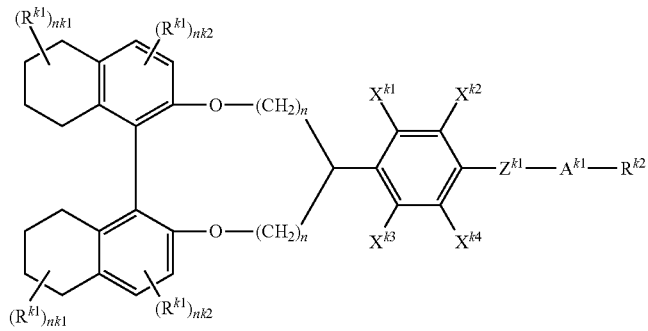
(K2-1-1)

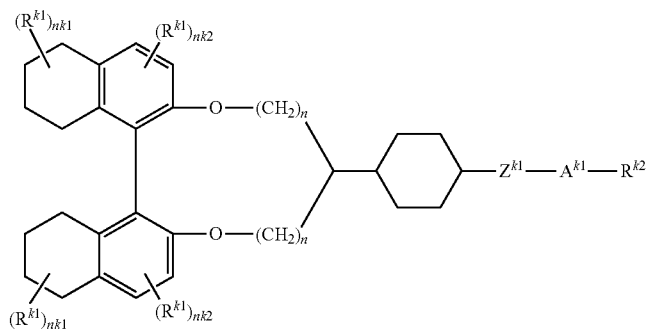
(K2-1-2)

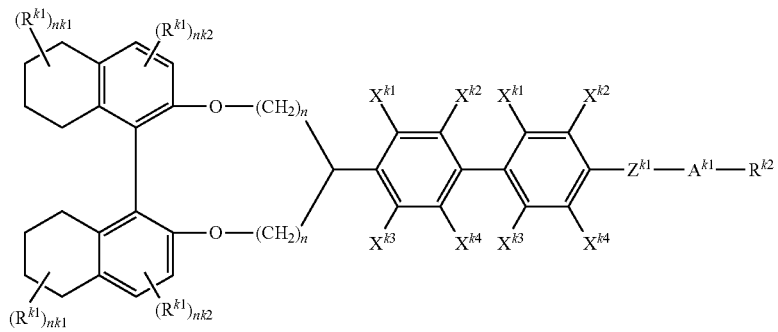
(K2-2-1)

-continued

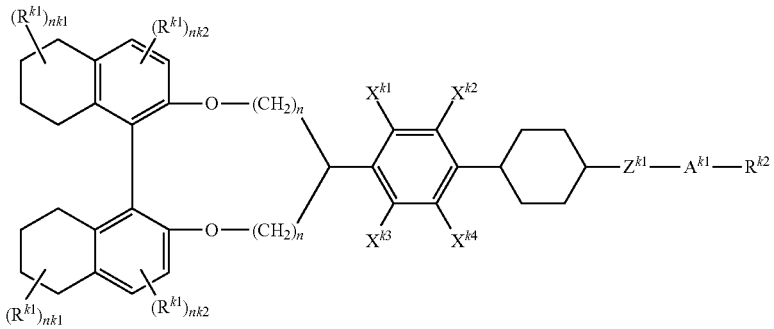

(K2-2-2)

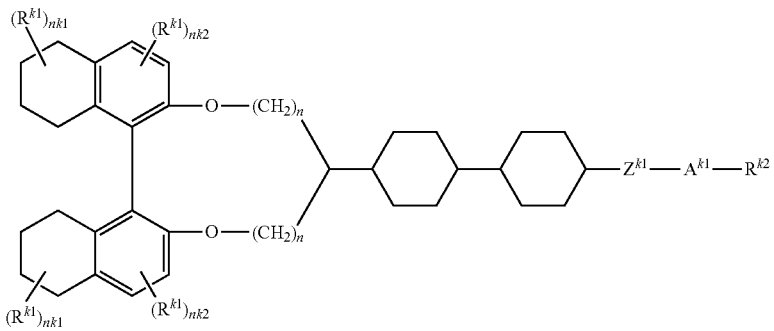

(K2-2-3)

wherein, in formulas (K2-1-1) to (K2-2-3), $R^{k1}$ is hydrogen, halogen, cyano or alkyl having 1 to 5 carbons, and at least one of hydrogen in the alkyl may be replaced by halogen;

$R^{k2}$ is hydrogen, halogen, cyano or alkyl having 1 to 20 carbons, and at least one of hydrogen in the alkyl may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl or pyridine-2,5-diyl, and at least one of hydrogen in the rings may be replaced by halogen;

n is an integer from 0 to 10;

$Z^{k1}$ is a single bond, alkylene having 1 to 10 carbons, —CH$_2$O—, —OCH$_2$—, —CF$_2$O—, —OCF$_2$—, —COO—, —OCO—, —CH=CH—, —CF=CF— or —C≡C—;

$X^{k1}$, $X^{k2}$, $X^{k3}$ and $X^{k4}$ are independently hydrogen or fluorine, wherein three or more fluorine cannot exist at the same time in $X^{k1}$, $X^{k3}$ and $X^{k4}$;

nk1 or nk2 is an integer from 0 to 2; and when a plurality of $R^{k1}$, $R^{k2}$, $A^{k1}$, $Z^{k1}$, nk1 or nk2 exist, the plurality may be identical or different each other.

6. The liquid-crystal composition according to claim 1, containing at least one compound represented by general formula (1-A) is contained in the achiral liquid-crystal component:

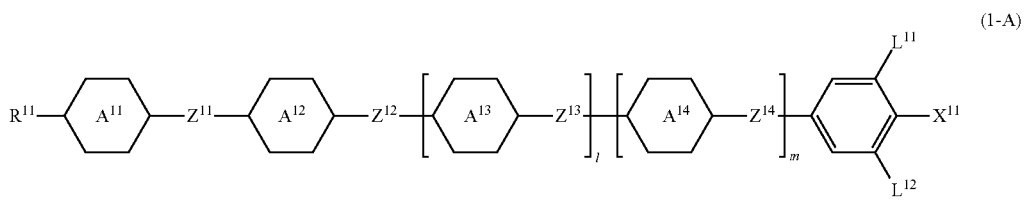

(1-A)

wherein, in general formula (1-A), $R^{11}$ is hydrogen and alkyl having 1 to 20 carbons, at least one —CH$_2$— in the alkyl may be replaced by —O—, —S—, —COO—, —OCO— or —C≡C—, but a case where two successive —CH$_2$— are replaced by —O— is excluded, and at least one of hydrogen in the alkyl may be replaced by halogen; ring $A^{11}$, ring $A^{12}$, ring $A^{13}$ and ring $A^{14}$ are independently 1,4-phenylene, 1,3-dioxane-2,5-diyl, tetrahydropyran-2,5-diyl, tetrahydropyran-3,6-diyl, pyrimidine-2,5-diyl, pyridine-2,5-diyl, naphthalene-2,6-diyl, bicyclo[2,2,2]octane-1,4-diyl, 1,4-cyclohexylene or 2,6,7-trioxabicyclo[2,2,2]octane-1,4-diyl, and at least one of hydrogen in the rings may be replaced by halogen; $Z^{11}$, $Z^{12}$, $Z^{13}$ and $Z^{14}$ are independently a single bond and alkylene having 1 to 4 carbons, at least one of —CH$_2$— in the alkylene may be replaced by —O—, —S—, —COO—, —OCO—, —CF$_2$O—, —OCF$_2$—, —CH=CH—, —CF=CF— or —C≡C—, and at least one of hydrogen in the alkylene may be replaced by halogen; $L^{11}$ and $L^{12}$ are each independently hydrogen or halogen; $X^{11}$ is halogen, —C≡N, —N=C=S, —C≡C—C≡N, —SF$_5$, —CHF$_2$, —CF$_3$, —CF$_2$CH$_2$F, —CF$_2$CHF$_2$, —CF$_2$CF$_3$, —(CF$_2$)$_3$—F, —CF$_2$CHFCF$_3$, —CHFCF$_2$CF$_3$, —(CF$_2$)$_4$—F, —(CF$_2$)$_5$—F, —OCHF$_2$, —OCF$_3$, —OCF$_2$CH$_2$F, —OCF$_2$CHF$_2$, —OCH$_2$CF$_3$, —OCF$_2$CF$_3$, —O—(CF$_2$)$_3$—F, —OCF$_2$CHFCF$_3$, —OCHFCF$_2$CF$_3$, —O—(CF$_2$)$_4$—F, —O—(CF$_2$)$_5$—F, —CH=CF$_2$, —CH=CHCF$_3$ or —CH=CHCF$_2$CF$_3$; and l and m are independently 0 or 1.

7. The liquid-crystal composition according to claim 6, containing a compound represented by general formula (1-A) in an amount of 50 to 100% by weight in the achiral liquid-crystal component.

8. The liquid-crystal composition according to claim 6, containing a compound represented by general formula (1-A) in an amount of 50 to 100% by weight in the achiral liquid-crystal component, and further containing at least one chiral compound selected from compounds represented by general formulas (K11) to (K15):

(K11)
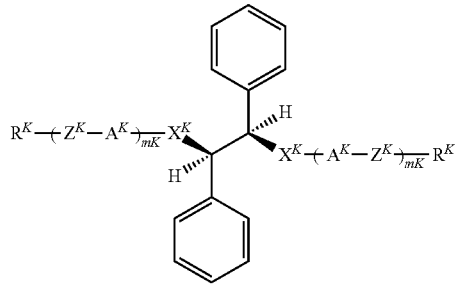

(K12)
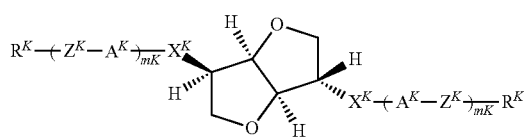

(K13)
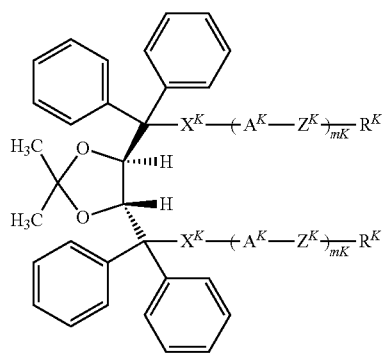

(K14)
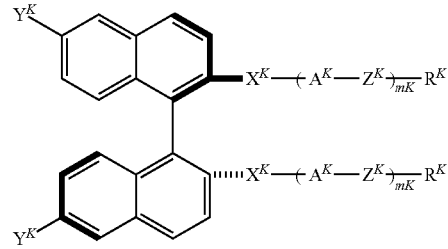

(K15)
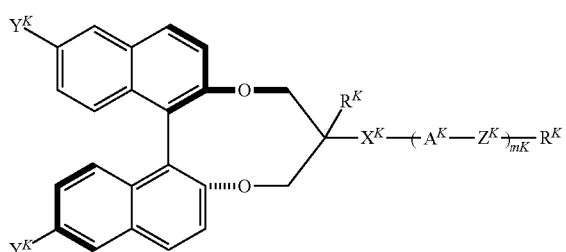

wherein, in formulas (K11) to (K15), $R^K$ is independently hydrogen, halogen, —C≡N, —N=C=O, —N=C=S or alkyl having 1 to 20 carbons, at least one of —CH$_2$— in the alkyl may be replaced by —O—, —S—, —COO—, —OCO—, —CH=CH—, —CF=CF— or —C≡C—, and at least one of hydrogen in the alkyl may be replaced by halogen;

$A^K$ is independently an aromatic 6-membered to 8-membered ring, nonaromatic 3-membered to 8-membered ring or a condensed ring having 9 to 20 carbons, at least one of hydrogen in the rings may be replaced by halogen, alkyl or haloalkyl each having 1 to 3 carbons, —CH$_2$— in the ring may be replaced by —O—, —S— or —NH—, and —CH= may be replaced by —N=;

$Y^K$ is independently hydrogen, halogen, alkyl having 1 to 3 carbons, haloalkyl having 1 to 3 carbons, an aromatic 6-membered to 8-membered ring, a non-aromatic 3-membered to 8-membered ring or a condensed ring having 9 to 20 carbons, at least one of hydrogen in the rings may be replaced by halogen, alkyl or haloalkyl each having 1 to 3 carbons, —CH$_2$— may be replaced by —O—, —S— or —NH—, and —CH= may be replaced by —N=;

$Z^K$ is independently a single bond or alkylene having 1 to 8 carbons, but at least one of —CH$_2$— may be replaced by —O—, —S—, —COO—, —OCO—, —CSO—, —OCS—, —N=N—, —CH=N—, —N=CH—, —CH=CH—, —CF=CF— or —C≡C—, and at least one of hydrogen may be replaced by halogen; $X^K$ is a single bond, —COO—, —OCO—, —CH$_2$O—, —OCH$_2$—, —CF$_2$O—, —OCF$_2$— or —CH$_2$CH$_2$—; and mK is an integer from 1 to 4.

9. The liquid-crystal composition according to claim 1, containing at least one compound represented by any one of general formulas (1-A-01) to (1-A-16) in the achiral liquid-crystal component:

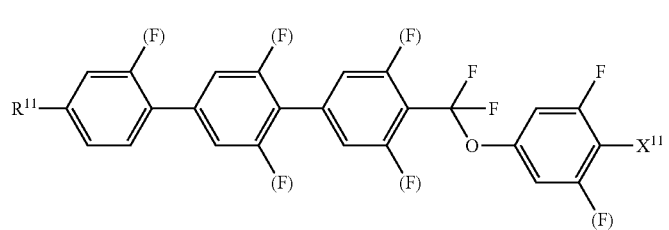
(1-A-01)
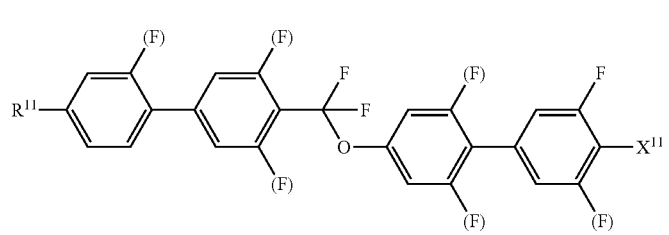
(1-A-02)
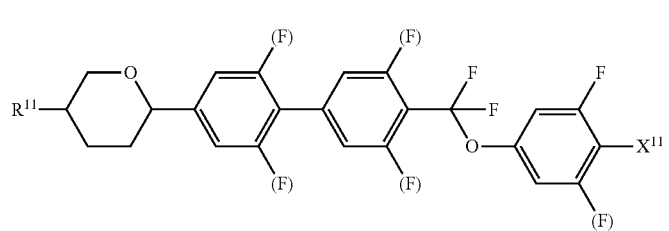
(1-A-03)
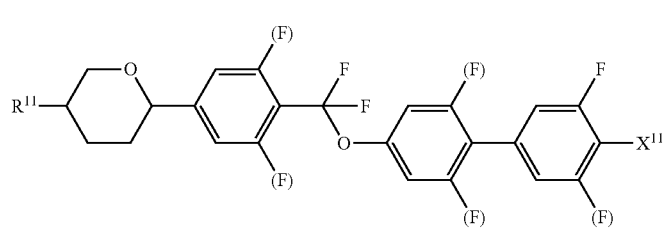
(1-A-04)
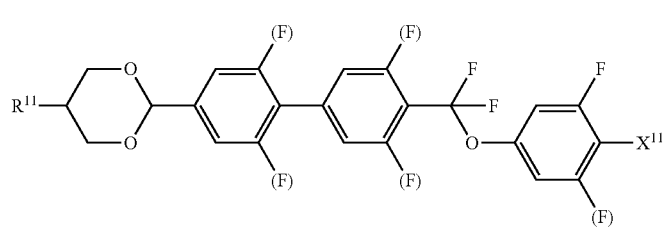
(1-A-05)
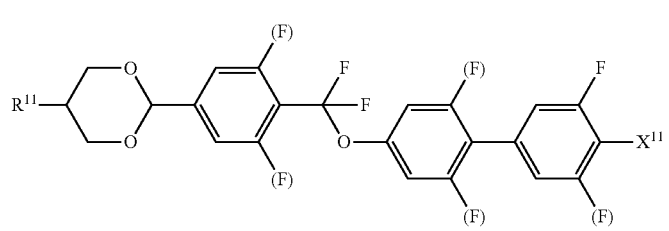
(1-A-06)
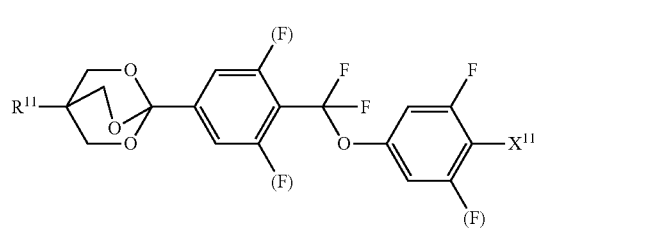
(1-A-07)

-continued
(1-A-08)
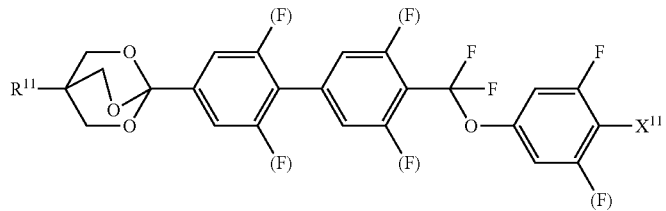
(1-A-09)
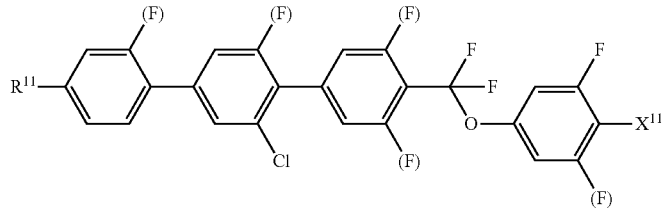
(1-A-10)
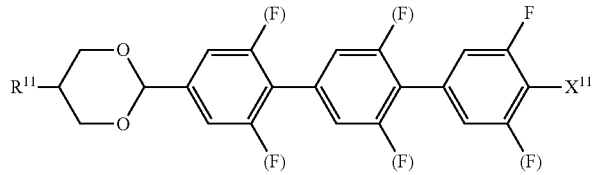
(1-A-11)
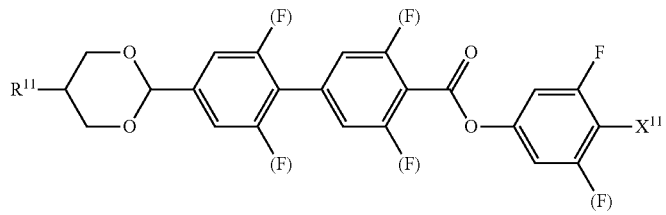
(1-A-12)
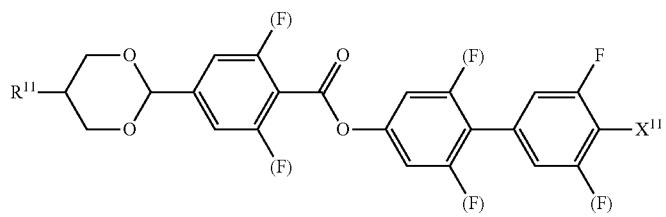
(1-A-13)
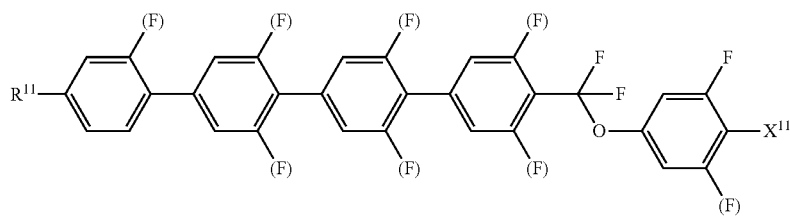
(1-A-14)
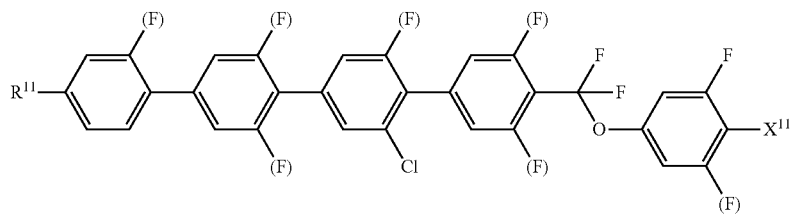

(1-A-15)

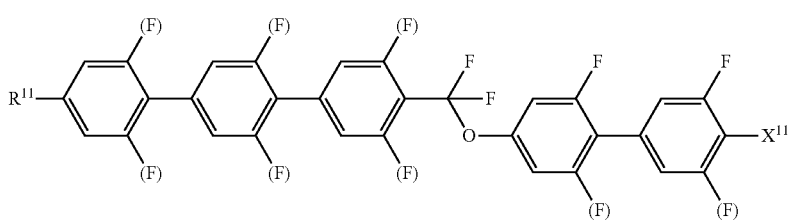

(1-A-16)

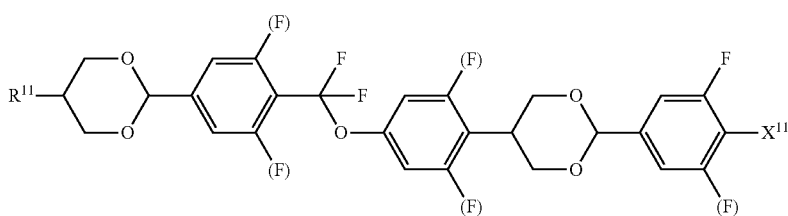

wherein, in formulas (1-A-01) to (1-A-16), $R^{11}$ is hydrogen or alkyl having 1 to 8 carbons, $X^{11}$ is fluorine, chlorine, —C≡N, —CF$_3$, —CHF$_2$, —OCF$_3$, —OCHF$_2$, —OCH$_2$F or —C≡C—CF$_3$, and (F) represents hydrogen or fluorine.

10. The liquid-crystal composition according to claim 9, containing at least one compound represented by any one of general formulas (1-A-01) to (1-A-16) in the achiral liquid-crystal component, wherein a content of the compound is 50 to 100% by weight.

11. The liquid-crystal composition according to claim 9, containing at least one compound represented by any one of general formulas (1-A-01) to (1-A-16) in the achiral liquid-crystal component, and further containing at least one compound represented by general formulas (K11) to (K15) in chiral component K:

(K11)

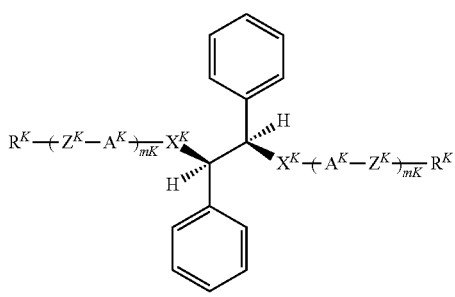

(K12)

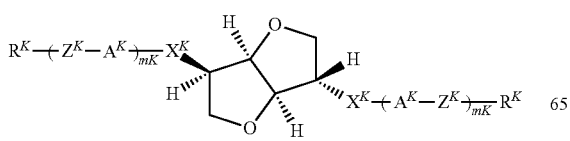

(K13)

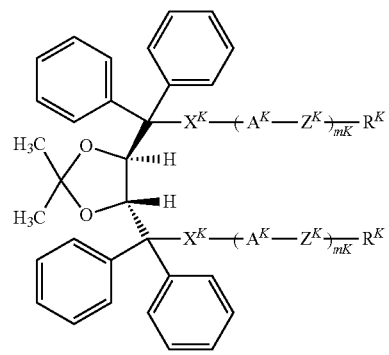

(K14)

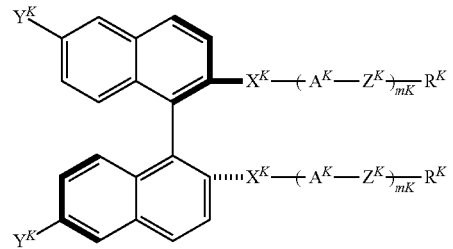

(K15)

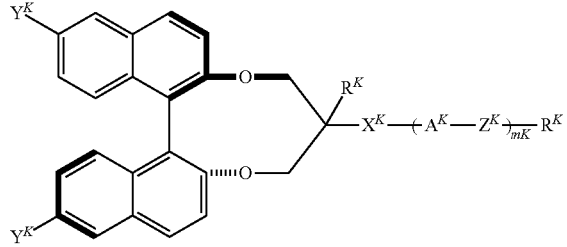

wherein, in formulas (K11) to (K15), $R^K$ is independently hydrogen, halogen, —C≡N, —N=C=O, —N=C=S or alkyl having 1 to 20 carbons, at least one of —CH$_2$— in the alkyl may be replaced by —O—, —S—, —COO—, —OCO—, —CH=CH—, —CF=CF— or —C≡C—, and at least one of hydrogen in the alkyl may be replaced by halogen;

$A^K$ is independently an aromatic 6-membered to 8-membered ring, nonaromatic 3-membered to 8-membered ring or a condensed ring having 9 to 20 carbons, at least one of hydrogen in the rings may be replaced by halogen, alkyl or haloalkyl each having 1 to 3 carbons, —$CH_2$— in the ring may be replaced by —O—, —S— or —NH—, and —CH= may be replaced by —N=;

$Y^K$ is independently hydrogen, halogen, alkyl having 1 to 3 carbons, haloalkyl having 1 to 3 carbons, an aromatic 6-membered to 8-membered ring, a non-aromatic 3-membered to 8-membered ring or a condensed ring having 9 to 20 carbons, at least one of hydrogen in the rings may be replaced by halogen, alkyl or haloalkyl each having 1 to 3 carbons, —$CH_2$— may be replaced by —O—, —S— or —NH—, and —CH= may be replaced by —N=;

$Z^K$ is independently a single bond or alkylene having 1 to 8 carbons, but at least one of —$CH_2$— may be replaced by —O—, —S—, —COO—, —OCO—, —CSO—, —OCS—, —N=N—, —CH=N—, —N=CH—, —CH=CH—, —CF=CF— or —C≡C—, and at least one of hydrogen may be replaced by halogen; $X^K$ is a single bond, —COO—, —OCO—, —$CH_2O$—, —$OCH_2$—, —$CF_2O$—, —$OCF_2$— or —$CH_2CH_2$—; and mK is an integer from 1 to 4.

12. The liquid-crystal composition according to claim 1, wherein a content of the chiral compound is 0.1 to 30% by weight.

13. The liquid-crystal composition according to claim 1, exhibiting a chiral nematic phase of at least 1° C. or more in the temperature range of 20 to 70° C., wherein a helical pitch is 700 nanometers or less at least partially in the temperature range.

14. A monomer-liquid-crystal mixture, containing the liquid-crystal composition according to claim 1 and a polymerizable monomer.

15. The monomer-liquid-crystal mixture according to claim 14, exhibiting a chiral nematic phase of at least 1° C. or more in the temperature range of −20 to 70° C., wherein a helical pitch is 700 nanometers or less at least partially in the temperature range.

16. A polymer-liquid-crystal composite material, obtained by polymerizing the monomer-liquid-crystal mixture according to claim 14, and used in an element driven in the optically isotropic liquid-crystal phase.

17. A polymer-liquid-crystal composite material, obtained by polymerizing the monomer-liquid-crystal mixture according to claim 14 in a non-liquid-crystal isotropic phase or an optically isotropic liquid-crystal phase, and is used for an element driven in the optically isotropic liquid-crystal phase.

18. A liquid-crystal device, having an electrode arranged on one side or both sides, a liquid-crystal composition or a polymer-liquid-crystal composite material arranged between substrates, and an electric field applying means for applying an electric field to the liquid-crystal composition or the polymer-liquid-crystal composite material through the electrode, wherein the polymer-liquid-crystal composite material is according to claim 16.

19. A chiral compound represented by general formula (K1-5-1) or (K1-5-2):

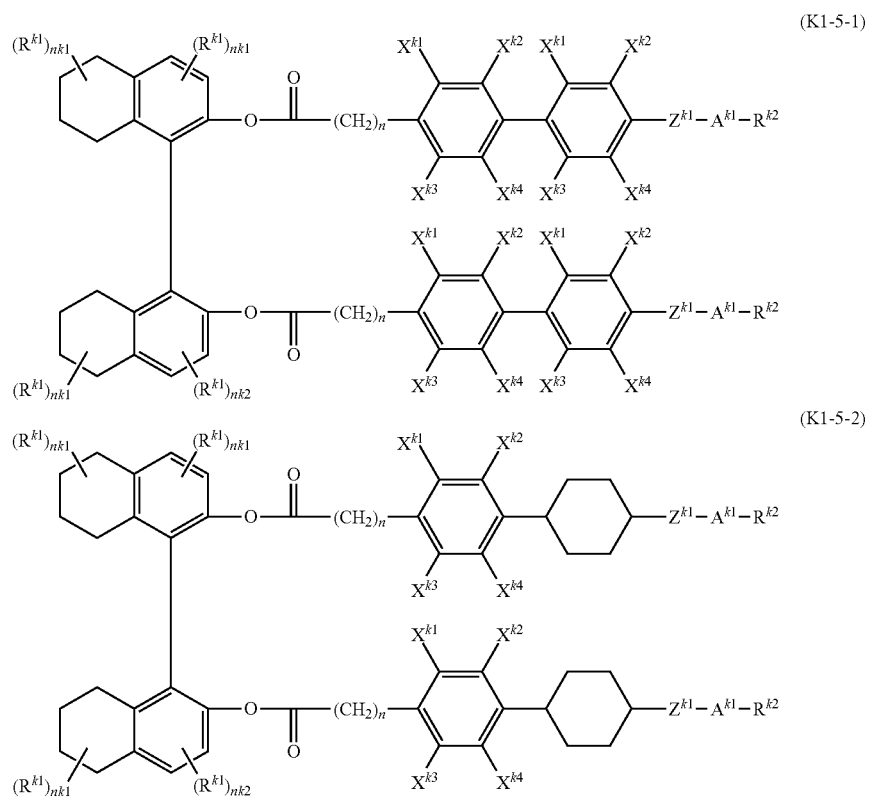

wherein, in the formulas, $R^{k1}$ is hydrogen, halogen, cyano or alkyl having 1 to 5 carbons, and at least one of hydrogen in the alkyl may be replaced by halogen;

$R^{k2}$ is hydrogen, halogen, cyano or alkyl having 1 to 20 carbons, and at least one of hydrogen in the alkyl may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl or pyridine-2,5-diyl, and at least one of hydrogen in the rings may be replaced by halogen;

n is an integer from 0 to 10;

$Z^{k1}$ is a single bond, alkylene having 1 to 10 carbons, —$CH_2O$—, —$OCH_2$—, —$CF_2O$—, —$OCF_2$—, —COO—, —OCO—, —CH=CH—, —CF=CF— or —C≡C—;

$X^{k1}$, $X^{k2}$, $X^{k3}$ and $X^{k4}$ are independently hydrogen or fluorine, wherein three or more fluorine cannot exist at the same time in $X^{k1}$, $X^{k2}$, $X^{k3}$ and $X^{k4}$;

nk1 or nk2 is an integer from 0 to 2; and when a plurality of $R^{k1}$, $R^{k2}$, $A^{k1}$, $Z^{k1}$, nk1 or nk2 exist, the plurality may be identical or different each other.

20. A chiral compound represented by general formula (K2-1-1), (K2-1-2), (K2-2-1) or (K2-2-3):

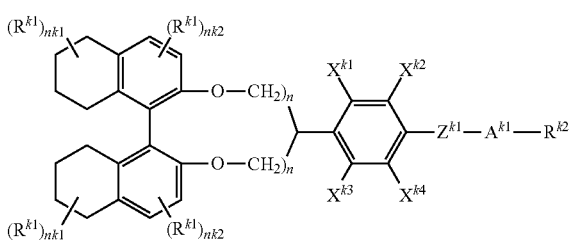
(K2-1-1)

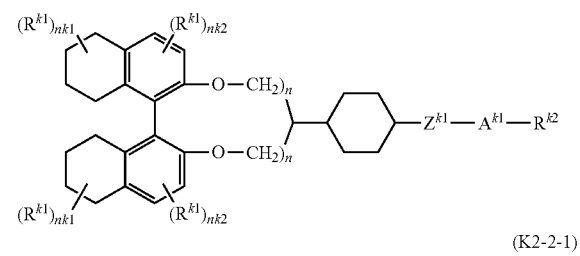
(K2-1-2)

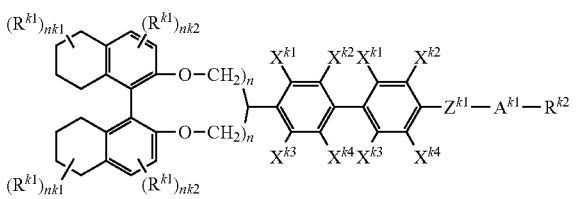
(K2-2-1)

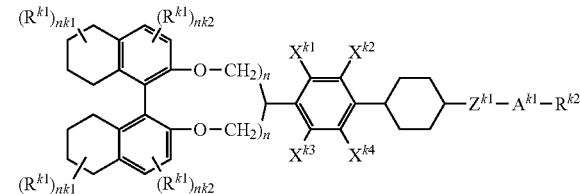
(K2-2-2)

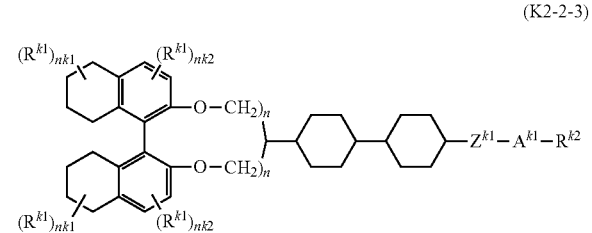
(K2-2-3)

wherein, in formulas (K2-1-1) to (K2-2-3), $R^{k1}$ is hydrogen, halogen, cyano or alkyl having 1 to 5 carbons, and at least one of hydrogen in the alkyl may be replaced by halogen;

$R^{k2}$ is hydrogen, halogen, cyano or alkyl having 1 to 20 carbons, and at least one of hydrogen in the alkyl may be replaced by halogen;

ring $A^{k1}$ is 1,4-phenylene, 1,4-cyclohexylene, 1,3-dioxane-2,5-diyl, tetrahydropyran-2,5-diyl, tetrahydropyran-3,5-diyl, pyrimidine-2,5-diyl or pyridine-2,5-diyl, and at least one of hydrogen in the rings may be replaced by halogen;

n is an integer from 0 to 10;

$Z^{k1}$ is a single bond, alkylene having 1 to 10 carbons, —$CH_2O$—, —$OCH_2$—, —$CF_2O$—, —$OCF_2$—, —COO—, —OCO—, —CH=CH—, —CF=CF— or —C≡C—;

$X^{k1}$, $X^{k2}$, $X^{k3}$ and $X^{k4}$ are independently hydrogen or fluorine, wherein three or more fluorine cannot exist at the same time in $X^{k1}$, $X^{k2}$, $X^{k3}$ and $X^{k4}$;

nk1 or nk2 is an integer from 0 to 2; and when a plurality of $R^{k1}$, $R^{k2}$, $A^{k1}$, $Z^{k1}$, nk1 or nk2 exist, the plurality may be identical or different each other.

* * * * *